US012807963B2

(12) United States Patent
Pearce et al.

(10) Patent No.: US 12,807,963 B2
(45) Date of Patent: Nov. 24, 2026

(54) METHODS AND COMPOSITIONS FOR REDUCING POLYPHENOL OXIDASE ACTIVITY IN PLANTS

(71) Applicant: Colorado State University Research Foundation, Fort Collins, CO (US)

(72) Inventors: Stephen Pearce, Harpenden (GB); Caitlynd Krosch, Fridley, MN (US); Karl Ravet, Fort Collins, CO (US); Rocio Alarcon Reverte, Harpenden (GB); Andrew Katz, Fort Collins, CO (US); Forrest Wold-McGimsey, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 222 days.

(21) Appl. No.: 18/621,953

(22) Filed: Mar. 29, 2024

(65) Prior Publication Data

US 2024/0327855 A1 Oct. 3, 2024

Related U.S. Application Data

(60) Provisional application No. 63/493,525, filed on Mar. 31, 2023.

(51) Int. Cl.

| | |
|---|---|
| ***C12N 15/82*** | (2006.01) |
| ***C12N 9/22*** | (2006.01) |
| ***C12N 15/11*** | (2006.01) |

(52) U.S. Cl.

CPC ........... *C12N 15/8243* (2013.01); *C12N 9/22* (2013.01); *C12N 15/11* (2013.01); *C12N 15/8213* (2013.01); *C12N 2310/20* (2017.05)

(58) Field of Classification Search

None

See application file for complete search history.

(56) References Cited

U.S. PATENT DOCUMENTS

2018/0127766 A1 5/2018 Armstrong et al.

OTHER PUBLICATIONS

Brian S. Beecher et. al., Genetic mapping of new seed-expressed polyphenol oxidase genes in wheat (*Triticum aestivum* L.). Theor Appl Genet (2012) 124:1463-1473 (Year: 2012).*

Shujuan Zhang et. al., CRISPR/Cas9-mediated genome editing for wheat grain quality improvement, Plant Biotechnology Journal (2021) 19, pp. 1684-1686 (Year: 2021).*

Congcong Liu et. al., In-depth genetic analysis reveals conditioning of polyphenol oxidase activity in wheat grains by cis regulation of TaPPO2A-1 expression level, Genomics 112 (2020) 4690-4700 (Year: 2020).*

Matías Nicolás Gonzalez et. al., Reduced Enzymatic Browning in Potato Tubers by Specific Editing of a Polyphenol Oxidase Gene via Ribonucleoprotein Complexes Delivery of the CRISPR/Cas9 System, Front Plant Sci. Jan. 9, 2020:10:1649 (Year: 2020).*

Beecher et al. "Genetic mapping of new seed-expressed polyphenol oxidase genes in wheat (*Triticum aestivum* L.)." Theoretical and Applied Genetics 124 (2012): 1463-1473.

Chi et al. "Reduced polyphenol oxidase gene expression and enzymatic browning in potato (*Solanum tuberosum* L.) with artificial microRNAs." BMC Plant Biology 14 (2014): 1-18.

Demeke et al. "Molecular characterization of wheat polyphenol oxidase (PPO)." Theoretical and Applied Genetics 104 (2002): 813-818.

Gonzalez et al. "Reduced enzymatic browning in potato tubers by specific editing of a polyphenol oxidase gene via ribonucleoprotein complexes delivery of the CRISPR/Cas9 system." Frontiers in Plant Science 10 (2020): 1-12.

He et al. "Allelic variation of polyphenol oxidase (PPO) genes located on chromosomes 2A and 2D and development of functional markers for the PPO genes in common wheat." Theoretical and Applied Genetics 115 (2007): 47-58.

Hystad et al. "Genetic characterization and expression analysis of wheat (*Triticum aestivum*) line 07OR1074 exhibiting very low polyphenol oxidase (PPO) activity." Theoretical and Applied Genetics 128 (2015): 1605-1615.

Liu et al. "In-depth genetic analysis reveals conditioning of polyphenol oxidase activity in wheat grains by cis regulation of TaPPO2A-1 expression level." Genomics 112.6 (2020): 4690-4700.

Murata et al. "A transgenic apple callus showing reduced polyphenol oxidase activity and lower browning potential." Bioscience, biotechnology, and biochemistry 65.2 (2001): 383-388.

Ramirez-Gonzalez et al. "The transcriptional landscape of polyploid wheat." Science 361.6403 (2018): 1-14.

Sun et al. "Alternative splicing in the coding region of Ppo-A1 directly influences the polyphenol oxidase activity in common wheat (*Triticum aestivum* L.)." Functional & integrative genomics 11 (2011): 85-93.

Taketa et al. "Duplicate polyphenol oxidase genes on barley chromosome 2H and their functional differentiation in the phenol reaction of spikes and grains." Journal of experimental botany 61.14 (2010): 3983-3993.

Taranto et al. "Mapping and allelic variations of Ppo-B1 and Ppo-B2 gene-related polyphenol oxidase activity in durum wheat." Molecular Breeding 35 (2015): 1-10.

Tran et al. "The polyphenol oxidase gene family in land plants: Lineage-specific duplication and expansion." BMC genomics 13 (2012): 1-12.

Van Gelder et al. "Sequence and structural features of plant and fungal tyrosinases." Phytochemistry 45.7 (1997): 1309-1323.

(Continued)

*Primary Examiner* — Weihua Fan
*Assistant Examiner* — Yanxin Shen
(74) *Attorney, Agent, or Firm* — McKee, Voorhees & Sease, PLC

(57) ABSTRACT

The disclosure relates to compositions and methods for reducing polyphenol oxidase (PPO) activity in plants, including wheat plants. The compositions comprise plants, plant parts, plant cells, and seeds comprising a mutation in at least one endogenous PPO1 or PPO2 gene. Products produced from the grain of plants have reduced browning.

26 Claims, 5 Drawing Sheets

Specification includes a Sequence Listing.

(56) References Cited

OTHER PUBLICATIONS

Yu et al. "Independent Losses of Function in a Polyphenol Oxidase in Rice: Differentiation in Grain Discoloration between Subspecies and the Role of Positive Selection under Domestication." The Plant Cell, vol. 20 (2008): 2946-2959.
Zhai et al. "Genetic architecture of polyphenol oxidase activity in wheat flour by genome-wide association study." Crop Science 60.3 (2020): 1281-1293.
Zhang et al. "CRISPR/Cas9-mediated genome editing for wheat grain quality improvement." Plant Biotechnology Journal 19.9 (2021): 1-3.

* cited by examiner

SEQUENCE LISTING

```
Sequence total quantity: 74
SEQ ID NO: 1            moltype = DNA  length = 3656
FEATURE                 Location/Qualifiers
source                  1..3656
                        mol_type = genomic DNA
                        organism = Triticum aestivum
SEQUENCE: 1
ggagcacgca aaggggtcat agagattgct ggacgaacaa cagatattgg atatcttgac  60
atggacttgt tgaaattgtt caacatattc ttctgcgtag aagagattgt gatactatcc  120
gaatttttat gcaagtcctc aaaatggaat gactacttgc taaaaaaaca taatatgaga  180
ttcaacactc accatcgatc aatgcaccta taaccatcac acgtaatgcg tcgagaacaa  240
ccgaaccaag gaactttttt gtggagaatc aaaccaagga actagaaatt ttattttcag  300
cctcctttca caaaatggac ttttttttgc gggggcacaa aatggacttg ctcaaattgc  360
aaactcaatc aactttacat ataagttacc cgcaaaaaca aaaaaacttt acatataact  420
gccgcgtcgc cgcatggcac atatggttag caagatcaca gttttttttt ttttttgat  480
ttaaagcaag atcacagttc acatagagct accgtgtctg tcaaaccaaa caaacggctg  540
tacacggtac atgcccggtg cacgcgcact acatataggg acgattggct caggttcacc  600
acaacatctt ttctatccgt gagctagcgg gcggcagcca gaaagcaaac accggcagca  660
tggagagcag tcgcatgcca ctgagtgcca cccctcgcat gccatgcagc ctccaaaccc  720
ttgcgcgccg caaccttctc cgtggccttc acctccggaa ggacgcgagg cagccacggc  780
gtctctcagt ctcatgcgag gcgaccggcg gctgccgcgt cgaccgccgt gaggtgctcc  840
tcggtctcgg cggcgccgcg gctgccggtc tggccacgga caaaggtcga ggcgcgatcg  900
ccgcgcccat ccaggccccg gacctccgca actgccaaac gcccgagctc ccgaacacgc  960
cgccggacac caactgctgc ccgacgcccg gcaccggcat caccgacttc gtgctgccgc  1020
ccgtctcctc gccgctccgc gtgcgtccgg cagcgcacct ggtggacgcg gggtacctgg  1080
ccaagtacga gagggccgtg gcgctcatga agcagctgcc cgccgacgac ccgcgcagct  1140
tcgagcagca gtggcacgtg cactgcgcct actgcgacgc cgcctacgac caggtcgggt  1200
tcccggacct ggagctccag atacacaact gctggctctt cttcccatgg cacaggttcg  1260
tatgggagca atgctacacc taggtaaagt tacgtacaga ttttacgtaa taggcaacgt  1320
gtaggactgc gattggatgg atggatgtgg caggggccca cacgggtgaa aatcaggggg  1380
ggcgatagat ttgttaggta ggttacgtaa ctcttagcag gttggtttcg taggtgtagt  1440
attattgttc gtatggtcaa tgggttatgg atgggacgac ctgcaccttt ctgtgctgaa  1500
cgtcaaggag ccgtcacttg tccctgcgtg ggtttgctga acgtgcaggt tctacctcta  1560
cttccaggag aggatcctcg gcaagctcat cggcgacgac accttcgcgc tgcccttctg  1620
gaactgggac gcgccggccg gcatgacgct gccggccatc tacgccgaca ggtcgtcgcc  1680
gctctacgac gagaggcgcg accccgcgca ccagccgccg gtgctggtcg accttgactc  1740
cagtgggtcc gacaccaata tcccaagaga ccagcagatc gacgagaacc tcaagatcat  1800
gtaccgccag gccagtagta ccaactaaca acctcaagaa tccctgaaaa aattagcaac  1860
ttcaaaaaca ttgttaacgt aaccacagag ttaaccactg gtcattaaaa taacacaaat  1920
gtacgtacgc accagatgat ttcgaacgcg aagaagacgc tgctgttcct gggacagccg  1980
taccgcgccg gcgaccagcc ggacccgggc gccagctccc tggagaacgt gccgcacggc  2040
acggtccacg tctggactgg cgacccaagg cagcccaact tggcggacat gggcaacttc  2100
ttctcggcgg cgcgcgaccc catcttcttc gcgcaccacg gcaacatgga ccgcctgtgg  2160
cacgtctggc gcggcctccg cccgagcaac actgacttca ctgaccccga ctggctcgac  2220
gccgccttcc tcttctacga cgaggaggcc cgccccgtgc gcgtgcgcgt ccgggactgc  2280
ctcgacccgg ccgcgctgcg gtacacgtac caggacgtcg gcctgccgtg gctcaacgcc  2340
aggccggcca aggcgtccag cgggacgccg gcgcccgcca ccaccggtac cctccctgcc  2400
accctggaca gcaccatacg ggtgaccgtg acgaggccca gggtgtcgag gagccgccgg  2460
gaaaaggacg aggaggagga ggtgctggtc gtggaggggga tcgagatcgc cgaccatttc  2520
aacaagttca tcaagttcga cgtgctggtg aacgagcccg agggaggggt ggacggcacg  2580
ccggcgacgg cgacggggta ctgcgccggg agcttcgcgc acacgccgca catggtccgg  2640
cccgaggaga cgaggaaggg gtcggtcaag acggtggcga ggttcggcgt gtgcgacctg  2700
atggacgaca tcggagcgga cggcgaccag acggtggtcg tgtcgctcgt acccaggtgc  2760
ggcggtgagc tggtcaccgt aggcggcgtc agcatcagct acctcaagtg aagttacgta  2820
atgtggtccg ctctcgcgtc ggtggctcgc cgtggtatag aatctatgta atggtgatgg  2880
tgatgaatta taaataagct accgcaagtg actgccgatg aatctctggt cggcgttcac  2940
tgtggtatgg aatctatggt gcgtctcctc gtattgtatt gcagcacgta cgtacgtgca  3000
tgcgtatgtc ctatgtgtaa tggtaattcc aaataagaag agctggagtt aatgggactg  3060
gtggctcggt gcgtacatcc tacctataat cctgtgcgca gcaccataca gtactagtta  3120
ctagttttac cacaataata actatatgca agttgactga atttgtaatt tgggcaagtc  3180
caatttgtgg aaggaggaat ggttggagga ggaagaaagc tggaggttga agaaagaagg  3240
ttgacgttgg atcttcaatc taatggtcca gaatatcgaa ttacccaaaa tatattttca  3300
agcgacttac atgtagccgt tccctagttt gaaggatctg ctaaacctcg gttgcctgaa  3360
aacaaaagtt ggataatcgg ttttagatag gagagaagag agctagagaa gacctggagg  3420
cgacgctgag taggtgacgg tcgtgccctg acgagcgccg gctcaccgaa aacaagccag  3480
agtgggtgac aacatggccg gctggggcca gtcgaggcgg ttgttgatgg tttgggtgct  3540
ggtgcggggc gagccgttag cgccaaaaag gaggggcgtc gagggggcgg cacagtgaag  3600
atagcggcaa gattgcacca taactgaaat tattattttt agacaagcca gaattg      3656

SEQ ID NO: 2            moltype = DNA  length = 3420
FEATURE                 Location/Qualifiers
source                  1..3420
                        mol_type = genomic DNA
                        organism = Triticum aestivum
SEQUENCE: 2
cgcaagcctt ggccacactc ctggccccct ccccctcac ccaccttgtg tcggcgcacg  60
cagccagctg tattgttgcc ggtgccggct cgttcctggc gagatttcgc cgaggacgtc  120
agggcttcgc tcgaattcga ttgatgtgtc caaaaatata ggtgactctc attatcaatc  180
```

-continued

```
ggtaggttca aacacatgta cacatgtcac agtacagtgt ggaactgttt attatgcagt  240
gtaccaaaat tgtcaagcac tctactgtac tatacatagc tgcttagtgt gcatgtcacg  300
acccctttta agatccaagt ggtttgtcac gtttgatagg taagcaccga atggtgagcc  360
atctcaaaaa caaaggtaag cactttaccg tgtatcaact taagtaactt gcgaatcctg  420
aactgcactt tagtccttgc caagttgcca tccaccctcg acgaacagtg accaacagtt  480
gtaaggcagt tcaaccatca cacgtaacca acagtcaaac ccaacagctg cgagccctgc  540
cgcacgtgca cgaagtggca cgcacggcta catatagcac cacacggagc agtgcaacac  600
atgtcacaga ctcacagttc accattttac ctcctcgagt tcaccatgga gatcagcacg  660
agcgtggcaa ggtgcactcg catgccgtgc agcctccaag ccctcgtgcc cacgaaggcg  720
aggcagacgc ggcgcctgac gtgcaaggca accggcggcc gcgtcgaccg ccgcgacgtg  780
ctcctcggcc tcggcagcgc cgcggcggcc gggctgggcg cgcagcgggg ccgaggggcg  840
attgccgcgc ccatccaggc cccggacctc ggcaactgca acccgcccga cctcccgaac  900
acggcgcctg acaccaactg ctgcccgacg tccggcaccg gcatcatcga cttcgtgctg  960
ccgccggcct cctcggcgcc gctccgcgtg cgcccggccg cgcacctggc agacgcggag  1020
tacctggcca agtacgagcg ggccgtggcg ctcatgaagc agctgcccgc cgacgacccg  1080
cgcagcttcg agcagcagtg gcgcgtgcac tgcgcctact gcgacggcgc ctacgaccag  1140
gtcggcttcc cggacctgga gatccaggtg cacaactgct ggctcttctt cccatggcac  1200
aggtacgtaa cgtacaccac ataataaata cgcgttgttt acacataaca catgcatgca  1260
tctccatttt tgtcagctta gtaattgcct aattggtcgt cgcgggtgtg cagtaagcat  1320
gactgcatga gtacgtgtgg gcacctttcg tacagtgcgc cagctgaacg tgccgtaact  1380
tgtcacaatg tttgactttt ttggtgctgc gtgtgtacgt gcaggttcta cctctacttc  1440
cacgagcgga tcctcggcaa gctcatcggc gacgacacct tcgcgctgcc cttctggaac  1500
tgggacgcgc cggacggcat gacgctgccg gcgatctacg ccaacaggtc gtcgccgctc  1560
tacaacgaga ggcgcaaccc cgcccaccag ccgccgttcc cggtcgacct cgacttcaac  1620
gagatagatg tcatcatccc aacagacgag cagatcgacc agaacctcaa catcatgtac  1680
cgccagatgg tgtcgggtgc caagaagact cggctgttca tggggcagcc gtaccgcgcc  1740
ggcgaccagc cggaccctgg cgcgggctcc gtggagaacg tgccgcacgg cacgatgcac  1800
acctggacgg gcgacccggc gcaacccaac aacgaggaca tgggcaactt ctactcggcg  1860
gcgcgcgacc ccatcttctt cgcgcaccac ggcaacatcg accgcctctg gcacgtctgg  1920
cgcggcctcc gccccggcaa cgccgacttc accgacactg actggcttga caccgccttc  1980
ctcttctacg acgaggaggc ccgccccgtg cgcgtccgcg tccgcgactg cctcgacccg  2040
gccgccatgg ggtacgcgta ccaggacgtc ggcctgccgt ggctgaaagc caagccggcc  2100
aagagatccc gcaggacgcc ggcgcccgcc gcgggcgcgc tcccggcgac gctgagggag  2160
accgtgcggg tgacggtgac aaggccccag gtgtcgagga gcgacaagga gaaggaggag  2220
gcggaggagg tgctgatcgt cgaggggatc caggtcgccg accacttcaa gttcgtcaag  2280
ttcgacgtgc tggtgaacgc gcccgagagc ggaggcgatg ccgcgtcggg gtactgcgcc  2340
ggcagcgtcg cgatgacgcc gcacatggtc cggacgaaca agaagaaggg ctccgtgaag  2400
acggtggcga ggttcggcgt ctgcgacctg atggacaaca tcggggcaga cggcgacaag  2460
acggtggtcg tgtcgcttgt gcccaggtgc ggcggcgagc tggtcaccat cggcggcgtc  2520
agcatcggct ataccaagtg aagcaccgcc accgtatata ccgtgtggtg tatatctaaa  2580
caagtcgctc atgagcgatc gttgcgtgct ttacgtcacg tatgtctagc gtatattgcg  2640
ccgtatgtta cgtgcatcta ctgtgcttat attgcagcgt atgtctagcg tattctaata  2700
agaacaattg gaacggtgca ctttattgtc cttacttcat atatagtact catgttacaa  2760
gtacattaat cccactattt tcttaaagtt cctgcaaaaa aatgcatctg tgacattgcc  2820
cgtaaaaata gattttattt taggcaagcc agtgaaatta gatgtgcggg ttagaagaga  2880
gaggattttc taacggagcc agtttctacc ggtgtcctgc tagcttgaag tgcgctttgt  2940
gtgtacgtac acatatcaca tatgaagtat ttgattcatt tcttgattat atatgtgatt  3000
tcttcttttt tgttgggacc cacacactgt ttaggagcag gaccttattg caatcaaaac  3060
attttgttct tttaacccac ggtccatcca tccatacctt tagtatcctt agtctcgtgc  3120
ttcaggattt gccgtccttc cacgtcatcg acaatctttt ggcatttctg aagaacacgt  3180
tctgcgctgg cggcttggca ttctcagcct ccaagtcaga tctcatccac gaccatgagg  3240
agagcaccga ctatgagttc tcttctaagg gaaaggagcc cgcgtgtgac cacagggaga  3300
cacccatgat gtctttgcat gtggctcttt caaggggggg attaagaact caagatcacc  3360
tcggatgaca tgtcttagag taactctagc agaacccgca aaacgctggt ccgtaaaacg  3420
```

```
SEQ ID NO: 3           moltype = DNA  length = 3665
FEATURE                Location/Qualifiers
source                 1..3665
                       mol_type = genomic DNA
                       organism = Triticum aestivum
SEQUENCE: 3
ttacgtgagg gattttcttt gacataattt ataatttcct gctacggagc ccgcaaaggg  60
gttatagata ccgttgtagg aaataaacag cacatggtag atatcttaca tgtggacttg  120
ttgaagttgt tctacatatt attgtgtgta gaagatatta tggtactatt cgacgggtat  180
ttctgtaagt ccaaaatagg atgacattgc caacaaactg aaatatgagt ttcaacgctc  240
accatccatc acagaaaact tataaccatc acacacgcat cgagaacaat caaaccaagg  300
aactggatat atgtaattcg cctgaaaata tatttttagc ctcctttcac caaatggacc  360
tgcccaaatt acaaattctt tttttctttt gctaggtgcc caaattacaa tatatatttt  420
ttgagggtag cccaaattac aaattgaatc aacttacata tagctaccgt gcgaatggca  480
catatggtta gcaagatcac agttcacata tagctgccgt gtcaaacgaa acaacggctg  540
tgcacggtac atgaccggtg cacgcgcact acatataggc acggttggct caagctcacc  600
acaccctgtc tatccgtaag cgggcggcag ccagaaagca cagaccggca gcatggagag  660
cactcgcatg ccactgagtg ccacccctcg catgccatgc agcctccaaa cccttgcgcg  720
ccgcaacctt ctccgtgccc ttcaccaccg caaggacgcg aggcagccac ggcgtctctc  780
aatctcatgc gaggcggccg gcggcggcag cgtcgaccgc cgtgaggtgc tcctcggcct  840
cggcagcgcc gcagctgccg ggctggccac ggaccaaggt cgaggcgcga tcgccgcgcc  900
catccaggcc ccggacctcc gcaattgcca aacgcccgcc ctcccgaaca cgccgccgga  960
caccaactgt tgcccgacgc ccggcaccag catcaccgac ttcgagctgc cgcccgcctc  1020
ctcgccgctc cgcgtgcgtc cggcagcgca cctggtggac gcggagtacc tggccaagta  1080
```

```
cgagagggcc gtggcgctca tgaagcagct gcccgccgat gacccgcgca gcttcgagca  1140
gcagtggcac gtgcactgcg cctactgcga cgccgccttc gaccaggtcg ggttcccgga  1200
cctggagctc cagatacaca actgctggct cttcttccca tggcacaggt acgtatggtc  1260
aatgggttat gggtgtgacg acctgcacct ttctgtgctg aacctcaagg agccatcact  1320
tgtccctgcg tgcgtttgct gaacgtgcag gttctacgtc tacttccacg agaggatcct  1380
cggaaagctc atcggcgacg acaccttcgc gctgccgttc tggaactggg acgcgccggc  1440
cggcatgacg ctgccggcga tctacgccaa caggtcgtca ccgctctacg acgagaggcg  1500
cgaccccgcc caccagccgc cggtgctggt cgaccttgac tccagtggga ccgacgccaa  1560
tatcccaaga gaccagcaga tcgatgagaa cctcaagatc atgtaccgcc aggccagtag  1620
tactatatac taacaacctc ttaaaaaata ctactccctt cgttccaaaa tttgtgtttt  1680
acatttgtct agatacagat gtatctagca ctaaaactta actagataca tccgtattta  1740
ggcaaatact ccctctattc ggaattactt gtttcgaaaa tgaatgtatc tagaactaaa  1800
actcgtctag atacatccat ttctgcgaca agtaattccg aattttggga cggagggagt  1860
attagcgact tcaaaaatat tgtttttttt ttcgactcaa cttaaaaaat attgttaacg  1920
taaccacaga accactggtc attaaattaa gtaacacaaa tgtacgtaca catcagatga  1980
tttcaaacgc gaagaagacg ttgctgttcc tgggacagcc gtaccgcgcc ggcgaccagc  2040
cggacccggg cgcgggctcc gtggagaacg tgccgcacgg cacggtccac ggctggactg  2100
gtgatccaag gcagccgaac ggcgaggaca tgggcaactt ctactcggcg gcgcgcgacc  2160
ccatcttctt cgcgcaccac ggcaacatcg accgcctctg gcatgtctgg cgcggcctcc  2220
gcccgagcaa cgccgacttc accgaccccg actggctcga cgccgccttc ctgttctatg  2280
acgaggaggc tcgccccgtg cgcgtgcgcg tccgggactg ccttgacacg gccgcgctgc  2340
ggtacactta ccaggacgtc ggcctgccgt ggctcaacgc aaggccagcc aaggcgtccg  2400
gcgggacgcc ggcgcctgcc accaccagta ccctccctgc caccctggac aggaccatac  2460
gggtgactgt gacgaggccc agggtgtcca ggagccgccg ggagaaggaa gacgaggagg  2520
aggtggtggt cgtggaggga atcgagatcg ccgaccattt caacaagttc atcaagttcg  2580
acgtgctagt gaacgagccc gagggcggag tgggcagcac gccggcgacg gcgacggggt  2640
actgcgccgg gagcttcgcg cacacgccgc acatggtccg gcccgaggag atgaggaagg  2700
gaccggtcaa gacggtggcg aggttcggcg tgtgcgacct gatggacgac atcggggcgg  2760
acggcgacca gacggtggtc gtgtcgctcg tacccaggtg cggcggtgag ctggtcaccg  2820
tcggcggcgt cagcatcagc tacgtcaagt gaagttacag tggttcgctc tcgcgtcggt  2880
ggctcaccgt ggtatagaat ctatgtaatg gtgatggtga cgaattgtaa ataaggtacc  2940
tcaagtgact gccgatgaag caggcaccca tatatgctct ctcgccggcg ttcgcttgtg  3000
gcatggaatc tattgtgtgt ctcctcgtat tgtattgctt atgtcctatg tgcagtggcg  3060
gagcttgaaa gaaaatgctg ggcgggccag actaaacaag agcacaattt tttttaaaat  3120
tctgaatcat aagcatcagt atgattaccg gatggagcaa gcagtatgta tatatacaac  3180
aaaatacatt ttaaccctga accactatta agttagctaa tacaaaagct ttgagacatt  3240
agacatgtga cttactcaca tactacaaat cgactctccg gtcacccttg cttctaaaat  3300
ctgcaaggac atcttcgtgg ctgtagttct ctagaattcc accctctatg tgaactaaca  3360
gattattggc aagattctca tcttccaggg tctcgctgca cgctgtaaga actcaatacc  3420
ttcgaatgta acagcttcat ttgctcgaac ctattcgtac tggttttggt tatgttgttc  3480
caattcaagc aacggcaata tctggttttc ctgaactcga gttatgtcat ctcttttcct  3540
tttaaaaacc aaatcaattc ttctctgaga ttgattttcc ttgcccatga ttacctgtgt  3600
tgcaatttgt ataagatcag gctattcact ttcttatcaa atggacacaa ctatttttta  3660
tcaac                                                              3665

SEQ ID NO: 4            moltype = DNA  length = 3480
FEATURE                 Location/Qualifiers
source                  1..3480
                        mol_type = genomic DNA
                        organism = Triticum aestivum
SEQUENCE: 4
ccttcgattt gcatgaattt cgttctgttg ttcaattttg tattgaaatg tataggagat  60
cacaaaatga aaacgacaca ggctaaatag tgcgggttca ttctggatcc taaaggcatc  120
actagtggct gttagccggc tcggtgtcat tgaccggtga cctatattct tcacaagcgt  180
gctaaattta ggaccgcaac gcagcccttc gtatgttttg gcaccaaatc gcagcttgcg  240
ccacaaattt gtgacgtgcg cgcaatattg ctcaacatat gcatatgcgt ccgtagcacc  300
gtatagacag cgtgtcaggt gtcagtgcca gtgcatgcag tgtataatac tagcatcccc  360
acacacaaaa aacacccaat cctctagtag ctactcgtat agatccccat tttcgacgaa  420
cgtagttttc tccctcgcac tgccaacaaa ccaaaagcta aggttcaaca cgctccatcg  480
ctcagttcgc tgtaatcatc acacctagta cgtgaagaac ggtcatatta aaccaagcac  540
ctgctgtacg tgggcggcgc acgcactata tataggcacc atccgttacc tcaaaaagtt  600
caccacaact agtgcatccc taaccctaag cgagcagcag ccaggtagca gataccggca  660
gccatggaga gcactcgcgt gctaccgagt gccacccctc gcatgccagg caccctccaa  720
acctttccgc gacgcaacgt tctccgtgat ctccaccacc gcaaggacgc gaggcagcca  780
cggcgtctct cagtctcata cgaggcagcc ggcggcggcc gcgtcgaccg ccgtgaggtg  840
ctcctcggcc tcggcagcgc cgcagctgcc gggctggcca cggaccaagg tcgaggcgtg  900
atcgccgcgc ccatccaggc cccggacctc cgcaactgcc aaacgcccgc cctcccgaac  960
acgccgccgg acaccaactg ctgcccgacg cccagcaccg gcatcaccga cttcgaactg  1020
ccgcccgcct cctcgccgct ccgcgtgcgc ccggccgcgc acctggcgga cgcggagtac  1080
ctggccaagt acgagcgcgc cgtggcgctc atgaagcagc tgcccgccaa tgacccgcgc  1140
agcttcgagc agcagtggca cgtgcactgc gcctactgcg acgccgcctt cgaccaggtc  1200
gggttcccgg acctggagct ccagatacac aactgctggc tcttcttccc atggcacagg  1260
tacgtatggt caatgggttt tgggtgtgac gacctgcacc tttctgtgct gaacctcaag  1320
gagccgtcac ttgtccctgc gtgcaggttc tacgtctact tccacgagag gatcctcggc  1380
aagctcatcg gcgacgacac cttcgcgctg ccgttctgga actgggacgc gccggccggc  1440
atgacactgc cggccatcta cgccaacagg tcgtcgccgc tctacgacga gatgcgcgac  1500
cccgcccacc agccgccggt gctggtcgac cttgactcca gtgggaccga cgccaatatc  1560
ccaagagacc agcagatcga tgagaacctc aagatcatgt accgccaggc cagtagtact  1620
atactaacaa cctcatgaat ccctaaaaaa tactattagc aacttcaaaa atattgtttt  1680
```

```
tttttgcgag tcaacttaaa aaatattatt aacgtaacca caaaaccact ggtcattaaa  1740
ttaaataaca cagatgtacg tgcacatcag atgatttcaa acgcgaagaa gacgctgctg  1800
ttcctgggac agccgtaccg cgccggcgac cagccggacc cgggcgccgt ctccgtggag  1860
aacgtgcccc acggcacggt gcataactgg acaggcgacc caaggcagcc gaacggcgag  1920
gacatgggca acttctactc ggcggcgcgc gaccccatct tcttcgcgca ccacggcatc  1980
atcgaccgcc tgtggcacgt ctggcgcggc ctccgcccga gcaacaccga cttcaccgac  2040
cccgactggc tcgacgccgc cttcctcttc tacgacgagg aggcccgccc cgtgcgcgtg  2100
cgcgtccggg actgcctcga cccggccgcg ctgcggtaca cgtaccagga cgtcggcctg  2160
ccgtggctca acgccaggcc ggccaaggcg tccggcggga cgccggcgcc cgccaccacc  2220
ggtaccctcc ctgccaccct ggacaggacc atacggatga cggtgacgag gcccagggtg  2280
tcgaggagcc gccgggagaa ggacgaggag gaggaggtgc ttgttgtaga ggggatcgag  2340
atcgccgacc atttcaataa gttcatcaag ttcgacgtgc tggtgaacga gcctgaggac  2400
ggagtgggcg gcacgccggc gaggcgacgg ggtactgcgc cgggagcttc gcgcacacgc  2460
cgcacatggt ccggcccgag gagatgagga agggaccggt caagacggtg gcgaggttcg  2520
gcgtgtgcga cctgatggac gacatcgggg cggacggcga ccagacggtg gtcgtgtcgc  2580
tcgtacccag gtgcggcggt gagctggtca ccgtcggcgg cgtcagcatc agctacgtca  2640
agtgaagtta cataatgtgg ttcgctctcg cgttggtggc tcgccgtgcc gtcgtataga  2700
acctatgtaa tggtgatggt gacgaattgt aaataagcta cctcaagtga ctgccgatga  2760
agcaggcacc catctgctct ctcgtcggcg ttcggttgtg gtatggaatc tatggtgtgt  2820
ctcctcgtat tgtattgcag cacgtacgta cgtgcttatg tcctatgtgt attgcagcac  2880
gtacatccaa cctatactcc tgtgcgcggc accatactag ttactagttt tacacaatag  2940
tacgtatcca gctccgcgat gcggccggag ttcgacgaaa acctaaaacc ccttggcggc  3000
gattagggtt tcggtggacg gaaacagcgc tcgtcggctc aatccggcgg ggcgcccact  3060
agttccggcc ggggatggct tcatcagcgg gcggcgagca gcatgaggcg gatcccagct  3120
cctcgcggtc ggacagagcc cggctggagg aggcgctggg aaaacttggg atcacggatg  3180
aggaggctac tcctctagtc gtcgatgacc tagaggaagg cgaaacacaa aagtggctcc  3240
ttgcgggcag agttctgcac aggaaactac ttcatgtcca aactattgct agcgcgctcc  3300
ggcccgcatg ggggaaccct agaggtttga agttcagatc gatgggtgaa aacacgttcg  3360
tggcagagtt tcagacgcaa agagatcgag atcgcatctg gaacgggtcg ccatggcatg  3420
tcagcaagaa cgccgtagta cttgcagaat ttgaagacag tatgcgaccc gatgaggttc  3480

SEQ ID NO: 5            moltype = DNA  length = 3425
FEATURE                 Location/Qualifiers
source                  1..3425
                        mol_type = genomic DNA
                        organism = Triticum aestivum
SEQUENCE: 5
gaccccctcc ccctcttcca ccttgtgtcg gtgcacgcag ccagctgtgt tgttgctagc  60
gccgggtcgt tcctggcgag acttcgccaa ggacgtcagt gcttgtctgg aattcgattg  120
atgcgtccaa aaatataggt gactgcgtat tatcaagcgg taggttcaaa tacatgtacc  180
catgtcacag tacagtgttt aactgtttat gcagtgaacc aaaattgtca agcactctac  240
tgtactatac gtagctgctt agtgtgcatg tcacgatccc ttttaagatc caagtggttt  300
gtcacgtttg ataggtatgc actttactac tatttcggca tgaatggtga gctatctcaa  360
aaacaaagat aagcacttta ccgtgtatat caacttaagt aacttgcgaa tcgtgaactg  420
ctctttagtc cttgccatcc accctcgacg aacagtgacc aacagttgta atgcagttca  480
accatcacac gcactgatca cacgtaacca acagtcaaac ccaacagctg cgagccctgc  540
cgcacgtgca cgaagtggca cgcacggcta catatagcac cacacggagc agtgcaacac  600
atgtcacaga cccacagttc accattttac ctcctcgagt tcaccatgga gatcagcacg  660
agcgtgccac ggtgcaccgc caccccgggc gctcgcatgc cgtgcagcct ccaagccgtc  720
gtgcccacga aagcgaggca gccacggcac ctgtcgtgca aggcaacggg cggccgtgtc  780
gaccgccgtg acgtgctcct cggcatcggc agcgccgcgg cgaccgggct gggcaggcag  840
agaggccgag gggcgatcgc cgcgcccatc caggccccgg acctcggcaa ctgcaacccg  900
cccgacctcc cgaacacggc gccggacacc aactgctgcc cgacgtccgg caccgggatc  960
atcgacttcg tgctgccgcc ggcctcctcg gcgccgctcc gcgtgcgccc ggccgcgcac  1020
ctggcggacg cggagtacct ggccaagtac gagcgggctg tggcgctcat gaagcagctg  1080
cccgccgacg acccccgcag cttcgagcag cagtggcgcg tgcactgcgc ctactgcgac  1140
ggcgcgtacg accaggtcgg cttcccggac ctggagatcc aggtgcacaa ctgctggctc  1200
ttcttcccat ggcacaggta cgtaacgtac acaacataaa tacgtgttgt ttatacacat  1260
gcatgcatgt ccatttttgt caggtcgtcg ggtgtacagt cagtatgact gcatgagtac  1320
gtgtcggtag cggcctgcac ctttcgtaca gtgcgccagc tcaacgtgcc gtcaacttgt  1380
cggtagcggt ctgacttctt tggtgctgcg tacgtgcagg ttctacctct acttccacga  1440
gaggatcctc ggcaagctca tcggcgacga caccttcgcg ctgcccttct ggaactggga  1500
cgcgccggcc ggcatgacgc tgccggcgat ctacgccaac aggtcgtcgc cgctctacaa  1560
tgagaggcgc gaccccgccc accagccgcc gttcccggtc gacctcgact acaacgagat  1620
agatgtcatc atcccaacag acgagcagat cgaccagaac ctcaacatca tgtaccgcca  1680
ggccagtaca actaaaacta atacacaata tttgcagacg cagtaccaaa atctcttgaa  1740
gttatcacgt taatatatca atctgcgtgc gtcgttcaga tggtgtcgag tgccaagaag  1800
actcggctgt tcatggggca gccataccgc gccggcgacc agccggaccc gggagcgggc  1860
tccctggaga acctgccgca caacacggtg cacatctgga cgggcgaccc ggcgcagccc  1920
aacagcgagg acatgggcaa cttctactcg gcggcgcgcg accccatctt cttcgcgcac  1980
cacggcaaca tcgaccgcct ctggcacgtc tggcgcggcc tccgccgggg caacgccaac  2040
ttcaccgacg ccgactggct tgacaccgcc ttcctcttct acgacgagga ggcccgcccc  2100
gtgcgcgtcc gcgtccgcga ctgcctcgac ccggccgcca tggggtactc ctaccaggac  2160
gtcggcctgc cgtggctgaa ggccaaaccg ggcaagagat cccgcaggac gccggcgccc  2220
gcggcgggcg cgctcccggc gacgctgagg gagaccgtgc gggtgacggt gacaaggccc  2280
caggtgtcga ggagcgacaa ggagaaggag gaggcggagg aggtgctgat catcgagggg  2340
atccaggtcg ccgaccactt caagttcgtc aagttcgacg tgctggtgaa cgcgcccgag  2400
agcggaggcg atgccgcgtc ggggtactgc gccggcagcg tcgcgatgac gccgcacatg  2460
gtccggacga acaagaagaa gggctccatg aagacggtgg cgaggttcgg cgtctgcgac  2520
```

```
ctgatggaca acatcggggc agacggcgac aagacggtcg tcgtgtcact cgtgccaagg  2580
tgcggcggcg agctggtcac cgtcggcggc gtcagcatcg gctataccaa gtgaagcatc  2640
gccaccgtat ataccgtgtg gtgtatagct tgacaagctg ctcatgagcg atcgttgcgt  2700
gctttactgc atctactgtg cttataccaa gtgaagcacc gtatgtacgt gcgtatgtcg  2760
tatccaaata aaaacaattg taatggtgca ctcccattgt cctataactc atcactttct  2820
ttccgcaaaa aataacacta atcactttag ctatatatat atatatatat atatatatat  2880
atatatatat atatatatat atatatatat atatatatac acgtataggt aagtcgactg  2940
aaaattaatt tcggatcagt caatttttag gccgttgatt tctgctttga aatttgtgat  3000
catttttctt tgtcaagtct gtatattgtt tgagcgacgc tacaccttca cagccgtttg  3060
atctggcgca tccatcgacc cgactctttc ctcataattg caacaaagac agtgttgcgg  3120
aaccgtttgc acatatctct tgttgcggaa acttttgcaa tagagatttt gttgtaattt  3180
tttttcgcac taactttttt gaaacacgtg tgtcgttgcg gacggacttc tgcaacacag  3240
atgatgctgc agaatttttt tctcacctta atgtttttgt aacatgggcg ttgttgcggg  3300
atgacttctg caacccagat gatgttgcag aaaaatggca gaggcacgcg tccagtgatg  3360
taggtcctgg gcggttgata gagttgcatg tcgtccgatt aaacttgtac ctaacggctg  3420
cacac                                                               3425

SEQ ID NO: 6            moltype = DNA  length = 3726
FEATURE                 Location/Qualifiers
source                  1..3726
                        mol_type = genomic DNA
                        organism = Triticum aestivum
SEQUENCE: 6
ccgccgccac gaccacgagg tcggcccatc tacgaccggc gccgtcgaca cgacggactt  60
cagcgaggaa gaatggacat gggacggcac cacggcttgt gtaacaggag ggccaccccc  120
acgttttaaa cttcccttcc tacagtttca cttctcaggg cttgcggctg aggttgacgg  180
acatgggaag acaggaagag gaatatagat gcctccaagg ccggcgaaga tcttaaacta  240
ggttaaaaaa gtgtttaatt cccccgcaaa aaaagtgttt aattgaaata tgttgaaaat  300
gtaatgagtt tgcttcgtga gaccttcgcg ctgcccttct ggaatataat actagcatcc  360
tcacacacaa aaaacaccca gtcactctag tagctactca tatatagatc cccattttcg  420
acgaacataa ttttctccct cgcactgcca acaaaccaaa ggccaagttt caacacgctc  480
catcgatcag tgcactgtaa ccatcacacg tagaacgtga agaacggtca aaaccaatca  540
cctgctgtac gtgggtggcg cacgcactat atataggcac catccgttac ctcaaaagtt  600
caccacaact agtgcattgc atccctaacc ctaagcgagc agcagccagg tagcagacac  660
cggcagccat ggagagcact cgcgtgctac cgagtgccaa ccatcgcatg ccatgcagcc  720
tccaaacctt tccgcgacgc aacgttctcc gtgcccttca ccgccgcaag gacgcaaggc  780
agccacgtcg tatctcaatc tcatgcgagg cgaccggcgg cggtcgcgtc gaccgccgtg  840
aggtgctcct cggcctcggc ggcgccgcag ctgcggggct ggccacggac caaggtcgag  900
gcgcgatcgc cgcgcccatc caggccccgg acctccgcaa ctgccaaacg cccgacctcc  960
cgaacacgcc gccggacacc aactgctgcc cgacgcccgg caccggcatc accgactttg  1020
agctgccgcc cgcttcctcg ccgctccgcg tgcgtccggc agcgcacctg gtggacgcgg  1080
agtacctggc caagtacgag agggccgtgg cgctcatgaa gcagctgcct gccgatgacc  1140
cgcgcagctt cgagcagcag tggcacgtgc actgcgccta ctgcgacgcc gccttcgacc  1200
aggtcgggtt cccggacctt gagatccagg tgcacaactg ctggctcttc ttcccatggc  1260
acaggttcgt atggtcaatg ggttaatggg tgcgacgact tgcacctttc tgtgctgaac  1320
ctcaaggagc cgtcacttgt ccctgcgtgc gtttgctgaa cgtgcaggtt ctacgtctac  1380
ttccacgaga ggatcctcgg caagctcatc ggcgacgaca ccttcgcgct gcccttctgg  1440
aactgggacg cgccggccgg catgacgctg ccggcgatct acgccaacag gtcgtcgccg  1500
ctctacgacg agaggcgcga ccccgcccac cagccgcggg tgctgaccga ccttgactcc  1560
agtgggaccg acgccaatat cccaagagac cagcagatcg atcagaacct caagatcatg  1620
taccgccagg ccagtagtac taattaacaa cctcaagaat ccctaaacaa aatgagtagc  1680
aacttcaaaa atattgttaa ggtaaccaca gaaccactgg tcatgaaata acacaaatgt  1740
acgtacgcac cagatgattt cggacgcgaa gaagacgctg ctgttcctgg gacagccgta  1800
ccgcgccggc gaccagccgg acccgggcgc gggctccctg gagaacgtgc cgcacggcac  1860
ggtccacgtc tggactggcg acccggcgca gccgaacttg gaggacatgg gcaacttctt  1920
ctcggcggcg cgcgacccca tcttcttcgc gcaccacggc aacatcgacc gcctgtggca  1980
cgtctggcgc cgcctccgcc cgagcaacac cgacttcacc gaccccgact ggctcgacgc  2040
cgccttcctc ttctacgacg aggaggcccg ccccgtgcgc gtgcgcgtcc gggactgcct  2100
cgacccggcc gcgctgcggt acacgtacca ggacgtcggc ctgccgtggc tcaacgccag  2160
gccggccaag gcgtccggcg ggacgccggc gcccgccaca accggtaccc tccctgccac  2220
cctggacagg accatacggg tgacggtgac gaggcccaga gtgtccagga gccgccggga  2280
gaaggaggag gaggaggagg tgctggtcgt ggaggggatc gagatcgccg accatttcaa  2340
caagttcgtc aagttcgacg tgttggtgaa cgagcccgag ggcggagtgg gcagcacgcc  2400
ggcgacggcg acggggtact gcgctgggag cttcgcgcat acgccgcaca tggtccggcc  2460
cgaggagatg aggaagggac cggtcaagac ggtggcgagg ttcggcgtgt gcgacctgat  2520
ggacgacatc ggggcggacg acgaccagac ggtggtggtg tcgctcgtac ccaggtgcgg  2580
cggtgagctg gtcaccgttg gcggcgtcag catcagctac ctcaagtgaa gttacctaat  2640
gtggtccgct ctcgcgtcgg tggctcgccg tggtatagaa tctatgtaat ggtgatggtg  2700
atgaattata aataggggtc tgctaattct cagtcgactg agaattagtg aaatctcagt  2760
cgacaggatt aaccatacga ttcgattgac ctgtatttat cgctgatgta tttttgtttt  2820
tcaaaaccta ttgggctttc tctatttgag cggctggcgg ctgcatgggc tgtgggctac  2880
ggcttgtggt ccttctcatt ttccctttc tgttttttt atttcttaa tagatatccc  2940
acgtaaatat attgtatttt ttgtttttct gttaggtttg tgtgtataca aagaagatac  3000
gtgtacttat ctagcttttt ttctacttta ttatttattt tctattttct cattttgtgt  3060
atttattttt atatgtttta tttgtctgtt ttacttctat ttctactttt gcctattttt  3120
atcattcatc tttggaagat ttaagttttg tagaatttac attttgacac gcatggacaa  3180
tttttattct cacttgttgt tgtcttttct acatgttttt gttttaattt tattcatgta  3240
gtacacaaaa atacattttt catcatgttt atatgtttta tttgtttgtt tttacttcta  3300
tttcttcttc tttgtttgtt tgtttttggg cgtgattcaa aggggaacgg gcagatatgt  3360
```

-continued

```
gtgctcccgt cgcaataccg atggagatgg gtgacgcaat accgatggag atgggtgacg  3420
ctgctgatgg agtattttat ctccgttatt atccgttgtc ttttttgtct tttttctttt  3480
ttgcttctgg ttcgagtagg ttgaatcaag tacagatcat taggggtacc agaaggttaa  3540
attaagcaga gattagaagt aatctacttt cttttttgtt tctggttcga gtaggttgaa  3600
tcaagtacaa atcagtagag gtactagaag gttgaattaa gtagagatta gtagtaatct  3660
actttctttt ttgtttctgg ttcaagtagg ttcaatcaag tacaaatcag tagggtacca  3720
gaaggt                                                             3726

SEQ ID NO: 7            moltype = DNA  length = 3358
FEATURE                 Location/Qualifiers
source                  1..3358
                        mol_type = genomic DNA
                        organism = Triticum aestivum
SEQUENCE: 7
tctttgccat gcttctgccc ccctccccc tcacccacct tgcgtcgacg cacacagtca  60
gttgtgttgg tgtcggcgcc ggctcgttcc tagcgagact tcaccgaaga cgtcagggct  120
tcgctggaat tcgattgatg cgtccaaaaa tataggtgac tgcgtattat caagcggtag  180
gttcaaatac atgtacacgt gtcacagtac agtgtttaac tgtttattat gcaagtgtac  240
caaaattgtc aagcgctcta ctgtactata cgtagctgct tagtgtgcat gttacgatcc  300
cttttaagat ccaagtggtt cgtcacgttt gataggtagg cactttacca ccattcggca  360
tgaatggtga gctatctcaa aaacaaaggt aagcacttta ccgcgtatca acttaagtaa  420
cttgcgaatc ctgaactgct ctttagtcct tgccatccac cctcgacgaa cagtgaccaa  480
cagttgcagt tcaaccatca cgcgtaacca acagtcaaac ccaacagctg cgagccctgc  540
cgcacgtgca cgaagtggca cgcacggcta catatagcac cacacggagc agtgcaacac  600
atgtcacaga ctcacagttc accattttac ctccccgagt tcaccatgga gatcagcacg  660
agcgtggcaa ggtgcactcg catgccgtgc agcctccaag ccctcgtgcc cacgaagctg  720
aggctgccac ggcgtctgac gtgcaaggca acgggcggcc gcgtcgaccg ccgtgacgtg  780
ctcctcggcc tcggcagcgc cgcggcggcc gggctgggca cgcagagagg ccgaggggcg  840
atcgccgcgc ccatccaggc cccggacctc ggcaactgca acccgcccga cctcccgaac  900
acggcgccgg acaccaactg ctgcccgacg tccggcaccg gcatcatcga tttcgtgctg  960
ccgccggcct cctcggcggc gctccgcgtg cgcccggccg cgcacctggc ggacgcggag  1020
cacctggcca agtacgagcg ggccgtggcg ctcatgaagc agctgcccgc cgacgacccg  1080
cgcagcttcg agcagcagtg gcgcgtgcac tgcgcctact gcgacggcgc gtacgaccag  1140
gtcggtttcc cggacctgga gatccaggtg cacaactgct ggctcttctt cccatggcac  1200
aggttcgtaa cgtacaccac ataaatactc catgtttttt atacacatac acatgcatgc  1260
atgtccattt ttgtcagctt agtaattgct cgtgggtcgg gtgtgcagta agcatgactg  1320
catgagtacg tttgggtagc ggcctgcacc tttcgtacag tgcgccagct gaacgcgacg  1380
tgttgacttt tttggtgctg cgtgcgtacg tgcaggttct acctctactt ccacgagagg  1440
atcctcggca agctcatcgg cgacgacacc ttcgcgctgc ccttctggaa ctgggacgcg  1500
ccggccggca tgacgctgcc ggcgatctac gccaacaggt cgtcgccgct ctacaacgag  1560
aggcgcaacc ccgcccacca gccgccgttc ccggtcgacc tcgactacaa cgagatagat  1620
gtcatcatcc caacagacga gcagatcgac cagaacctca acatcatgta ccgccagatg  1680
gtgtcgggtg ccaagaagac taggctgttc atggggcagc cgtaccgcgc cggcgaccag  1740
ccggacccgg gagcgggctc cgtggagaac gtgccgcacg gcacgatgca cacctggacg  1800
ggcgacccgg cgcagcccaa caacgaggac atgggcaact tctactcggc ggcgcgcgac  1860
cccatcttct tcgcgcacca cggcaacatc gaccgcctct ggcacgtctg gcgcggcctc  1920
cgcccgagca acaccgactt cgccgacgcc gactggcttg acaccgcctt cctcttctac  1980
gacgaggagg cccgccccgt gcgcgtccgc gtccgcgact gcctcgaccc agccgccatg  2040
gggtacgcct accaggacgt cggcctgccc tggctgaagg ccaagccggc caagagatcc  2100
cgcaggacgc cggcgcccgc cgcgggcgcg ctcccggcga cgctgaggga gaccgtgcgg  2160
gtgacggtga caaggcccca ggtgtcgagg agcgacaagg agaaggagga ggcggaggag  2220
gtgctgatca tcgaggggat ccaggtcgcc gaccacttca agttcgtcaa gttcgacgtg  2280
ctggtgaacg cgcccgagag cggaggcgat gccgcgtcgg ggtactgtgc cggcagcgtc  2340
gcgatgacgc cgcacatggt ccggacgaac aagaagaagg gctccatgaa gacggtggcg  2400
aggttcggcg tctgcgacct gatggacaac atcggggcag acggcgacaa gacggtggtc  2460
gtgtcgctcg tgcccaggtg cggcggcgag ctggtcacca tcggcggcgt cagcatcggc  2520
tataccaagt gaagcatcgc caccgtatat accgtgtggt gcatagcttg acaagctgct  2580
cataagcgat cgttgcgtgc tttactgcat ctactgtgct tatattgcac cgtatgtacg  2640
tgcgtatgtc gtatccaaat aaaaacaaca gttttgctag aactcattta gatgagattt  2700
aatttggtct cattcacctt ttatagccat tggatgtggt gctataagat gcgtgtgtgc  2760
tgatatgggt tgtatccgtt cttgtttttc agatgaatga gaccaaatta cgtctcatct  2820
agatgagttc taggtactcc ctaaaaacaa ttataacggt gcactcccat tgtcctataa  2880
ctcatcactt tctttcccgc aaaaaaacac taatcacttt agctatatat acgtataagt  2940
aagtcgactg aaatttaatt tcggatcagt caatttttag gccgttgatt tctgctttga  3000
aatttgtgat cattttttct tgccaagtct gtatattgtt tgggcgacgc tacgcgtcca  3060
ccagcggatt atttttaaag accagccacc ttcatagcca atttgatctg gcgcatccat  3120
cgaccctgct ttttcgtcac aattgcaata aaggcagtgt tgcggaaccg tttgtacata  3180
tctcttgttg tggaaacttt tccaatagag atttcgttgt agattttttc ccattaactt  3240
ttttgaaaca tgtgtgtcgt tgcggacgga cttctgcaac acagatgatg ctgcagaatt  3300
tttttctcat cttaatgttt ttgtaacatg gccgttgttg cgggatgact tctaccac    3358

SEQ ID NO: 8            moltype = DNA  length = 1734
FEATURE                 Location/Qualifiers
source                  1..1734
                        mol_type = other DNA
                        organism = synthetic construct
SEQUENCE: 8
atggagagca gtcgcatgcc actgagtgcc acccctcgca tgccatgcag cctccaaacc  60
cttgcgcgcc gcaaccttct ccgtggcctt cacctccgga aggacgcgag gcagccacgg  120
```

```
cgtctctcag tctcatgcga ggcgaccggc ggctgccgcg tcgaccgccg tgaggtgctc  180
ctcggtctcg gcggcgccgc ggctgccggt ctggccacgg acaaaggtcg aggcgcgatc  240
gccgcgccca tccaggcccc ggacctccgc aactgccaaa cgcccgagct cccgaacacg  300
ccgccggaca ccaactgctg cccgacgccc ggcaccggca tcaccgactt cgtgctgccg  360
cccgtctcct cgccgctccg cgtgcgtccg gcagcgcacc tggtggacgc ggggtacctg  420
gccaagtacg agagggccgt ggcgctcatg aagcagctgc ccgccgacga cccgcgcagc  480
ttcgagcagc agtggcacgt gcactgcgcc tactgcgacg ccgcctacga ccaggtcggg  540
ttcccggacc tggagctcca gatacacaac tgctggctct tcttcccatg gcacaggttc  600
tacctctact tccaggagag gatcctcggc aagctcatcg gcgacgacac cttcgcgctg  660
cccttctgga actgggacgc gccggccggc atgacgctgc cggccatcta cgccgacagg  720
tcgtcgccgc tctacgacga gaggcgcgac cccgcgcacc agccgccggt gctggtcgac  780
cttgactcca gtgggtccga caccaatatc ccaagagacc agcagatcga cgagaacctc  840
aagatcatgt accgccagat gatttcgaac gcgaagaaga cgctgctgtt cctgggacag  900
ccgtaccgcg ccggcgacca gccggacccg ggcgccagct ccctggagaa cgtgccgcac  960
ggcacggtcc acgtctggac tggcgaccca aggcagccca acttggcgga catgggcaac  1020
ttcttctcgg cggcgcgcga ccccatcttc ttcgcgcacc acggcaacat ggaccgcctg  1080
tggcacgtct ggcgcggcct ccgcccgagc aacactgact tcactgaccc cgactggctc  1140
gacgccgcct tcctcttcta cgacgaggag gcccgccccg tgcgcgtgcg cgtccgggac  1200
tgcctcgacc cggccgcgct gcggtacacg taccaggacg tcggcctgcc gtggctcaac  1260
gccaggccgg ccaaggcgtc cagcgggacg ccggcgcccg ccaccaccgg taccctccct  1320
gccaccctgg acagcaccat acgggtgacc gtgacgaggc ccagggtgtc gaggagccgc  1380
cgggaaaagg acgaggagga ggaggtgctg gtcgtggagg ggatcgagat cgccgaccat  1440
ttcaacaagt tcatcaagtt cgacgtgctg gtgaacgagc ccgagggagg ggtggacggc  1500
acgccggcga cggcgacggg gtactgcgcc gggagcttcg cgcacacgcc gcacatggtc  1560
cggcccgagg agacgaggaa ggggtcggtc aagacggtgg cgaggttcgg cgtgtgcgac  1620
ctgatggacg acatcggagc ggacggcgac cagacggtgg tcgtgtcgct cgtacccagg  1680
tgcggcggtg agctggtcac cgtaggcggc gtcagcatca gctacctcaa gtga        1734
```

```
SEQ ID NO: 9            moltype = DNA  length = 1719
FEATURE                 Location/Qualifiers
source                  1..1719
                        mol_type = other DNA
                        organism = synthetic construct
SEQUENCE: 9
atgtcacaga ctcacagttc accattttac ctcctcgagt tcaccatgga gatcagcacg  60
agcgtggcaa ggtgcactcg catgccgtgc agcctccaag ccctcgtgcc cacgaaggcg  120
aggcagacgc ggcgcctgac gtgcaaggca accggcggcc gcgtcgaccg ccgcgacgtg  180
ctcctcggcc tcggcagcgc cgcggcggcc gggctgggcg cgcagcgggg ccgagggggcg  240
attgccgcgc ccatccaggc cccggacctc ggcaactgca acccgcccga cctcccgaac  300
acggcgcctg acaccaactg ctgcccgacg tccggcaccg gcatcatcga cttcgtgctg  360
ccgccggcct cctcggcgcc gctccgcgtg cgcccggccg cgcacctggc agacgcggag  420
tacctggcca agtacgagcg ggccgtggcg ctcatgaagc agctgcccgc cgacgacccg  480
cgcagcttcg agcagcagtg gcgcgtgcac tgcgcctact gcgacggcgc ctacgaccag  540
gtcggcttcc cggacctgga gatccaggtg cacaactgct ggctcttctt cccatggcac  600
aggttctacc tctacttcca cgagcggatc ctcggcaagc tcatcggcga cgacaccttc  660
gcgctgccct tctggaactg ggacgcgccg gacggcatga cgctgccggc gatctacgcc  720
aacaggtcgt cgccgctcta caacgagagg cgcaaccccg cccaccagcc gccgttcccg  780
gtcgacctcg acttcaacga gatagatgtc atcatcccaa cagacgagca gatcgaccag  840
aacctcaaca tcatgtaccg ccagatggtg tcgggtgcca agaagactcg gctgttcatg  900
gggcagccgt accgcgccgg cgaccagccg gaccctggcg cgggctccgt ggagaacgtg  960
ccgcacggca cgatgcacac ctggacgggc gacccggcgc aacccaacaa cgaggacatg  1020
ggcaacttct actcggcggc gcgcgacccc atcttcttcg cgcaccacgg caacatcgac  1080
cgcctctggc acgtctggcg cggcctccgc cccggcaacg ccgacttcac cgacactgac  1140
tggcttgaca ccgccttcct cttctacgac gaggaggccc gccccgtgcg cgtccgcgtc  1200
cgcgactgcc tcgacccggc cgccatgggg tacgcgtacc aggacgtcgg cctgccgtgg  1260
ctgaaagcca agccggccaa gagatcccgc aggacgccgg cgcccgccgc gggcgcgctc  1320
ccggcgacgc tgagggagac cgtgcgggtg acggtgacaa ggccccaggt gtcgaggagc  1380
gacaaggaga aggaggaggc ggaggaggtg ctgatcgtcg aggggatcca ggtcgccgac  1440
cacttcaagt tcgtcaagtt cgacgtgctg gtgaacgcgc ccgagagcgg aggcgatgcc  1500
gcgtcggggt actgcgccgg cagcgtcgcg atgacgccgc acatggtccg gacgaacaag  1560
aagaagggct ccgtgaagac ggtggcgagg ttcggcgtct gcgacctgat ggacaacatc  1620
ggggcagacg gcgacaagac ggtggtcgtg tcgcttgtgc ccaggtgcgg cggcgagctg  1680
gtcaccatcg gcggcgtcag catcggctat accaagtga                         1719
```

```
SEQ ID NO: 10           moltype = DNA  length = 1734
FEATURE                 Location/Qualifiers
source                  1..1734
                        mol_type = other DNA
                        organism = synthetic construct
SEQUENCE: 10
atggagagca ctcgcatgcc actgagtgcc acccctcgca tgccatgcag cctccaaacc  60
cttgcgcgcc gcaaccttct ccgtgccctt caccaccgca aggacgcgag gcagccacgg  120
cgtctctcaa tctcatgcga ggcggccggc ggcggcagcg tcgaccgccg tgaggtgctc  180
ctcggcctcg gcagcgccgc agctgccggg ctggccacgg accaaggtcg aggcgcgatc  240
gccgcgccca tccaggcccc ggacctccgc aattgccaaa cgcccgccct cccgaacacg  300
ccgccggaca ccaactgttg cccgacgccc ggcaccagca tcaccgactt cgagctgccg  360
cccgcctcct cgccgctccg cgtgcgtccg gcagcgcacc tggtggacgc ggagtacctg  420
gccaagtacg agagggccgt ggcgctcatg aagcagctgc ccgccgatga cccgcgcagc  480
ttcgagcagc agtggcacgt gcactgcgcc tactgcgacg ccgccttcga ccaggtcggg  540
```

```
ttcccggacc tggagctcca gatacacaac tgctggctct tcttcccatg gcacaggttc  600
tacgtctact tccacgagag gatcctcgga aagctcatcg gcgacgacac cttcgcgctg  660
ccgttctgga actgggacgc gccggccggc atgacgctgc cggcgatcta cgccaacagg  720
tcgtcaccgc tctacgacga gaggcgcgac cccgcccacc agccgccggt gctggtcgac  780
cttgactcca gtgggaccga cgccaatatc ccaagagacc agcagatcga tgagaacctc  840
aagatcatgt accgccagat gatttcaaac gcgaagaaga cgttgctgtt cctgggacag  900
ccgtaccgcg ccggcgacca gccggacccg ggcgcgggct ccgtggagaa cgtgccgcac  960
ggcacggtcc acggctggac tggtgatcca aggcagccga acggcgagga catgggcaac  1020
ttctactcgg cggcgcgcga ccccatcttc ttcgcgcacc acggcaacat cgaccgcctc  1080
tggcatgtct ggcgcggcct ccgcccgagc aacgccgact tcaccgaccc cgactggctc  1140
gacgccgcct tcctgttcta tgacgaggag gctcgccccg tgcgcgtgcg cgtccgggac  1200
tgccttgaca cggccgcgct gcggtacact taccaggacg tcggcctgcc gtggctcaac  1260
gcaaggccag ccaaggcgtc cggcgggacg ccggcgcctg ccaccaccag taccctccct  1320
gccaccctgg acaggaccat acgggtgact gtgacgaggc ccagggtgtc caggagccgc  1380
cgggagaagg aagacgagga ggaggtggtg gtcgtggagg gaatcgagat cgccgaccat  1440
ttcaacaagt tcatcaagtt cgacgtgcta gtgaacgagc ccgagggcgg agtgggcagc  1500
acgccggcga cggcgacggg gtactgcgcc gggagcttcg cgcacacgcc gcacatggtc  1560
cggcccgagg agatgaggaa gggaccggtc aagacggtgg cgaggttcgg cgtgtgcgac  1620
ctgatggacg acatcggggc ggacggcgac cagacggtgg tcgtgtcgct cgtacccagg  1680
tgcggcggtg agctggtcac cgtcggcggc gtcagcatca gctacgtcaa gtga        1734
```

```
SEQ ID NO: 11          moltype = DNA  length = 1733
FEATURE                Location/Qualifiers
source                 1..1733
                       mol_type = other DNA
                       organism = synthetic construct
SEQUENCE: 11
atggagagca ctcgcgtgct accgagtgcc acccctcgca tgccaggcac cctccaaacc  60
tttccgcgac gcaacgttct ccgtgatctc caccaccgca aggacgcgag gcagccacgg  120
cgtctctcag tctcatacga ggcagccggc ggcggccgcg tcgaccgccg tgaggtgctc  180
ctcggcctcg gcagcgccgc agctgccggg ctggccacgg accaaggtcg aggcgtgatc  240
gccgcgccca tccaggcccc ggacctccgc aactgccaaa cgcccgccct cccgaacacg  300
ccgccggaca ccaactgctg cccgacgccc agcaccggca tcaccgactt cgaactgccg  360
cccgcctcct cgccgctccg cgtgcgcccg gccgcgcacc tggcggacgc ggagtacctg  420
gccaagtacg agcgcgccgt ggcgctcatg aagcagctgc ccgccaatga cccgcgcagc  480
ttcgagcagc agtggcacgt gcactgcgcc tactgcgacg ccgccttcga ccaggtcggg  540
ttcccggacc tggagctcca gatacacaac tgctggctct tcttcccatg gcacaggttc  600
tacgtctact tccacgagag gatcctcggc aagctcatcg gcgacgacac cttcgcgctg  660
ccgttctgga actgggacgc gccggccggc atgacactgc cggccatcta cgccaacagg  720
tcgtcgccgc tctacgacga gatgcgcgac cccgcccacc agccgccggt gctggtcgac  780
cttgactcca gtgggaccga cgccaatatc ccaagagacc agcagatcga tgagaacctc  840
aagatcatgt accgccagat gatttcaaac gcgaagaaga cgctgctgtt cctgggacag  900
ccgtaccgcg ccggcgacca gccggacccg ggcgccgtct ccgtggagaa cgtgccccac  960
ggcacggtgc ataactggac aggcgaccca aggcagccga acggcgagga catgggcaac  1020
ttctactcgg cggcgcgcga ccccatcttc ttcgcgcacc acggcatcat cgaccgcctg  1080
tggcacgtct ggcgcggcct ccgcccgagc aacaccgact tcaccgaccc cgactggctc  1140
gacgccgcct tcctcttcta cgacgaggag gcccgccccg tgcgcgtgcg cgtccgggac  1200
tgcctcgacc cggccgcgct gcggtacacg taccaggacg tcggcctgcc gtggctcaac  1260
gccaggccgg ccaaggcgtc cggcgggacg ccggcgcccg ccaccaccgg taccctccct  1320
gccaccctgg acaggaccat acggatgacg gtgacgaggc ccagggtgtc gaggagccgc  1380
cgggagaagg acgaggagga ggaggtgctt gttgtagagg ggatcgagat cgccgaccat  1440
ttcaataagt tcatcaagtt cgacgtgctg gtgaacgagc ctgaggacgg agtgggcggc  1500
acgccggcga ggcgacgggg tactgcgccg ggagcttcgc gcacacgccg cacatggtcc  1560
ggcccgagga gatgaggaag ggacccggtca agacggtggc gaggttcggc gtgtgcgacc  1620
tgatggacga catcggggcg gacggcgacc agacggtggt cgtgtcgctc gtacccaggt  1680
gcggcggtga gctggtcacc gtcggcggcg tcagcatcag ctacgtcaag tga         1733
```

```
SEQ ID NO: 12          moltype = DNA  length = 1734
FEATURE                Location/Qualifiers
source                 1..1734
                       mol_type = other DNA
                       organism = synthetic construct
SEQUENCE: 12
atgtcacaga cccacagttc accattttac ctcctcgagt tcaccatgga gatcagcacg  60
agcgtgccac ggtgcaccgc caccccgggc gctcgcatgc cgtgcagcct ccaagccgtc  120
gtgcccacga aagcgaggca gccacggcac ctgtcgtgca aggcaacggg cggccgtgtc  180
gaccgccgtg acgtgctcct cggcatcggc agcgccgcgg cgaccgggct gggcaggcag  240
agaggccgag gggcgatcgc cgcgcccatc caggccccgg acctcggcaa ctgcaacccg  300
cccgacctcc cgaacacggc gccggacacc aactgctgcc cgacgtccgg caccgggatc  360
atcgacttcg tgctgccgcc ggcctcctcg gcgccgctcc gcgtgcgccc ggccgcgcac  420
ctggcggacg cggagtacct ggccaagtac gagcgggctg tggcgctcat gaagcagctg  480
cccgccgacg acccccgcag cttcgagcag cagtggcgcg tgcactgcgc ctactgcgac  540
ggcgcgtacg accaggtcgg cttcccggac ctggagatcc aggtgcacaa ctgctggctc  600
ttcttcccat ggcacaggtt ctacctctac ttccacgaga ggatcctcgg caagctcatc  660
ggcgacgaca ccttcgcgct gcccttctgg aactgggacg cgccggccgg catgacgctg  720
ccggcgatct acgccaacag gtcgtcgccg ctctacaatg agaggcgcga ccccgcccac  780
cagccgccgt tcccggtcga cctcgactac aacgagatag atgtcatcat cccaacagac  840
gagcagatcg accagaacct caacatcatg taccgccaga tggtgtcgag tgccaagaag  900
actcggctgt tcatggggca gccataccgc gccggcgacc agccggaccc gggagcgggc  960
```

tccctggaga acctgccgca caacacggtg cacatctgga cgggcgaccc ggcgcagccc 1020
aacagcgagg acatgggcaa cttctactcg gcggcgcgcg accccatctt cttcgcgcac 1080
cacggcaaca tcgaccgcct ctggcacgtc tggcgcggcc tccgccgggg caacgccaac 1140
ttcaccgacg ccgactggct tgacaccgcc ttcctcttct acgacgagga ggcccgcccc 1200
gtgcgcgtcc gcgtccgcga ctgcctcgac ccggccgcca tggggtactc ctaccaggac 1260
gtcggcctgc cgtggctgaa ggccaaaccg ggcaagagat cccgcaggac gccggcgccc 1320
gcggcgggcg cgctcccggc gacgctgagg gagaccgtgc gggtgacggt gacaaggccc 1380
caggtgtcga ggagcgacaa ggagaaggag gaggcggagg aggtgctgat catcgagggg 1440
atccaggtcg ccgaccactt caagttcgtc aagttcgacg tgctggtgaa cgcgcccgag 1500
agcggaggcg atgccgcgtc ggggtactgc gccggcagcg tcgcgatgac gccgcacatg 1560
gtccggacga acaagaagaa gggctccatg aagacggtgg cgaggttcgg cgtctgcgac 1620
ctgatggaca acatcggggc agacggcgac aagacggtcg tcgtgtcact cgtgccaagg 1680
tgcggcggcg agctggtcac cgtcggcggc gtcagcatcg gctataccaa gtga 1734

SEQ ID NO: 13 moltype = DNA length = 1734
FEATURE Location/Qualifiers
source 1..1734
mol_type = other DNA
organism = synthetic construct
SEQUENCE: 13
atggagagca ctcgcgtgct accgagtgcc aaccatcgca tgccatgcag cctccaaacc 60
tttccgcgac gcaacgttct ccgtgccctt caccgccgca aggacgcaag gcagccacgt 120
cgtatctcaa tctcatgcga ggcgaccggc ggcggtcgcg tcgaccgccg tgaggtgctc 180
ctcggcctcg gcggcgccgc agctgcgggg ctggccacgg accaaggtcg aggcgcgatc 240
gccgcgccca tccaggcccc ggacctccgc aactgccaaa cgcccgacct cccgaacacg 300
ccgccggaca ccaactgctg cccgacgccc ggcaccggca tcaccgactt tgagctgccg 360
cccgcttcct cgccgctccg cgtgcgtccg gcagcgcacc tggtggacgc ggagtacctg 420
gccaagtacg agagggccgt ggcgctcatg aagcagctgc ctgccgatga cccgcgcagc 480
ttcgagcagc agtggcacgt gcactgcgcc tactgcgacg ccgccttcga ccaggtcggg 540
ttcccggacc ttgagatcca ggtgcacaac tgctggctct tcttcccatg gcacaggttc 600
tacgtctact tccacgagag gatcctcggc aagctcatcg gcgacgacac cttcgcgctg 660
cccttctgga actgggacgc gccggccggc atgacgctgc cggcgatcta cgccaacagg 720
tcgtcgccgc tctacgacga gaggcgcgac cccgcccacc agccgccggt gctgaccgac 780
cttgactcca gtgggaccga cgccaatatc ccaagagacc agcagatcga tcagaacctc 840
aagatcatgt accgccagat gatttcggac gcgaagaaga cgctgctgtt cctgggacag 900
ccgtaccgcg ccggcgacca gccggacccg ggcgcgggct ccctggagaa cgtgccgcac 960
ggcacggtcc acgtctggac tggcgacccg gcgcagccga acttggagga catgggcaac 1020
ttcttctcgg cggcgcgcga ccccatcttc ttcgcgcacc acggcaacat cgaccgcctg 1080
tggcacgtct ggcgccgcct ccgcccgagc aacaccgact tcaccgaccc cgactggctc 1140
gacgccgcct tcctcttcta cgacgaggag gcccgccccg tgcgcgtgcg cgtccgggac 1200
tgcctcgacc cggccgcgct gcggtacacg taccaggacg tcggcctgcc gtggctcaac 1260
gccaggccgg ccaaggcgtc cggcgggacg ccggcgcccg ccacaaccgg taccctccct 1320
gccaccctgg acaggaccat acgggtgacg gtgacgaggc ccagagtgtc caggagccgc 1380
cgggagaagg aggaggagga ggaggtgctg gtcgtggagg ggatcgagat cgccgaccat 1440
ttcaacaagt tcgtcaagtt cgacgtgttg gtgaacgagc ccgagggcgg agtgggcagc 1500
acgccggcga cggcgacggg gtactgcgct gggagcttcg cgcatacgcc gcacatggtc 1560
cggcccgagg agatgaggaa gggaccggtc aagacggtgg cgaggttcgg cgtgtgcgac 1620
ctgatggacg acatcggggc ggacgacgac cagacggtgg tggtgtcgct cgtacccagg 1680
tgcggcggtg agctggtcac cgttggcggc gtcagcatca gctacctcaa gtga 1734

SEQ ID NO: 14 moltype = DNA length = 1719
FEATURE Location/Qualifiers
source 1..1719
mol_type = other DNA
organism = synthetic construct
SEQUENCE: 14
atgtcacaga ctcacagttc accattttac ctccccgagt tcaccatgga gatcagcacg 60
agcgtggcaa ggtgcactcg catgccgtgc agcctccaag ccctcgtgcc cacgaagctg 120
aggctgccac ggcgtctgac gtgcaaggca acgggcggcc gcgtcgaccg ccgtgacgtg 180
ctcctcggcc tcggcagcgc cgcggcggcc gggctgggca cgcagagagg ccgaggggcg 240
atcgccgcgc ccatccaggc cccggacctc ggcaactgca acccgcccga cctcccgaac 300
acggcgccgg acaccaactg ctgcccgacg tccggcaccg gcatcatcga tttcgtgctg 360
ccgccggcct cctcggcggc gctccgcgtg cgcccggccg cgcacctggc ggacgcggag 420
cacctggcca agtacgagcg ggccgtggcg ctcatgaagc agctgcccgc cgacgacccg 480
cgcagcttcg agcagcagtg gcgcgtgcac tgcgcctact gcgacggcgc gtacgaccag 540
gtcggtttcc cggacctgga gatccaggtg cacaactgct ggctcttctt cccatggcac 600
aggttctacc tctacttcca cgagaggatc ctcggcaagc tcatcggcga cgacaccttc 660
gcgctgccct tctggaactg ggacgcgccg gccggcatga cgctgccggc gatctacgcc 720
aacaggtcgt cgccgctcta caacgagagg cgcaaccccg cccaccagcc gccgttcccg 780
gtcgacctcg actacaacga gatagatgtc atcatcccaa cagacgagca gatcgaccag 840
aacctcaaca tcatgtaccg ccagatggtg tcgggtgcca agaagactag gctgttcatg 900
ggcagccgt accgcgccgg cgaccagccg gacccgggag cgggctccgt ggagaacgtg 960
ccgcacggca cgatgcacac ctggacgggc gacccggcgc agcccaacaa cgaggacatg 1020
ggcaacttct actcggcggc gcgcgacccc atcttcttcg cgcaccacgg caacatcgac 1080
cgcctctggc acgtctggcg cggcctccgc ccgagcaaca ccgacttcgc cgacgccgac 1140
tggcttgaca ccgccttcct cttctacgac gaggaggccc gccccgtgcg cgtccgcgtc 1200
cgcgactgcc tcgacccagc cgccatgggg tacgcctacc aggacgtcgg cctgccctgg 1260
ctgaaggcca agccggccaa gagatcccgc aggacgccgg cgcccgccgc gggcgcgctc 1320
ccggcgacgc tgagggagac cgtgcgggtg acggtgacaa ggccccaggt gtcgaggagc 1380

```
gacaaggaga aggaggaggc ggaggaggtg ctgatcatcg aggggatcca ggtcgccgac  1440
cacttcaagt tcgtcaagtt cgacgtgctg gtgaacgcgc ccgagagcgg aggcgatgcc  1500
gcgtcggggt actgtgccgg cagcgtcgcg atgacgccgc acatggtccg gacgaacaag  1560
aagaagggct ccatgaagac ggtggcgagg ttcggcgtct gcgacctgat ggacaacatc  1620
ggggcagacg gcgacaagac ggtggtcgtg tcgctcgtgc ccaggtgcgg cggcgagctg  1680
gtcaccatcg gcggcgtcag catcggctat accaagtga                         1719

SEQ ID NO: 15          moltype = AA  length = 577
FEATURE                Location/Qualifiers
source                 1..577
                       mol_type = protein
                       organism = Triticum aestivum
SEQUENCE: 15
MESSRMPLSA TPRMPCSLQT LARRNLLRGL HLRKDARQPR RLSVSCEATG GCRVDRREVL  60
LGLGGAAAAG LATDKGRGAI AAPIQAPDLR NCQTPELPNT PPDTNCCPTP GTGITDFVLP  120
PVSSPLRVRP AAHLVDAGYL AKYERAVALM KQLPADDPRS FEQQWHVHCA YCDAAYDQVG  180
FPDLELQIHN CWLFFPWHRF YLYFQERILG KLIGDDTFAL PFWNWDAPAG MTLPAIYADR  240
SSPLYDERRD PAHQPPVLVD LDSSGSDTNI PRDQQIDENL KIMYRQMISN AKKTLLFLGQ  300
PYRAGDQPDP GASSLENVPH GTVHVWTGDP RQPNLADMGN FFSAARDPIF FAHHGNMDRL  360
WHVWRGLRPS NTDFTDPDWL DAAFLFYDEE ARPVRVRVRD CLDPAALRYT YQDVGLPWLN  420
ARPAKASSGT PAPATTGTLP ATLDSTIRVT VTRPRVSRSR REKDEEEEVL VVEGIEIADH  480
FNKFIKFDVL VNEPEGGVDG TPATATGYCA GSFAHTPHMV RPEETRKGSV KTVARFGVCD  540
LMDDIGADGD QTVVVSLVPR CGGELVTVGG VSISYLK                          577

SEQ ID NO: 16          moltype = AA  length = 572
FEATURE                Location/Qualifiers
source                 1..572
                       mol_type = protein
                       organism = Triticum aestivum
SEQUENCE: 16
MSQTHSSPFY LLEFTMEIST SVARCTRMPC SLQALVPTKA RQTRRLTCKA TGGRVDRRDV  60
LLGLGSAAAA GLGAQRGRGA IAAPIQAPDL GNCNPPDLPN TAPDTNCCPT SGTGIIDFVL  120
PPASSAPLRV RPAAHLADAE YLAKYERAVA LMKQLPADDP RSFEQQWRVH CAYCDGAYDQ  180
VGFPDLEIQV HNCWLFFPWH RFYLYFHERI LGKLIGDDTF ALPFWNWDAP DGMTLPAIYA  240
NRSSPLYNER RNPAHQPPFP VDLDFNEIDV IIPTDEQIDQ NLNIMYRQMV SGAKKTRLFM  300
GQPYRAGDQP DPGAGSVENV PHGTMHTWTG DPAQPNNEDM GNFYSAARDP IFFAHHGNID  360
RLWHVWRGLR PGNADFTDTD WLDTAFLFYD EEARPVRVRV RDCLDPAAMG YAYQDVGLPW  420
LKAKPAKRSR RTPAPAAGAL PATLRETVRV TVTRPQVSRS DKEKEEAEEV LIVEGIQVAD  480
HFKFVKFDVL VNAPESGGDA ASGYCAGSVA MTPHMVRTNK KKGSVKTVAR FGVCDLMDNI  540
GADGDKTVVV SLVPRCGGEL VTIGGVSIGY TK                               572

SEQ ID NO: 17          moltype = AA  length = 577
FEATURE                Location/Qualifiers
source                 1..577
                       mol_type = protein
                       organism = Triticum aestivum
SEQUENCE: 17
MESTRMPLSA TPRMPCSLQT LARRNLLRAL HHRKDARQPR RLSISCEAAG GGSVDRREVL  60
LGLGSAAAAG LATDQGRGAI AAPIQAPDLR NCQTPALPNT PPDTNCCPTP GTSITDFELP  120
PASSPLRVRP AAHLVDAEYL AKYERAVALM KQLPADDPRS FEQQWHVHCA YCDAAFDQVG  180
FPDLELQIHN CWLFFPWHRF YVYFHERILG KLIGDDTFAL PFWNWDAPAG MTLPAIYANR  240
SSPLYDERRD PAHQPPVLVD LDSSGTDANI PRDQQIDENL KIMYRQMISN AKKTLLFLGQ  300
PYRAGDQPDP GAGSVENVPH GTVHGWTGDP RQPNGEDMGN FYSAARDPIF FAHHGNIDRL  360
WHVWRGLRPS NADFTDPDWL DAAFLFYDEE ARPVRVRVRD CLDTAALRYT YQDVGLPWLN  420
ARPAKASGGT PAPATTSTLP ATLDRTIRVT VTRPRVSRSR REKEDEEEVV VVEGIEIADH  480
FNKFIKFDVL VNEPEGGVGS TPATATGYCA GSFAHTPHMV RPEEMRKGPV KTVARFGVCD  540
LMDDIGADGD QTVVVSLVPR CGGELVTVGG VSISYVK                          577

SEQ ID NO: 18          moltype = AA  length = 524
FEATURE                Location/Qualifiers
source                 1..524
                       mol_type = protein
                       organism = Triticum aestivum
SEQUENCE: 18
MESTRVLPSA TPRMPGTLQT FPRRNVLRDL HHRKDARQPR RLSVSYEAAG GGRVDRREVL  60
LGLGSAAAAG LATDQGRGVI AAPIQAPDLR NCQTPALPNT PPDTNCCPTP STGITDFELP  120
PASSPLRVRP AAHLADAEYL AKYERAVALM KQLPANDPRS FEQQWHVHCA YCDAAFDQVG  180
FPDLELQIHN CWLFFPWHRF YVYFHERILG KLIGDDTFAL PFWNWDAPAG MTLPAIYANR  240
SSPLYDEMRD PAHQPPVLVD LDSSGTDANI PRDQQIDENL KIMYRQMISN AKKTLLFLGQ  300
PYRAGDQPDP GAVSVENVPH GTVHNWTGDP RQPNGEDMGN FYSAARDPIF FAHHGIIDRL  360
WHVWRGLRPS NTDFTDPDWL DAAFLFYDEE ARPVRVRVRD CLDPAALRYT YQDVGLPWLN  420
ARPAKASGGT PAPATTGTLP ATLDRTIRMT VTRPRVSRSR REKDEEEEVL VVEGIEIADH  480
FNKFIKFDVL VNEPEDGVGG TPARRRGTAP GASRTRRTWS GPRR                     524

SEQ ID NO: 19          moltype = AA  length = 577
FEATURE                Location/Qualifiers
source                 1..577
                       mol_type = protein
                       organism = Triticum aestivum
```

```
SEQUENCE: 19
MSQTHSSPFY LLEFTMEIST SVPRCTATPG ARMPCSLQAV VPTKARQPRH LSCKATGGRV  60
DRRDVLLGIG SAAATGLGRQ RGRGAIAAPI QAPDLGNCNP PDLPNTAPDT NCCPTSGTGI  120
IDFVLPPASS APLRVRPAAH LADAEYLAKY ERAVALMKQL PADDPRSFEQ QWRVHCAYCD  180
GAYDQVGFPD LEIQVHNCWL FFPWHRFYLY FHERILGKLI GDDTFALPFW NWDAPAGMTL  240
PAIYANRSSP LYNERRDPAH QPPFPVDLDY NEIDVIIPTD EQIDQNLNIM YRQMVSSAKK  300
TRLFMGQPYR AGDQPDPGAG SLENLPHNTV HIWTGDPAQP NSEDMGNFYS AARDPIFFAH  360
HGNIDRLWHV WRGLRRGNAN FTDADWLDTA FLFYDEEARP VRVRVRDCLD PAAMGYSYQD  420
VGLPWLKAKP GKRSRRTPAP AAGALPATLR ETVRVTVTRP QVSRSDKEKE EAEEVLIIEG  480
IQVADHFKFV KFDVLVNAPE SGGDAASGYC AGSVAMTPHM VRTNKKKGSM KTVARFGVCD  540
LMDNIGADGD KTVVVSLVPR CGGELVTVGG VSIGYTK                          577

SEQ ID NO: 20          moltype = AA  length = 577
FEATURE                Location/Qualifiers
source                 1..577
                       mol_type = protein
                       organism = Triticum aestivum
SEQUENCE: 20
MESTRVLPSA NHRMPCSLQT FPRRNVLRAL HRRKDARQPR RISISCEATG GGRVDRREVL  60
LGLGGAAAAG LATDQGRGAI AAPIQAPDLR NCQTPDLPNT PPDTNCCPTP GTGITDFELP  120
PASSPLRVRP AAHLVDAEYL AKYERAVALM KQLPADDPRS FEQQWHVHCA YCDAAFDQVG  180
FPDLEIQVHN CWLFFPWHRF YVYFHERILG KLIGDDTFAL PFWNWDAPAG MTLPAIYANR  240
SSPLYDERRD PAHQPPVLTD LDSSGTDANI PRDQQIDQNL KIMYRQMISD AKKTLLFLGQ  300
PYRAGDQPDP GAGSLENVPH GTVHVWTGDP AQPNLEDMGN FFSAARDPIF FAHHGNIDRL  360
WHVWRRLRPS NTDFTDPDWL DAAFLFYDEE ARPVRVRVRD CLDPAALRYT YQDVGLPWLN  420
ARPAKASGGT PAPATTGTLP ATLDRTIRVT VTRPRVSRSR REKEEEEEVL VVEGIEIADH  480
FNKFVKFDVL VNEPEGGVGS TPATATGYCA GSFAHTPHMV RPEEMRKGPV KTVARFGVCD  540
LMDDIGADDD QTVVVSLVPR CGGELVTVGG VSISYLK                          577

SEQ ID NO: 21          moltype = AA  length = 572
FEATURE                Location/Qualifiers
source                 1..572
                       mol_type = protein
                       organism = Triticum aestivum
SEQUENCE: 21
MSQTHSSPFY LPEFTMEIST SVARCTRMPC SLQALVPTKL RLPRRLTCKA TGGRVDRRDV  60
LLGLGSAAAA GLGTQRGRGA IAAPIQAPDL GNCNPPDLPN TAPDTNCCPT SGTGIIDFVL  120
PPASSAALRV RPAAHLADAE HLAKYERAVA LMKQLPADDP RSFEQQWRVH CAYCDGAYDQ  180
VGFPDLEIQV HNCWLFFPWH RFYLYFHERI LGKLIGDDTF ALPFWNWDAP AGMTLPAIYA  240
NRSSPLYNER RNPAHQPPFP VDLDYNEIDV IIPTDEQIDQ NLNIMYRQMV SGAKKTRLFM  300
GQPYRAGDQP DPGAGSVENV PHGTMHTWTG DPAQPNNEDM GNFYSAARDP IFFAHHGNID  360
RLWHVWRGLR PSNTDFADAD WLDTAFLFYD EEARPVRVRV RDCLDPAAMG YAYQDVGLPW  420
LKAKPAKRSR RTPAPAAGAL PATLRETVRV TVTRPQVSRS DKEKEEAEEV LIIEGIQVAD  480
HFKFVKFDVL VNAPESGGDA ASGYCAGSVA MTPHMVRTNK KKGSMKTVAR FGVCDLMDNI  540
GADGDKTVVV SLVPRCGGEL VTIGGVSIGY TK                               572

SEQ ID NO: 22          moltype = DNA  length = 3146
FEATURE                Location/Qualifiers
source                 1..3146
                       mol_type = genomic DNA
                       organism = Hordeum vulgare
SEQUENCE: 22
aaaatgcata tattgatttc taacatgtgt tcttttatca atcagaccta actgaaacac  60
atatggatgt aggtaaaatc agctaccgca catcaccgtg tcacctggaa aatacacttt  120
tgtttatggt tttatatact ccctatatgg gattattatt ttaataatta aaacagaagt  180
caaaatagtt aagaactatt tttagaaaag aaatgactta cttttgtgtt agtatataaa  240
ttttcaaaac aacaaaacca acgttgactt cacaacaaaa aaaacaaaat ttatttgcta  300
ttatagatca ctgttcaccc tatttaggtc aaagatttat ctttttcgaa aagaagtcaa  360
aggagatttt tcttttagtg aaatttttct tacaaataca aatgaaggtc aagtttattt  420
caaaaatatt tttagaattt ttgaactgtt tgttgaatta ctattttttt ctttctataa  480
ggtgtagacg tctccataca ccaaacgcac ccgcactaca tatagggacg gttgcctcaa  540
agttcactgc atcctgtgta tccgtatgcg ggcagcagcc agaaagcaaa cagcggcagc  600
atggagagca ctcgcatgat actgagtgtc acccctagca tgccatgcgg cctccaaacc  660
cttgcgcgcc gcaaccttgt ccgtgccctc caccaccgca aggacgcgag gcagccacgc  720
cgtctctcat gcgaggcaac tggcggccgc cgcgtcgatc ggcgtgacgt gcttctcggc  780
ctcggcggcg ccgccgcggc cgggctgggc gcccagcggg acgcgctcgc cgcgcccatc  840
caggcccccg acttcctcaa ctgcaacccg cccgacctcc cgaacacgcc gccggacgcc  900
agctgctgtc cgccgtaccg cgacggcacc attatcaccg acttcaggcc gccgcccgcc  960
tcctcgccgc tccgcgtgcg tccggcggcg cacctggtgg acgcggagtc cctggccaag  1020
tacgagaggg ccgtggcgct catgaagcag ctcccggccg atgacccccg cagcttcgag  1080
cagcagtggc gcgtgcactg cgcctactgc ggcgccgtgt tcgaccaggt cggcttcccg  1140
gacctggaga tccagataca cttctgctgg ctcttcttcc catggcacag gtaggtgctg  1200
ctgcctggta gtggtcctcc tgccgcacct ttttgtgcgc catagaacct gaacgagccg  1260
cgtgcctttg ttgaatggac gtgcaggttg tacctctact ttcacgagag gatcctcggc  1320
aagctcatcg gcgacgacac cttcgccctg ccgttctgga actgggacgc gccggacggc  1380
atgtcactgc cggcgatcta cgccaacggg tcgtcgccgc tctacaacga gaggcgtgac  1440
cccgcccacc agccgccatt cccgctcgac ctcgactaca gcgacaccga cgccaatatc  1500
tcaagagacc agctgatcga ccagaacctc aagatcatgt accgccaggc cagtagtact  1560
aattaacaag ctcaagaatc cctcacaaaa aattactagc aacttcaaaa atattccttg  1620
```

```
ttaacctaac cgcgtggtca ttaaataaca caaatgttcg tacgcatcag atggtttcgg  1680
acgcgaagaa gagggagctg ttcctggggc agccgtaccg cgccggcgac cagccggaca  1740
caggtgcggg ctccgtggag aacgtgccgc acggcccggt ccaccgctgg acgggcgacc  1800
cggcgcagcc caaccgcgag gacatgggca acttctactc ggcggcgcgc gaccccatct  1860
tcttcgcgca ccacggcaac atagaccgcc tctggcatgt ctggcgcggc ctccgcccga  1920
gcaacaccga cttcaccgac cccgactggc tcgacgccgc cttcctcttc tacgacgagg  1980
aggcccgcct cgtgcgcgtc cgcgtccgcg actgcctcga tacggccgca ctgcggtaca  2040
cgtaccagga cgtcggcctg ccgtggctca acgccaggcc agccaaggcg tccgccggga  2100
cgccagcgcc ggccaccacc ggtaccctcc ctgccaccct ggacaggacc atccgggtga  2160
cggtgacgag gcccagggtg tcgaggagcc gccgggagaa ggacgaggag gaggaggtgc  2220
tggtcgtgga ggggatccag atcgccgacc atttcaacga gttcgtcaag ttcgacgtgc  2280
tggtgaacga gcccgaacgc gcagtgggcg gcacgccggc gacggcgacg gggtactgcg  2340
ccgggagctt cgcgtacacg ccgcacatgg cccggtcaga cgagatgagg aacgggccgg  2400
tgaagacggt ggcgaggttc ggcgtgtgcg acctgatgga cgacatcggc gcggatggcg  2460
acaagacggt ggtcgtgtcg ctggtgccga ggtgcgggtg cgagatggtc accgtcggcg  2520
gcgtcagcat cagctacctc aagtgactgt ccggcgaagc aagcacccat ctgcgctagc  2580
gtcggcgttc actgtggtat ggaatctatg gcacctctcc tcgtattgta ttgcagcacg  2640
cgtacgtacg tgcgtatgtc ctatgtgtaa tgtaaatgat ggtgattcta aataaaaaca  2700
gctcaagtaa atggaaatgg tggaacgttg tcctggaact taggtgttta ggacgtagtg  2760
tgacgttgta ttatgttctg tcaatgtatt ctttcgatag catagtcgct tatgttctat  2820
gtgttccgct tatcttgaga tccgcattct acgaggttac ctcaccttct tgatcgttca  2880
cttgttgtgg ttgttgcttc atacataaag cgggatgact ctctgttttg agaaagaaag  2940
taaatgggat tatgggtctc gctgcgtctg tcctatactc tacatatgta tttaattatg  3000
tgcgcgatac catactaatt agtttttgg atttgctaaa tctcaatgcc tcaaaacaaa  3060
agttggataa tcgattttac atatgagaag gagaggagag acgacgttga gtcagagatg  3120
gtcgtgcccc gacgagcgct aactca                                        3146

SEQ ID NO: 23          moltype = DNA  length = 3434
FEATURE                Location/Qualifiers
source                 1..3434
                       mol_type = genomic DNA
                       organism = Hordeum vulgare
SEQUENCE: 23
ccgcaccgtt ttccataccg ccgacaccct acacccgaac cactcaactc tgtgttgttg  60
ccggcgccga ctcgtttctg gcgagacatc agcgaagacg tcgtgacgta cccgactcag  120
cctcggggcc gtgcttcgct ggaattcaac tgatgcgtct aaaaatacag gtggctgcgt  180
attatcaaac ggtaggctca aatacatgta cacatgtcac agtacactgt tgagctgtct  240
atgcagtgaa ccaaaattgt caaagcactc tactgtacta cacgtagctg cttgatgtgc  300
atgtcacgat cccctttaag atccaaaatg gtttgccacg tttgatagat agataagcac  360
tttcccgtgg atcaacttaa gcaagtaact ttcctctcgc gagctgcgcg cgttagtcct  420
cgcctcgcca tccaacctcg aggaacagtg accaacagtt gaaatgcagt tcaaccatca  480
cacgtaacca acggtcaaac caaattactt agctgcgagc cctgctgcac gcgcgtgcac  540
ggagtgccac gcacggcacc gctacagtac atataccacc atgcggagcg gtgcaagtgc  600
aacacatgtc acagttcacc atggagatga gcatcacgag cgcgccaagg tgcaccacca  660
ccctcggcac tcgcatgccg agcaacctcc aggccctcgt gcccaagggg catgctcatg  720
ccctcctccg cgatcgcaag gaagcgaggc agccgcggcg tctggcgtgc aaggcaaccg  780
gcggccgcgt cgaccgccgt gacgtgctcc tcggcctcgg cagcgccgcg gcggccgggc  840
tgggcacgcg gcgaggccga ggggcgatcg ccgcgcccat ccaggccccg gacctcggca  900
actgcaaccc gcccgagctc ccgaacacgg cgccggacac caactgctgc ccgacgtccg  960
gcaccgggat caccgacttc gtgctaccgc cggcggcctc ctcggcgccg ctccgggtgc  1020
gcccggccgc gcacctggtg gacgcggggc acctggccaa gtatgagcgc gccgtggcgc  1080
tcatgaagca gctgcccgcc gacgacccgc gcagcttcga gcagcagtgg cgcgtgcact  1140
gcgcctactg cgacggcgcc tacgaccagg ccggcttccc ggacctggag atccaggtgc  1200
acaactgctg gctcttcttc ccgtggcaca ggtacgtata caagtactag tacacaatac  1260
gaatagtaca tgtgttttta tacacatgca tgcatgtcca tttttgtcag ctttgcaatt  1320
ggtcgccatg actgcatgag tagcggcctg cacctttcgt acagtgcgcg agctgaacgt  1380
gccgtcaact tgtcaccatg tttgactatt ttggtgctgc gtatacgtac gtgcaggttc  1440
tacctctact tccacgagag gatcctcggc aagctcatcg gcgacgacac cttcacgctg  1500
cccttttgga actgggacgc gccgggagga atgacggtgc cggcgatgta cgccaacacg  1560
tcgtcgcctc tctacaacca gaggcgcgac cccgcccacc agccgccgtt cccggtcgac  1620
ctcgactaca acgaggtcga cgtcgtcgtc ccaacagacg agcagatcga ccagaacctc  1680
aggatcatgt accgccaggt cagtacaact aacatacacg attgcacaca cagtaccaaa  1740
gttatcacgt tgacatatca aatgtgtgtg cgtgtgtgtg tgcatcagat ggtgtcgagt  1800
gccaagaaga cccagctgtt catggggcag ccgtaccgcg ccggcgacca gccggacccg  1860
ggagcgggct ccatggagaa cgtgccgcac ggcacggtgc acacctggac gggcgacccg  1920
gcgcagccca acggcgagga catgggcaac ttctactcgg cggcgcgcga ccccatcttc  1980
ttcgcgcacc acgccaacat cgaccgcctg tggcacgtct ggcgcggcct ccgccccggc  2040
aacgccgact ttgccgacgc cgactggctc gacgccgcct tcctcttcta cgacgaggag  2100
gcccgcctcg tgcgtgtccg cgtccgcgac tgcctcgacc tggccgccat ggggtacgcg  2160
taccaggacg tcggcctgcc gtggctggag gccaagccgg ccaagagatc cggtgcgacg  2220
ccggcgcccg ccgcaggcgc gctcccggcc acgctggggg agaccgtgcg ggtgacggtg  2280
acgaggcccc aggtgtcgag gagcagcaag gagaaggagg aggcggagga ggtgctgatc  2340
atcgagggga tcgaggtcgc cgaccatttc aacaagttca tcaagttcga cgtgctggtg  2400
aacgagcccg agagcggagg cgacggcgcg tcggggtact gcgccggcag cgtcgcgctg  2460
acgccgcaca tggtccggac caacgagaag aagggctccg tgaagacggt ggcgaggttc  2520
ggcgtctgcg acctgatgga caacatcgga gccgacggtg acaagacggt ggtcgtgtcg  2580
ctcgtgccca ggtgcggcgg cgagctggtc accgtcggcg gcgtcagcgt cggctatgcc  2640
aagtgaagca ccgccaccgt atatatatac cgtgtgctgc atacctatag acaagctgct  2700
aatgagcgat cgttgcgtgc tttacatgca tgcatctagt gtgcttatat tgcacggtat  2760
```

```
gtacgttgcg tatgtctagt atatttatat gtaatgatta taatggacgg tgtgttttta  2820
gaatcggatt tcacccctat ttatacataa ataaaactgt atataaatta ttgaaacccc  2880
gaatgtttcg ttgttcttgt gttgtatact tgtattaatc tggccttcac agcatccgcg  2940
taaaattctt cggtatctca tgtataaggc atgcacgtag ttttatgtcg ttaatttaat  3000
tacttaggct tgccatagtg gggtatcat agttagtaat atagtattga gactagcaaa  3060
catgatgatg tggcaagtaa ttaaagaaga gagagggtta tatacagtaa cataggtact  3120
gtagataccg tatcatgtta aatgctatgc tactactata tgtgtcacac atgtcaataa  3180
atgaaaacac ctatgatact atgcactatg aaggtagtat catacaatag taacatatgc  3240
atgatactac tatatgttac tccccactat aagcagcctt aaatatgtat tatatgtaat  3300
aaataatata tcattagatt catgtggtga tgtagtttct aaatatgtaa tttgtatcgc  3360
atataaatata tatttagcta gttaaattaa caacctaaaa ctacgcgcat gccctataca  3420
attggacgga ggta                                                    3434

SEQ ID NO: 24          moltype = DNA  length = 1728
FEATURE                Location/Qualifiers
source                 1..1728
                       mol_type = other DNA
                       organism = synthetic construct
SEQUENCE: 24
atggagagca ctcgcatgat actgagtgtc accccctagca tgccatgcgg cctccaaacc  60
cttgcgcgcc gcaaccttgt ccgtgccctc caccaccgca aggacgcgag gcagccacgc  120
cgtctctcat gcgaggcaac tggcggccgc cgcgtcgatc ggcgtgacgt gcttctcggc  180
ctcggcggcg ccgccgcggc cgggctgggc gcccagcggg acgcgctcgc cgcgcccatc  240
caggcccccg acttcctcaa ctgcaacccg cccgacctcc cgaacacgcc gccggacgcc  300
agctgctgtc cgccgtaccg cgacggcacc attatcaccg acttcaggcc gccgcccgcc  360
tcctcgccgc tccgcgtgcg tccggcggcg cacctggtgg acgcggagtc cctggccaag  420
tacgagaggg ccgtggcgct catgaagcag ctccccgccg atgacccccg cagcttcgag  480
cagcagtggc gcgtgcactg cgcctactgc ggcgccgtgt tcgaccaggt cggcttcccg  540
gacctggaga tccagataca cttctgctgg ctcttcttcc catggcacag gttgtacctc  600
tactttcacg agaggatcct cggcaagctc atcggcgacg acaccttcgc cctgccgttc  660
tggaactggg acgcgccgga cggcatgtca ctgccggcga tctacgccaa cgggtcgtcg  720
ccgctctaca acgagaggcg tgaccccgcc caccagccgc cattcccgct cgacctcgac  780
tacagcgaca ccgacgccaa tatctcaaga gaccagctga tcgaccagaa cctcaagatc  840
atgtaccgcc agatggtttc ggacgcgaag aagagggagc tgttcctggg gcagccgtac  900
cgcgccggcg accagccgga cacaggtgcg ggctccgtgg agaacgtgcc gcacggcccg  960
gtccaccgct ggacgggcga cccggcgcag cccaaccgcg aggacatggg caacttctac  1020
tcggcggcgc gcgaccccat cttcttcgcg caccacggca acatagaccg cctctggcat  1080
gtctggcgcg gcctccgccc gagcaacacc gacttcaccg accccgactg gctcgacgcc  1140
gccttcctct tctacgacga ggaggcccgc ctcgtgcgcg tccgcgtccg cgactgcctc  1200
gatacggccg cactgcggta cacgtaccag gacgtcggcc tgccgtggct caacgccagg  1260
ccagccaagg cgtccgccgg gacgccagcg ccggccacca ccggtaccct ccctgccacc  1320
ctggacagga ccatccgggt gacggtgacg aggcccaggg tgtcgaggag ccgccgggag  1380
aaggacgagg aggaggaggt gctggtcgtg gaggggatcc agatcgccga ccatttcaac  1440
gagttcgtca agttcgacgt gctggtgaac gagcccgaac gcgcagtggg cggcacgccg  1500
gcgacggcga cggggtactg cgccgggagc ttcgcgtaca cgccgcacat ggcccggtca  1560
gacgagatga ggaacgggcc ggtgaagacg gtggcgaggt tcggcgtgtg cgacctgatg  1620
gacgacatcg gcgcggatgg cgacaagacg gtggtcgtgt cgctggtgcc gaggtgcggg  1680
tgcgagatgg tcaccgtcgg cggcgtcagc atcagctacc tcaagtga               1728

SEQ ID NO: 25          moltype = DNA  length = 1746
FEATURE                Location/Qualifiers
source                 1..1746
                       mol_type = other DNA
                       organism = synthetic construct
SEQUENCE: 25
atgtcacagt tcaccatgga gatgagcatc acgagcgcgc caaggtgcac caccaccctc  60
ggcactcgca tgccgagcaa cctccaggcc ctcgtgccca aggggcatgc tcatgccctc  120
ctccgcgatc gcaaggaagc gaggcagccg cggcgtctgg cgtgcaaggc aaccggcggc  180
cgcgtcgacc gccgtgacgt gctcctcggc ctcggcagcg ccgcggcggc cgggctgggc  240
acgcggcgag gccgaggggc gatcgccgcg cccatccagg ccccggacct cggcaactgc  300
aacccgcccg agctcccgaa cacggcgccg gacaccaact gctgcccgac gtccggcacc  360
gggatcaccg acttcgtgct accgccggcg gcctcctcgg cgccgctccg ggtgcgcccg  420
gccgcgcacc tggtggacgc ggggcacctg gccaagtatg agcgcgccgt ggcgctcatg  480
aagcagctgc ccgccgacga cccgcgcagc ttcgagcagc agtggcgcgt gcactgcgcc  540
tactgcgacg gcgcctacga ccaggccggc ttcccggacc tggagatcca ggtgcacaac  600
tgctggctct tcttcccgtg gcacaggttc tacctctact tccacgagag gatcctcggc  660
aagctcatcg gcgacgacac cttcacgctg cccttttgga actgggacgc gccgggagga  720
atgacggtgc cggcgatgta cgccaacacg tcgtcgcctc tctacaacca gaggcgcgac  780
cccgcccacc agccgccgtt cccggtcgac ctcgactaca acgaggtcga cgtcgtcgtc  840
ccaacagacg agcagatcga ccagaacctc aggatcatgt accgccagat ggtgtcgagt  900
gccaagaaga cccagctgtt catggggcag ccgtaccgcg ccggcgacca gccggacccg  960
ggagcgggct ccatggagaa cgtgccgcac ggcacggtgc acacctggac gggcgacccg  1020
gcgcagccca acggcgagga catgggcaac ttctactcgg cggcgcgcga ccccatcttc  1080
ttcgcgcacc acgccaacat cgaccgcctg tggcacgtct ggcgcggcct ccgccccggc  1140
aacgccgact ttgccgacgc cgactggctc gacgccgcct tcctcttcta cgacgaggag  1200
gcccgcctcg tgcgtgtccg cgtccgcgac tgcctcgacc tggccgccat ggggtacgcg  1260
taccaggacg tcggcctgcc gtggctggag gccaagccgg ccaagagatc cggtgcgacg  1320
ccggcgcccg ccgcaggcgc gctcccggcc acgctggggg agaccgtgcg ggtgacggtg  1380
acgaggcccc aggtgtcgag gagcagcaag gagaaggagg aggcggagga ggtgctgatc  1440
```

```
atcgagggga tcgaggtcgc cgaccatttc aacaagttca tcaagttcga cgtgctggtg  1500
aacgagcccg agagcggagg cgacggcgcg tcggggtact gcgccggcag cgtcgcgctg  1560
acgccgcaca tggtccggac caacgagaag aagggctccg tgaagacggt ggcgaggttc  1620
ggcgtctgcg acctgatgga caacatcgga gccgacggtg acaagacggt ggtcgtgtcg  1680
ctcgtgccca ggtgcggcgg cgagctggtc accgtcggcg gcgtcagcgt cggctatgcc  1740
aagtga                                                             1746

SEQ ID NO: 26          moltype = AA  length = 575
FEATURE                Location/Qualifiers
source                 1..575
                       mol_type = protein
                       organism = Hordeum vulgare
SEQUENCE: 26
MESTRMILSV TPSMPCGLQT LARRNLVRAL HHRKDARQPR RLSCEATGGR RVDRRDVLLG  60
LGGAAAAGLG AQRDALAAPI QAPDFLNCNP PDLPNTPPDA SCCPPYRDGT IITDFRPPPA  120
SSPLRVRPAA HLVDAESLAK YERAVALMKQ LPADDPRSFE QQWRVHCAYC GAVFDQVGFP  180
DLEIQIHFCW LFFPWHRLYL YFHERILGKL IGDDTFALPF WNWDAPDGMS LPAIYANGSS  240
PLYNERRDPA HQPPFPLDLD YSDTDANISR DQLIDQNLKI MYRQMVSDAK KRELFLGQPY  300
RAGDQPDTGA GSVENVPHGP VHRWTGDPAQ PNREDMGNFY SAARDPIFFA HHGNIDRLWH  360
VWRGLRPSNT DFTDPDWLDA AFLFYDEEAR LVRVRVRDCL DTAALRYTYQ DVGLPWLNAR  420
PAKASAGTPA PATTGTLPAT LDRTIRVTVT RPRVSRSRRE KDEEEEVLVV EGIQIADHFN  480
EFVKFDVLVN EPERAVGGTP ATATGYCAGS FAYTPHMARS DEMRNGPVKT VARFGVCDLM  540
DDIGADGDKT VVVSLVPRCG CEMVTVGGVS ISYLK                             575

SEQ ID NO: 27          moltype = AA  length = 581
FEATURE                Location/Qualifiers
source                 1..581
                       mol_type = protein
                       organism = Hordeum vulgare
SEQUENCE: 27
MSQFTMEMSI TSAPRCTTTL GTRMPSNLQA LVPKGHAHAL LRDRKEARQP RRLACKATGG  60
RVDRRDVLLG LGSAAAAGLG TRRGRGAIAA PIQAPDLGNC NPPELPNTAP DTNCCPTSGT  120
GITDFVLPPA ASSAPLRVRP AAHLVDAGHL AKYERAVALM KQLPADDPRS FEQQWRVHCA  180
YCDGAYDQAG FPDLEIQVHN CWLFFPWHRF YLYFHERILG KLIGDDTFTL PFWNWDAPGG  240
MTVPAMYANT SSPLYNQRRD PAHQPPFPVD LDYNEVDVVV PTDEQIDQNL RIMYRQMVSS  300
AKKTQLFMGQ PYRAGDQPDP GAGSMENVPH GTVHTWTGDP AQPNGEDMGN FYSAARDPIF  360
FAHHANIDRL WHVWRGLRPG NADFADADWL DAAFLFYDEE ARLVRVRVRD CLDLAAMGYA  420
YQDVGLPWLE AKPAKRSGAT PAPAAGALPA TLGETVRVTV TRPQVSRSSK EKEEAEEVLI  480
IEGIEVADHF NKFIKFDVLV NEPESGGDGA SGYCAGSVAL TPHMVRTNEK KGSVKTVARF  540
GVCDLMDNIG ADGDKTVVVS LVPRCGGELV TVGGVSVGYA K                      581

SEQ ID NO: 28          moltype = DNA  length = 3209
FEATURE                Location/Qualifiers
source                 1..3209
                       mol_type = genomic DNA
                       organism = Secale cereale
SEQUENCE: 28
acgacttccc gactgtatac tacaacaagg tgtgcccgac ttcgacgatg gaggggtgat  60
gacggcggcg cgccttcggc tcgcttcatt gcttgtagtc gtcgctaggt ggtctacgga  120
tctggatgta atttttattt ctggtgttcg ttgtactgcc atgattgaag attaatagat  180
tggaagtttt aaaaaaaaaa tctggttctc tacaaactcg gtatccaaac aaatatgcag  240
tgaaccagaa ttgtcaagca ctctactgta ctatacgtag ctgcttagtg tgcatgtcac  300
gatccgcttt aagatcctgt ggtttgtcgc gtttcatacg taagcacttt accgtgtatc  360
aacttaggta acttgcgaat cgtgaacggc actttagtcc attgccatcc aacctcgagg  420
aacagtgacc accagttgta acgcagttca accatcacac gtaaccaaca gtccaaccga  480
acagctgcga gccctgccgc acgtgcacga agtggcacgc actactacat ataccaccac  540
catacggagc ggtgcaacac atttcacagt taaccatttt acctcctcga cgagttcacc  600
atggagatca gcaggagcgt gccaaggtgc accaccacca cccctggcgc tcgcatgcca  660
tgcagcctcc aagccctcgt gcccacgaaa gcgaggcagc cacggcgtct gacgtgcaag  720
gcaacgggcc gccgcgtcga ccgccgtgac gtgctcctcg gcctcggcag cgccgcggcg  780
gccgggctgg gcacgcggcg aggccgaggg gcgatcgcgg cgcccatcca ggcgccggac  840
ctcggcaact gccacccgcc cgacctcccg aacacggcgc cggacaccaa ctgctgcccg  900
acgtccggca ccgggatcgc cgacttcgtg ctgccgccgg cctcctcggc gccgctccgc  960
gtgcgcccgg ccgcgcacct ggtggacgcg gagcacctgg ccaagtacga gcgggccgtg  1020
gcgctcatga agcagctgcc cgccgacgac ccgcgcagct tcgagcagca gtggcgcgtg  1080
cactgcgcct actgcgacgg cgcgtacgac caggtcgggt tcccggacct ggagatccag  1140
gtgcacaact gctggctctt cttcccatgg cacaggtacg tagcgtagta cttcaacata  1200
aatacgtgtt gcttacacac atgcatgcat gtccagtttt gtcagcttag taattgctcg  1260
tttgggtcgg gtgtgcagta agcatgactg catgagtacg tgtggttagc ggcctgcgcc  1320
tttcgtacag tgcgccagct gaacgtgccg tcaactgtca ctttgtttaa cttgtttggt  1380
gctgcgtacg cgcaggttct acctctactt ccacgagagg atcctcggca agctcatcgg  1440
cgacgacacc ttcacgcttc cgttctggaa ctgggacgcg ccggccggca tgacgctgcc  1500
ggcgatctac gccagcacgt cgtcgcctct ctacaacgag aggcgcgacc ccgcccacca  1560
gccgcctttc ccgatcgacc ttgactacaa cgggaccgac gtcatcgtcc caacagacga  1620
gcagatcgac cagaacctca ggatcatgta ccgccaggca agtacaacca atacaaaatt  1680
acgtacgcgc agcaccaaaa atctctgaaa gctatcacct tgacatacca tatcaatctg  1740
tgtgcatcga tcagatggtg tcgagtgcca agaagactcg gctgttcatg gggcagccgt  1800
accgcgccgg cgaccagccg gacccgggag cgggctccgt ggagaacttg ccgcacggca  1860
cggtgcaccg ctggacgggc gacccggcgc agcccaacgg cgaggacatg ggcaacttct  1920
```

```
actcggcggc gcgcgacctc atcttcttcg cgcaccacgg caacatcgac cgcctgtggc  1980
acgtctggcg cggcctccgc cccgccaacg ccgacttcgc cgacgccgac tggcttgaca  2040
ccgccttcct cttctacgac gaggaagccc gccccgtccg tgtccgtgtc cgcgactgcc  2100
tcgacacggc cgccatgggg tacgcgtacc aggacgtcga cctgccctgg ctggacgcta  2160
agcctgccaa gaaatcggcc gggacgccgg tgccggcagc gggcgcgctc ccggccacgc  2220
tgggggagac cgtgcgggtg acggtgacga ggccccaggt gtcaaggagc agcaaggaga  2280
aggaggaggc ggaggaggtg ctgatcatcg aggggatcga ggtcgccgac cacttcaagt  2340
tcgtcaagtt cgacgtgctg gtgaacgagc ccgagagcgg aggcgacggc gcgtctgggt  2400
actgcgccgg cagcgtcgcg ctgacgccgc acatggtgcg gacgaacaag aagaagggct  2460
ccgtgaagac ggtggcgagg ttcggcgtct gcgacctgat ggacaacatc ggagccgacg  2520
gtgacaagac ggtggtggtg tcgctcgtgc ccaggtgcgg cggcgagctg gtcaccgtcg  2580
gcggcgtcag catcggctat gtcaagtgaa gcaccgccac cgtatatacc gtgagatgta  2640
tagctagaca agctgctcat gagcgatcgt tgcgtgcttt acatgcatct actgcgccac  2700
cgttgcgtgc tttatatgta cgtgagtatg tctagcgtat tttaaataag gaagaaaaat  2760
atacggagta actgaaaaat tgcagcgtat actgcactgt atctacgttg cgtgctataa  2820
atggtgtggc taggtgactg agacttcatc ggttcgtccc cgcaaaaaaa taaaaaaggt  2880
gactgagact tcacattaca tgtaagaaag aaaaaagaat gactaaaaca aaattatgcg  2940
gatctcaatg tatgatctca caaatatagc atcgactaac acataattaa atttcagttg  3000
actaagattt agcatgactg aaataagaat aattggaata attgaaattt ggagcggtgc  3060
acccatttte ctaacttata tacacagggt tttatttata gaaaagacta tttttttctt  3120
ctttaactct tcggaaagtc tatatttggt catgcaattc tcaaacctgg cattttgcac  3180
actcaacttt ccaaaccaaa caaacagaa                                    3209
```

```
SEQ ID NO: 29          moltype = DNA  length = 3152
FEATURE                Location/Qualifiers
source                 1..3152
                       mol_type = genomic DNA
                       organism = Secale cereale
SEQUENCE: 29
cttacctatt caaagcaatt cacctaggga tttttttta cagaatatat aatttcctgc  60
tatggagccc gcaaaggggt tattgatacc gtcgtacgaa cagcaggtgg tggatatctt  120
acatgtagac ttgttgatgt ttttccacat attattgtgt gtagaagata ttgtgatact  180
atcgaggtat ttatataagt ccaaaaacac gttgacaact tgccaacaaa ctgaaatatg  240
agtttcaacg ttcaccatcg atcactggaa acttataacc atcacacgcg cgtcgagaac  300
aatcaaatca aggaactggc tatccaccat cgtctcaaaa tttattttga gcttccttgt  360
acaaaatgga tttgcccaaa ttacaaattc aatcaactta catatagcta ccgtgtcagc  420
gcatggcaca tatggttagc aagatcacag ttcgcatatg cctgccgtgt caaaccaaac  480
agcggctgta cacggtatat gcccggtgca cacgcactac atatagggac ggttggctcg  540
agctcaccac gtcctgttta cccgtaagcg ggcggcagcc agaaagcaaa caccggcagc  600
atggagagca gtcgcatgcc actgagtgcc acccctcgca tgccatgcag cctccaaacc  660
attgcgcgcc gcaaccttct ccgtgccctt caccgccgca aggacgcgag gcagccacgg  720
cgtctcccaa tctcatgcga ggcgaccggc ggcggctgcg tcgaccgccg tgaggtgctc  780
gtcggcctcg gcggcgccgc agctgccggg ctggtcacgg accaaggtcg aggcgccatc  840
gcagcgccca tccaggcccc ggacctccgc aactgccaaa cgcccgacct cccggacacg  900
gcgccggaca ccaactgctg cccgacgccc ggcaccggca tcaccgactt ccagctgccg  960
cccgccacct cgccgctccg cgtgcgtccg gcagcgcacc tggtggacgc ggaatacctg  1020
gccaagtacg agagagccgt ggcgctcatg aagcagctgc ccgccgacga cccgcgcagc  1080
ttcgagcagc agtggcacgt gcactgcgcc tactgcgacg ccgccttcga ccaggtcggg  1140
ttcccggacc tggagctcca gatacacaac tgctggctct tcttcccatg gcacaggttc  1200
gtatggtcaa tgggttatgt ggtgtgacgg cctgcacctc tctgtgctgg agccttcatt  1260
tgtccctgcg tgcgtgtgct caacgtgcag gttctacctg tacttccacg agaggatcct  1320
cggcaagctc atcggcgacg acaccttcgc gctgcccttc tggaactggg acgcgccggc  1380
cggcatgacg ctgccggcga tctacgccaa caggtcgtcg ccgctctacg acgagaggcg  1440
cgaccccgcc caccagccgc cggtgctgat cgaccttgac tccagtggga ccgacgccag  1500
tatcccaaga aaccagcaga tcgatcagaa cctcaagatc atgtaccgcc aggccagtag  1560
tactaattaa caacttcaag aatccctaga aaaaatgagt agcaacttca aaaatattgt  1620
taaggtaacc acagaaccac tggtcattaa ataacacaaa tgcacgtacg caccagatga  1680
tttcggacgc gaagaagacg ctgctgttcc tgggacagcc gtaccgcgcc ggcgaccagc  1740
cggacccggg cgcgggctcc gtggagaacg tgccgcacgg cacggtccac gtctggacag  1800
gcgacccaag gcagcccaac ggcgaggaca tgggcaactt ctactcggcg gcgcgcgacc  1860
ccatcttctt cgcgcaccac ggcaacatcg accgcctctg gcacgtctgg cgcggcctcc  1920
gcccgagcaa caccgacttc accgaccccg actggctcga cgccgccttc ctcttctacg  1980
acgaggaggc ccgccccgtg cgcgtgcgcg tccgggactg cctcgacacg gccgggctgc  2040
ggtacacgta ccaggacgtc ggcctgccgt ggctcaacgc caggccagcc aaggcgtcga  2100
ccggcacgcc ggcgcccgcc accaccagta ccctgccagc caccctggac aggaccatac  2160
gggtgacggt gacgaggccc agggtgtcga ggagccgccg ggagaaggac gaggaggagg  2220
aggtgctggt cgtggagggg atcgagatcg ccgaccgttt caacaagttc gtcaagttcg  2280
acgtgctggt gaacgagccc gagggcggag tgggtggcat gccggcggtg gcgacggggt  2340
actgcgctgg gagcttcgcg cacacgccgc acatgatccg gcccgacgag atgaggaagg  2400
ggtcggtcaa gacggtggcg aggttcggcg tgtgcgacct gatggacgac atcggggcgg  2460
acggagacaa gacggtggtc gtttcgctgg tgccgaggtc cggcggcgag ctggtcaccg  2520
tcggcggcgt cagcatcagc tacctcaagt gactttcggc gaagcaagca cccatctgct  2580
ctggcgtcgg tgttcaccgt ggtgtagaat tagcatctac ggcgcgtctc ctcgtattgt  2640
atcgcagcac gtactgagta agtatttggg tatgtcctat gtctatgtgt aatggtgatg  2700
attgaattat aaataagaac aaccgaaatt aaataattag ggaaaagtat attttttgtc  2760
cctgaactct cttgaaggta tagaaattat ccctcaactt tgaaaccagc aaaactaagt  2820
cccccaactt atcaaaccgg attagtttag tccctctgct cacttgaagt ggtttttgag  2880
ttgacgtggc ctggttttga cctctctttg tccacgtggc aatattactg tttcatttct  2940
tcttatcatt ggtgtagcca ttttgtcgag cacatggtgt gcggtgtcag ccgctcccgg  3000
```

```
cagcatgcct ccgtcctgag gttgagcgat tcagagcttg tgacggcggc gagcagaagg  3060
cagtaacgag ggatcgtcgg gtggcataga tcgagtggca gcggcatcgg ggtcgaactc  3120
gtccgcacct catggcgccc gtaccggagc ta                                3152

SEQ ID NO: 30          moltype = DNA  length = 1692
FEATURE                Location/Qualifiers
source                 1..1692
                       mol_type = other DNA
                       organism = synthetic construct
SEQUENCE: 30
atggagatca gcaggagcgt gccaaggtgc accaccacca cccctggcgc tcgcatgcca  60
tgcagcctcc aagccctcgt gcccacgaaa gcgaggcagc cacggcgtct gacgtgcaag  120
gcaacgggcc gccgcgtcga ccgccgtgac gtgctcctcg gcctcggcag cgccgcggcg  180
gccgggctgg gcacgcggcg aggccgaggg gcgatcgcgg cgcccatcca ggcgccggac  240
ctcggcaact gccacccgcc cgacctcccg aacacggcgc cggacaccaa ctgctgcccg  300
acgtccggca ccgggatcgc cgacttcgtg ctgccgccgg cctcctcggc gccgctccgc  360
gtgcgcccgg ccgcgcacct ggtggacgcg gagcacctgg ccaagtacga gcgggccgtg  420
gcgctcatga agcagctgcc cgccgacgac ccgcgcagct tcgagcagca gtggcgcgtg  480
cactgcgcct actgcgacgg cgcgtacgac caggtcgggt tcccggacct ggagatccag  540
gtgcacaact gctggctctt cttcccatgg cacaggttct acctctactt ccacgagagg  600
atcctcggca agctcatcgg cgacgacacc ttcacgcttc cgttctggaa ctgggacgcg  660
ccggccggca tgacgctgcc ggcgatctac gccagcacgt cgtcgcctct ctacaacgag  720
aggcgcgacc ccgcccacca gccgcctttc ccgatcgacc ttgactacaa cgggaccgac  780
gtcatcgtcc caacagacga gcagatcgac cagaacctca ggatcatgta ccgccagatg  840
gtgtcgagtg ccaagaagac tcggctgttc atggggcagc cgtaccgcgc cggcgaccag  900
ccggacccgg gagcgggctc cgtggagaac ttgccgcacg gcacggtgca ccgctggacg  960
ggcgacccgg cgcagcccaa cggcgaggac atgggcaact tctactcggc ggcgcgcgac  1020
ctcatcttct tcgcgcacca cggcaacatc gaccgcctgt ggcacgtctg gcgcggcctc  1080
cgccccgcca acgccgactt cgccgacgcc gactggcttg acaccgcctt cctcttctac  1140
gacgaggaag cccgccccgt ccgtgtccgt gtccgcgact gcctcgacac ggccgccatg  1200
gggtacgcgt accaggacgt cgacctgccc tggctggacg ctaagcctgc caagaaatcg  1260
gccgggacgc cggtgccggc agcgggcgcg ctcccggcca cgctgggggga gaccgtgcgg  1320
gtgacggtga cgaggcccca ggtgtcaagg agcagcaagg agaaggagga ggcggaggag  1380
gtgctgatca tcgaggggat cgaggtcgcc gaccacttca agttcgtcaa gttcgacgtg  1440
ctggtgaacg agcccgagag cggaggcgac ggcgcgtctg ggtactgcgc cggcagcgtc  1500
gcgctgacgc cgcacatggt gcggacgaac aagaagaagg gctccgtgaa gacggtggcg  1560
aggttcggcg tctgcgacct gatggacaac atcggagccg acggtgacaa gacggtggtg  1620
gtgtcgctcg tgcccaggtg cggcggcgag ctggtcaccg tcggcggcgt cagcatcggc  1680
tatgtcaagt ga                                                      1692

SEQ ID NO: 31          moltype = DNA  length = 1734
FEATURE                Location/Qualifiers
source                 1..1734
                       mol_type = other DNA
                       organism = synthetic construct
SEQUENCE: 31
atggagagca gtcgcatgcc actgagtgcc acccctcgca tgccatgcag cctccaaacc  60
attgcgcgcc gcaaccttct ccgtgccctt caccgccgca aggacgcgag gcagccacgg  120
cgtctcccaa tctcatgcga ggcgaccggc ggcggctgcg tcgaccgccg tgaggtgctc  180
gtcggcctcg gcggcgccgc agctgccggg ctggtcacgg accaaggtcg aggcgccatc  240
gcagcgccca tccaggcccc ggacctccgc aactgccaaa cgcccgacct cccggacacg  300
gcgccggaca ccaactgctg cccgacgccc ggcaccggca tcaccgactt ccagctgccg  360
cccgccacct cgccgctccg cgtgcgtccg gcagcgcacc tggtggacgc ggaatacctg  420
gccaagtacg agagagccgt ggcgctcatg aagcagctgc ccgccgacga cccgcgcagc  480
ttcgagcagc agtggcacgt gcactgcgcc tactgcgacg ccgccttcga ccaggtcggg  540
ttcccggacc tggagctcca gatacacaac tgctggctct tcttcccatg gcacaggttc  600
tacctgtact tccacgagag gatcctcggc aagctcatcg gcgacgacac cttcgcgctg  660
cccttctgga actgggacgc gccggccggc atgacgctgc cggcgatcta cgccaacagg  720
tcgtcgccgc tctacgacga gaggcgcgac cccgcccacc agccgccggt gctgatcgac  780
cttgactcca gtgggaccga cgccagtatc ccaagaaacc agcagatcga tcagaacctc  840
aagatcatgt accgccagat gatttcggac gcgaagaaga cgctgctgtt cctgggacag  900
ccgtaccgcg ccggcgacca gccggacccg ggcgcgggct ccgtggagaa cgtgccgcac  960
ggcacggtcc acgtctggac aggcgaccca aggcagccca acggcgagga catgggcaac  1020
ttctactcgg cggcgcgcga ccccatcttc ttcgcgcacc acggcaacat cgaccgcctc  1080
tggcacgtct ggcgcggcct ccgcccgagc aacaccgact tcaccgaccc cgactggctc  1140
gacgccgcct tcctcttcta cgacgaggag gcccgccccg tgcgcgtgcg cgtccgggac  1200
tgcctcgaca cggccgggct gcggtacacg taccaggacg tcggcctgcc gtggctcaac  1260
gccaggccag ccaaggcgtc gaccggcacg ccggcgcccg ccaccaccag taccctgcca  1320
gccaccctgg acaggaccat acgggtgacg gtgacgaggc ccagggtgtc gaggagccgc  1380
cgggagaagg acgaggagga ggaggtgctg gtcgtggagg ggatcgagat cgccgaccgt  1440
ttcaacaagt tcgtcaagtt cgacgtgctg gtgaacgagc ccgagggcgg agtgggtggc  1500
atgccggcgg tggcgacggg gtactgcgct gggagcttcg cgcacacgcc gcacatgatc  1560
cggcccgacg agatgaggaa ggggtcggtc aagacggtgg cgaggttcgg cgtgtgcgac  1620
ctgatggacg acatcggggc ggacggagac aagacggtgg tcgtttcgct ggtgccgagg  1680
tccggcggcg agctggtcac cgtcggcggc gtcagcatca gctacctcaa gtga        1734

SEQ ID NO: 32          moltype = AA  length = 563
FEATURE                Location/Qualifiers
source                 1..563
```

```
                        mol_type = protein
                        organism = Secale cereale
SEQUENCE: 32
MEISRSVPRC TTTTPGARMP CSLQALVPTK ARQPRRLTCK ATGRRVDRRD VLLGLGSAAA  60
AGLGTRRGRG AIAAPIQAPD LGNCHPPDLP NTAPDTNCCP TSGTGIADFV LPPASSAPLR  120
VRPAAHLVDA EHLAKYERAV ALMKQLPADD PRSFEQQWRV HCAYCDGAYD QVGFPDLEIQ  180
VHNCWLFFPW HRFYLYFHER ILGKLIGDDT FTLPFWNWDA PAGMTLPAIY ASTSSPLYNE  240
RRDPAHQPPF PIDLDYNGTD VIVPTDEQID QNLRIMYRQM VSSAKKTRLF MGQPYRAGDQ  300
PDPGAGSVEN LPHGTVHRWT GDPAQPNGED MGNFYSAARD LIFFAHHGNI DRLWHVWRGL  360
RPANADFADA DWLDTAFLFY DEEARPVRVR VRDCLDTAAM GYAYQDVDLP WLDAKPAKKS  420
AGTPVPAAGA LPATLGETVR VTVTRPQVSR SSKEKEEAEE VLIIEGIEVA DHFKFVKFDV  480
LVNEPESGGD GASGYCAGSV ALTPHMVRTN KKKGSVKTVA RFGVCDLMDN IGADGDKTVV  540
VSLVPRCGGE LVTVGGVSIG YVK                                          563

SEQ ID NO: 33           moltype = AA  length = 577
FEATURE                 Location/Qualifiers
source                  1..577
                        mol_type = protein
                        organism = Secale cereale
SEQUENCE: 33
MESSRMPLSA TPRMPCSLQT IARRNLLRAL HRRKDARQPR RLPISCEATG GGCVDRREVL  60
VGLGGAAAAG LVTDQGRGAI AAPIQAPDLR NCQTPDLPDT APDTNCCPTP GTGITDFQLP  120
PATSPLRVRP AAHLVDAEYL AKYERAVALM KQLPADDPRS FEQQWHVHCA YCDAAFDQVG  180
FPDLELQIHN CWLFFPWHRF YLYFHERILG KLIGDDTFAL PFWNWDAPAG MTLPAIYANR  240
SSPLYDERRD PAHQPPVLID LDSSGTDASI PRNQQIDQNL KIMYRQMISD AKKTLLFLGQ  300
PYRAGDQPDP GAGSVENVPH GTVHVWTGDP RQPNGEDMGN FYSAARDPIF FAHHGNIDRL  360
WHVWRGLRPS NTDFTDPDWL DAAFLFYDEE ARPVRVRVRD CLDTAGLRYT YQDVGLPWLN  420
ARPAKASTGT PAPATTSTLP ATLDRTIRVT VTRPRVSRSR REKDEEEEVL VVEGIEIADR  480
FNKFVKFDVL VNEPEGGVGG MPAVATGYCA GSFAHTPHMI RPDEMRKGSV KTVARFGVCD  540
LMDDIGADGD KTVVVSLVPR SGGELVTVGG VSISYLK                           577

SEQ ID NO: 34           moltype = RNA  length = 21
FEATURE                 Location/Qualifiers
source                  1..21
                        mol_type = other RNA
                        organism = synthetic construct
SEQUENCE: 34
gcgtggtgcg cgaagaagat g                                            21

SEQ ID NO: 35           moltype = AA  length = 46
FEATURE                 Location/Qualifiers
source                  1..46
                        mol_type = protein
                        organism = synthetic construct
VARIANT                 2
                        note = X is G or N
VARIANT                 3
                        note = X is T or P
VARIANT                 4
                        note = X is V or M
VARIANT                 6
                        note = X is V, T, G, N, I, or R
VARIANT                 12
                        note = X is R, A, or N
VARIANT                 16
                        note = X is L, N, G, S, or R
VARIANT                 17
                        note = X is A or E
VARIANT                 23
                        note = X is Y or F
VARIANT                 29
                        note = X is P or L
VARIANT                 36
                        note = X is G or A
VARIANT                 38
                        note = X is N or I
VARIANT                 39
                        note = X is M or I
VARIANT                 41
                        note = X is W or R
SEQUENCE: 35
HXXXHXWTGD PXQPNXXDMG NFXSAARDXI FFAHHXGXXD XLWHVW                 46

SEQ ID NO: 36           moltype = DNA  length = 23
FEATURE                 Location/Qualifiers
source                  1..23
                        mol_type = genomic DNA
                        organism = Triticum aestivum
SEQUENCE: 36
```

```
ccccatcttc ttcgcgcacc acg                                              23

SEQ ID NO: 37          moltype = DNA  length = 23
FEATURE                Location/Qualifiers
source                 1..23
                       mol_type = genomic DNA
                       organism = Triticum aestivum
SEQUENCE: 37
cccgctcttc tacccgcacc aca                                              23

SEQ ID NO: 38          moltype = DNA  length = 23
FEATURE                Location/Qualifiers
source                 1..23
                       mol_type = genomic DNA
                       organism = Triticum aestivum
SEQUENCE: 38
cccgctcttc tacccgcagc aca                                              23

SEQ ID NO: 39          moltype = DNA  length = 23
FEATURE                Location/Qualifiers
source                 1..23
                       mol_type = genomic DNA
                       organism = Triticum aestivum
SEQUENCE: 39
cccactcttc tacccacacc aca                                              23

SEQ ID NO: 40          moltype = DNA  length = 23
FEATURE                Location/Qualifiers
source                 1..23
                       mol_type = genomic DNA
                       organism = Triticum aestivum
SEQUENCE: 40
cccactcttc tacccacaca aca                                              23

SEQ ID NO: 41          moltype = DNA  length = 23
FEATURE                Location/Qualifiers
source                 1..23
                       mol_type = genomic DNA
                       organism = Triticum aestivum
SEQUENCE: 41
cccgctcttc tacctgcacc aca                                              23

SEQ ID NO: 42          moltype = DNA  length = 23
FEATURE                Location/Qualifiers
source                 1..23
                       mol_type = genomic DNA
                       organism = Triticum aestivum
SEQUENCE: 42
ccccgtcttc tactcgcacc acg                                              23

SEQ ID NO: 43          moltype = DNA  length = 23
FEATURE                Location/Qualifiers
source                 1..23
                       mol_type = genomic DNA
                       organism = Triticum aestivum
SEQUENCE: 43
cccggtcttc ttcgcgcacc acg                                              23

SEQ ID NO: 44          moltype = DNA  length = 23
FEATURE                Location/Qualifiers
source                 1..23
                       mol_type = genomic DNA
                       organism = Triticum aestivum
SEQUENCE: 44
cccggtcttc tttgcacacc acg                                              23

SEQ ID NO: 45          moltype = DNA  length = 23
FEATURE                Location/Qualifiers
source                 1..23
                       mol_type = genomic DNA
                       organism = Triticum aestivum
SEQUENCE: 45
ccccgtcttc tactccaacc act                                              23

SEQ ID NO: 46          moltype = DNA  length = 23
FEATURE                Location/Qualifiers
source                 1..23
                       mol_type = genomic DNA
                       organism = Hordeum vulgare
```

```
SEQUENCE: 46
ccccatcttc ttcgcgcacc acg                                          23

SEQ ID NO: 47          moltype = DNA  length = 23
FEATURE                Location/Qualifiers
source                 1..23
                       mol_type = genomic DNA
                       organism = Secale cereale
SEQUENCE: 47
cctcatcttc ttcgcgcacc acg                                          23

SEQ ID NO: 48          moltype = DNA  length = 23
FEATURE                Location/Qualifiers
source                 1..23
                       mol_type = genomic DNA
                       organism = Secale cereale
SEQUENCE: 48
ccccatcttc ttcgcgcacc acg                                          23

SEQ ID NO: 49          moltype = DNA  length = 23
FEATURE                Location/Qualifiers
source                 1..23
                       mol_type = genomic DNA
                       organism = Zea mays
SEQUENCE: 49
cccggtgttc ttcgcgcacc acg                                          23

SEQ ID NO: 50          moltype = DNA  length = 23
FEATURE                Location/Qualifiers
source                 1..23
                       mol_type = genomic DNA
                       organism = Zea mays
SEQUENCE: 50
cccgctcttc ttcgcgcacc acg                                          23

SEQ ID NO: 51          moltype = DNA  length = 23
FEATURE                Location/Qualifiers
source                 1..23
                       mol_type = genomic DNA
                       organism = Zea mays
SEQUENCE: 51
cccgctcttc tactcgcacc acg                                          23

SEQ ID NO: 52          moltype = DNA  length = 23
FEATURE                Location/Qualifiers
source                 1..23
                       mol_type = genomic DNA
                       organism = Zea mays
SEQUENCE: 52
ccccatcttc ttcccgcacc aca                                          23

SEQ ID NO: 53          moltype = DNA  length = 23
FEATURE                Location/Qualifiers
source                 1..23
                       mol_type = genomic DNA
                       organism = Oryza sativa
SEQUENCE: 53
cccggtgttc ttcgcgcacc acg                                          23

SEQ ID NO: 54          moltype = DNA  length = 23
FEATURE                Location/Qualifiers
source                 1..23
                       mol_type = genomic DNA
                       organism = Sorghum bicolor
SEQUENCE: 54
cccgctcttc tactcgcacc acg                                          23

SEQ ID NO: 55          moltype = DNA  length = 23
FEATURE                Location/Qualifiers
source                 1..23
                       mol_type = genomic DNA
                       organism = Sorghum bicolor
SEQUENCE: 55
tccactcttc ttcgcgcacc acg                                          23

SEQ ID NO: 56          moltype = DNA  length = 23
FEATURE                Location/Qualifiers
source                 1..23
                       mol_type = genomic DNA
```

```
                         organism = Sorghum bicolor
SEQUENCE: 56
tccgctcttc ttcgcgcacc acg                                        23

SEQ ID NO: 57            moltype = DNA  length = 23
FEATURE                  Location/Qualifiers
source                   1..23
                         mol_type = genomic DNA
                         organism = Sorghum bicolor
SEQUENCE: 57
ccccatcttc tacccgcacc acg                                        23

SEQ ID NO: 58            moltype = DNA  length = 60
FEATURE                  Location/Qualifiers
source                   1..60
                         mol_type = genomic DNA
                         organism = Triticum aestivum
SEQUENCE: 58
ttctcggcgg cgcgcgaccc catcttcttc gcgcaccacg gcaacatgga ccgcctgtgg  60

SEQ ID NO: 59            moltype = DNA  length = 60
FEATURE                  Location/Qualifiers
source                   1..60
                         mol_type = genomic DNA
                         organism = Triticum aestivum
SEQUENCE: 59
tactcggcgg cgcgcgaccc catcttcttc gcgcaccacg gcaacatcga ccgcctctgg  60

SEQ ID NO: 60            moltype = DNA  length = 60
FEATURE                  Location/Qualifiers
source                   1..60
                         mol_type = genomic DNA
                         organism = Triticum aestivum
SEQUENCE: 60
tactcggcgg cgcgcgaccc catcttcttc gcgcaccacg gcatcatcga ccgcctgtgg  60

SEQ ID NO: 61            moltype = DNA  length = 60
FEATURE                  Location/Qualifiers
source                   1..60
                         mol_type = genomic DNA
                         organism = Triticum aestivum
SEQUENCE: 61
tactcggcgg cgcgcgaccc catcttcttc gcgcaccacg gcaacatcga ccgcctgtgg  60

SEQ ID NO: 62            moltype = DNA  length = 60
FEATURE                  Location/Qualifiers
source                   1..60
                         mol_type = genomic DNA
                         organism = Triticum aestivum
SEQUENCE: 62
tactccgccg gccgagaccc gctcttctac ccgcaccaca acaacgtcga ccgccagtgg  60

SEQ ID NO: 63            moltype = DNA  length = 60
FEATURE                  Location/Qualifiers
source                   1..60
                         mol_type = genomic DNA
                         organism = Triticum aestivum
SEQUENCE: 63
tactccgccg gccgagaccc gctcttctac ccgcagcaca gcaacatcga ccgcctgtgg  60

SEQ ID NO: 64            moltype = DNA  length = 60
FEATURE                  Location/Qualifiers
source                   1..60
                         mol_type = genomic DNA
                         organism = Triticum aestivum
SEQUENCE: 64
tactcagccg gccgagaccc actcttctac ccacaccaca gcaacataga ccgcctgtgg  60

SEQ ID NO: 65            moltype = DNA  length = 60
FEATURE                  Location/Qualifiers
source                   1..60
                         mol_type = genomic DNA
                         organism = Triticum aestivum
SEQUENCE: 65
tactcagccg gccgagaccc actcttctac ccacacaaca gcaacataga tcgcctgtgg  60

SEQ ID NO: 66            moltype = DNA  length = 60
FEATURE                  Location/Qualifiers
source                   1..60
```

-continued

```
                         mol_type = genomic DNA
                         organism = Triticum aestivum
SEQUENCE: 66
tactccgccg gccgggaccc gctcttctac ctgcaccaca acaacattga ccgcctgtgg  60

SEQ ID NO: 67            moltype = DNA  length = 60
FEATURE                  Location/Qualifiers
source                   1..60
                         mol_type = genomic DNA
                         organism = Triticum aestivum
SEQUENCE: 67
tactcagccg cccgagaccc actcttctac ccacaccaca gcaacataga ccgcctgtgg  60

SEQ ID NO: 68            moltype = DNA  length = 60
FEATURE                  Location/Qualifiers
source                   1..60
                         mol_type = genomic DNA
                         organism = Triticum aestivum
SEQUENCE: 68
tactcggccg gccgagaccc actcttctac ccacaccaca gcaacataga ccgcctgtgg  60

SEQ ID NO: 69            moltype = DNA  length = 60
FEATURE                  Location/Qualifiers
source                   1..60
                         mol_type = genomic DNA
                         organism = Triticum aestivum
SEQUENCE: 69
ggcacggcgg ggcgcgaccc cgtcttctac tcgcaccacg ccaacgtcga ccgcatgtgg  60

SEQ ID NO: 70            moltype = DNA  length = 60
FEATURE                  Location/Qualifiers
source                   1..60
                         mol_type = genomic DNA
                         organism = Triticum aestivum
SEQUENCE: 70
tactccgcgg cacgcgaccc ggtcttcttc gcgcaccacg gcaacgtcga ccgcatgtgg  60

SEQ ID NO: 71            moltype = DNA  length = 60
FEATURE                  Location/Qualifiers
source                   1..60
                         mol_type = genomic DNA
                         organism = Triticum aestivum
SEQUENCE: 71
tactccgtgg cacgcgaccc ggtcttcttt gcacaccacg gcacgtcgac cgccatgtgg  60

SEQ ID NO: 72            moltype = DNA  length = 60
FEATURE                  Location/Qualifiers
source                   1..60
                         mol_type = genomic DNA
                         organism = Triticum aestivum
SEQUENCE: 72
ggcacggccg gccgcgaccc cgtcttctac tcgcaccacg ccaacgtcga ccgcatgtgg  60

SEQ ID NO: 73            moltype = DNA  length = 60
FEATURE                  Location/Qualifiers
source                   1..60
                         mol_type = genomic DNA
                         organism = Triticum aestivum
SEQUENCE: 73
ggcaccgccg gccgcgaccc cgtcttctac tcgcaccacg ccaacgtcga ccgcatgtgg  60

SEQ ID NO: 74            moltype = DNA  length = 60
FEATURE                  Location/Qualifiers
source                   1..60
                         mol_type = genomic DNA
                         organism = Triticum aestivum
SEQUENCE: 74
agcacggcgg cgcgcgaccc cgtcttctac tccaaccact ccaacgtgga ccgcatgtgg  60
```

METHODS AND COMPOSITIONS FOR REDUCING POLYPHENOL OXIDASE ACTIVITY IN PLANTS

CROSS REFERENCE TO RELATED APPLICATIONS

This application claims priority to provisional application U.S. Ser. No. 63/493,525, filed Mar. 31, 2023, which is incorporated herein by reference in its entirety.

SEQUENCE LISTING XML

The instant application contains a sequence listing, which has been submitted in XML file format by electronic submission and is hereby incorporated by reference in its entirety. The XML file, created on Mar. 29, 2024, is named P13996US01.xml and is 133,837 bytes in size.

TECHNICAL FIELD

The present disclosure relates to the field of biotechnology. More specifically, the present disclosure relates to compositions and methods for reducing polyphenol oxidase activity in plants.

BACKGROUND

Polyphenol oxidases (PPO) are dual activity metalloenzymes that catalyse the production of quinones. Quinones react non-enzymatically with cellular thiol and amine groups to produce melanin pigments, causing browning and discoloration of plant tissues. PPO activity is generally undesirable for the food industry because it causes the discoloration of plant tissues and changes in flavor profiles during post-harvest processing. A readily observed example is the browning of fresh fruit and vegetables following cutting. In common wheat (*Triticum aestivum* L.) PPO enzymes released from the aleurone layer of the grain during milling catalyze biochemical reactions that result in the time-dependent darkening and discoloration of flour, dough, and end-use products including noodles. Although this can be mitigated by reducing the flour extraction rate during milling, there is need in the art for other approaches to reduce PPO activity in wheat and other plants.

SUMMARY

Modified plants, and progeny thereof, having reduced polyphenol oxidase (PPO) activity, the plant comprising a mutation in at least one endogenous PPO1 or PPO2 gene are provided. In certain embodiments, the mutation is in a region of the endogenous PPO1 or PPO2 gene that encodes a copper binding domain of a PPO polypeptide. In certain embodiments, the modified plant is a wheat plant comprising a mutation in each of PPO2A-1, PPO2A-2, PPO2B-1, PPO2B-2, PPO2B-3, PPO2D-1, and PPO2D-2. Plant parts, plant cells, and seeds of the modified plants are also provided.

Methods of reducing PPO activity in a plant are provided. In certain embodiments, the methods comprise reducing the expression or activity of at least one PPO polypeptide encoded by an endogenous PPO1 or PPO2 gene. In certain embodiments, the methods comprise introducing a mutation in at least one endogenous PPO1 or PPO2 gene. In certain embodiments, the mutation is in a region of the endogenous PPO1 or PPO2 gene that encodes a copper binding domain of a PPO polypeptide. In certain embodiments, the mutation is introduced by genome editing.

Methods of producing a wheat plant having reduced PPO activity are provided. The methods comprising (a) crossing a plant of the disclosure with itself or another plant to produce seed; and (b) growing a progeny plant from the seed to produce a plant having grain with reduced PPO activity. In certain embodiments, the methods further comprise (c) crossing the progeny plant with itself or another plant; and (d) repeating steps (b) and (c) for an additional 0-7 generations to produce a plant having reduced PPO activity.

A crop comprising a plurality of the plants of the disclosure planted together in an agricultural field is provided.

Commodity plant products prepared from the plants of the disclosure or parts thereof are provided. In certain embodiments, the product is grain, flour, a baked good, cereal, pasta, a beverage, livestock feed, biofuel, straw, a construction material, or starch. In certain embodiments, the products have reduced browning. In wheat, PPO released from the aleurone layer of the grain during milling results in the discoloration of flour and dough, reducing the value of some end-use products. Methods for producing the commodity plant products are also provided.

A guide RNA for editing PPO1 or PPO2 genes is provided. The guide RNA sequence shares 100% sequence identity in all PPO1 and PPO2 genes present in wheat varieties with assembled genomes and can be applied broadly in diverse wheat germplasm as well as barley and rye. Expression cassettes and vectors encoding the guide RNA are provided. Plant cells comprising a Cas9 nuclease and the guide RNA are also provided.

While multiple embodiments are disclosed, still other embodiments of the present disclosure will become apparent based on the detailed description, which shows and describes illustrative embodiments of the disclosure. Accordingly, the figures and detailed description are to be regarded as illustrative in nature and not restrictive.

BRIEF DESCRIPTION OF THE FIGURES

The following drawings form part of the specification and are included to further demonstrate certain embodiments. In some instances, embodiments can be best understood by referring to the accompanying figures in combination with the detailed description presented herein. The description and accompanying figures may highlight a certain specific example, or a certain embodiment. However, one skilled in the art will understand that portions of the example or embodiment may be used in combination with other examples or embodiments.

FIG. 4A shows mean PPO activity from $T_1$ lines (n=12 to 18). 'Ripper' (high-PPO bread wheat), 'Platte' (low-PPO bread wheat) and 'Kronos' (low-PPO durum wheat) were included as control lines (n=10). FIG. 4B shows PPO activity in 'Fielder' $T_2$ lines derived from selected $T_1$ individuals.

DETAILED DESCRIPTION

Figure 1:
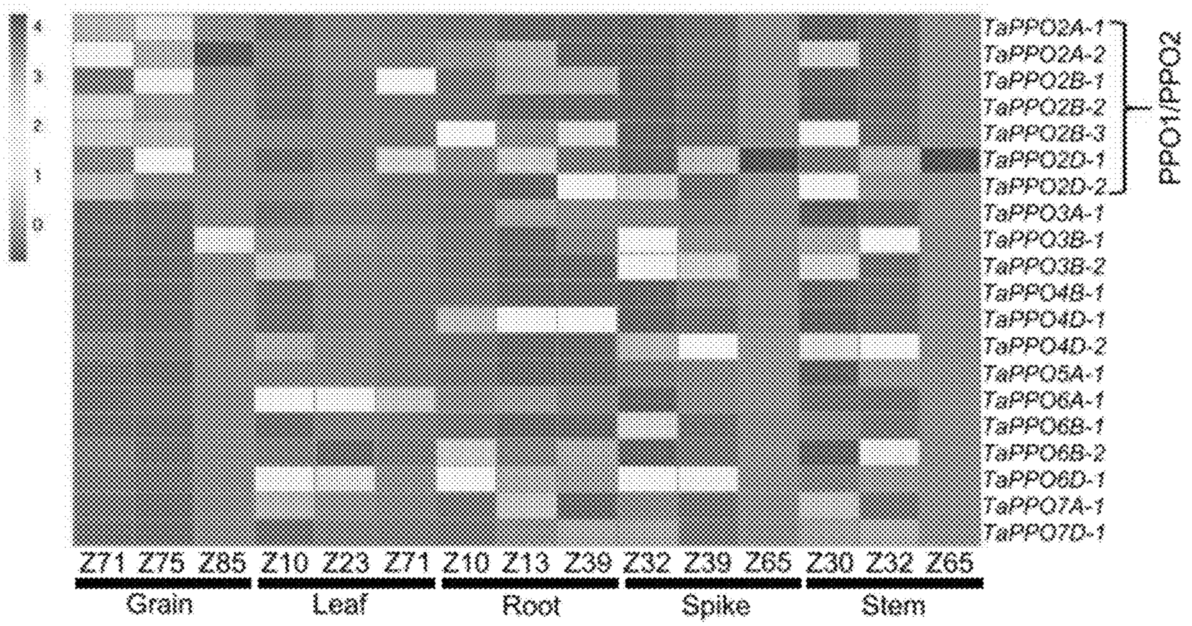
FIG. 1 shows the expression profiles of 20 wheat PPO genes during grain development. RNA-seq reads from a grain developmental timecourse were mapped to the IWGSC RefSeq v1.1 wheat reference genome. Expression in transcript per million (TPM) values are scaled.

So that the present disclosure may be more readily understood, certain terms are first defined. Unless defined otherwise, all technical and scientific terms used herein have the same meaning as commonly understood by one of ordinary skill in the art to which embodiments of the disclosure pertain. Many methods and materials similar, modified, or equivalent to those described herein can be used in the practice of the embodiments of the present disclosure without undue experimentation, the preferred materials and methods are described herein. In describing and claiming the embodiments of the present disclosure, the following terminology will be used in accordance with the definitions set out below.

It is to be understood that all terminology used herein is for the purpose of describing particular embodiments only and is not intended to be limiting in any manner or scope. For example, as used in this specification and the appended claims, the singular forms "a," "an" and "the" can include plural referents unless the content clearly indicates otherwise. Thus, for example, reference to "a mutation" includes a single mutation, as well as two or more mutations; reference to "a plant" includes one plant, as well as two or more plants; and so forth. Similarly, the word "or" is intended to include "and" unless the context clearly indicate otherwise. The word "or" means any one member of a particular list and also includes any combination of members of that list. Further, all units, prefixes, and symbols may be denoted in its SI accepted form.

Numeric ranges recited within the specification are inclusive of the numbers defining the range and include each integer within the defined range. Throughout this disclosure, various embodiments of this disclosure are presented in a range format. It should be understood that the description in range format is merely for convenience and brevity and should not be construed as an inflexible limitation on the scope of the disclosure. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4¾. This applies regardless of the breadth of the range.

As used herein, the terms "include," "includes," and "including" are to be construed as at least having the features to which they refer while not excluding any additional unspecified features.

As used herein, the terms "cross" or "crossed" refer to the fusion of gametes via pollination to produce progeny (e.g., cells, seeds, or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

As used herein, the terms "backcross" and "backcrossing" refer to the process whereby a progeny plant is crossed back to one of its parents one or more times (e.g., 1, 2, 3, 4, 5, 6, 7, 8, etc.). In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. The initial cross gives rise to the F1 generation. The term "BC1" refers to the second use of the recurrent parent, "BC2" refers to the third use of the recurrent parent, and so on.

As used herein, the term "hybrid" in the context of plant breeding refers to a plant that is the offspring of genetically dissimilar parents produced by crossing plants of different lines or breeds or species, including but not limited to the cross between two inbred lines.

As used herein, the term "inbred" refers to a substantially homozygous plant or variety. The term can refer to a plant or plant variety that is substantially homozygous throughout the entire genome or that is substantially homozygous with respect to a portion of the genome that is of particular interest.

As used herein, the term "heterozygous" refers to a genetic status wherein different alleles reside at corresponding loci on homologous chromosomes.

As used herein, the term "homozygous" refers to a genetic status wherein identical alleles reside at corresponding loci on homologous chromosomes.

As used herein, the term "allele" refers to one of two or more different nucleotides or nucleotide sequences that occur at a specific locus.

A "null allele" or "null mutation" is a nonfunctional allele caused by a genetic mutation that results in a complete lack of production of the corresponding protein or produces a protein that is non-functional.

A "hypomorphic allele" or "hypomorphic mutation" is a mutation that results in a partial loss of gene function, which can occur through reduced expression (e.g., reduced protein and/or reduced RNA) or reduced functional performance (e.g., reduced activity), but not a complete loss of function/activity.

As used herein, the terms "reduce," "reduced," "reducing," "reduction," "diminish," and "decrease" (and grammatical variations thereof), describe, for example, a decrease of at least about 5%, 10%, 15%, 20%, 25%, 35%, 50%, 75%, 80%, 85%, 90%, 95%, 96%, 97%, 98%, 99%, 99.5%, 99.6%, 99.7%, 99.8%, 99.9%, or 100% as compared to a control. In some embodiments, the reduction can result in no or essentially no (i.e., an insignificant amount, e.g., less than about 10% or even 5%) detectable activity or amount.

A "region" of a polynucleotide or a polypeptide refers to a portion of consecutive nucleotides or consecutive amino acid residues of that polynucleotide or a polypeptide, respectively.

Polyphenol oxidases (PPO) are di-copper metalloenzymes found in all land plants except the *Arabidopsis* genus. PPOs are dual activity enzymes, catalyzing the hydroxylation of monophenols to diphenols (tyrosinase activity) and the oxidation of o-diphenols to o-quinones (catechol oxidase activity). Quinones react non-enzymatically with cellular thiol and amine groups to produce melanin pigments, causing browning and discoloration of plant tissues. The active site for these reactions includes two highly conserved copper binding domains (CuA and CuB) each with three histidine residues that coordinate interactions between phenols and molecular oxygen. Many PPO proteins are localized in the chloroplast and come into contact with their phenolic substrates only following senescence, wounding, or physical disruption.

The wheat genome contains paralogous clusters of PPO1 and PPO2 genes on homoeologous group 2 chromosomes that are expressed in the developing grain and contribute to PPO levels. Limited natural variation and small genetic distances between the genes at these loci complicates the selection of extremely low-PPO wheat varieties by recombination.

The present disclosure relates to modified plants comprising a mutation in at least one endogenous PPO1 or PPO2 gene, optionally within a region of the endogenous gene encoding a copper binding domain (e.g., a CuB domain). Accordingly, in some embodiments, the present disclosure is directed to generating mutations in endogenous PPO1 or PPO2 genes, optionally wherein the mutation is in a region of the PPO1 or PPO2 gene encoding a copper binding domain (e.g., a CuB domain).

Table 1 provides a summary of the endogenous PPO1 and PPO2 sequences in wheat, barley, and rye.

of SEQ ID NO: 5, or an allelic variant thereof. The corresponding amino acid sequence is SEQ ID NO: 19. In certain embodiments, the endogenous PPO2D-1 gene comprises or consists of SEQ ID NO: 6, or an allelic variant thereof. The corresponding amino acid sequence is SEQ ID NO: 20. In certain embodiments, the endogenous PPO2D-2 gene comprises or consists of SEQ ID NO: 7, or an allelic variant thereof. The corresponding amino acid sequence is SEQ ID NO: 21.

The phrase "allelic variant" as used herein refers to a polynucleotide sequence variant that occurs in a different strain, variety, or isolate of a given organism. It would be understood that there is natural variation in the sequences of PPO1 or PPO2 genes from different plant varieties. The allelic variants are readily recognizable by the skilled artisan on the basis of genome synteny and sequence similarity.

An allele is a variant of a gene at a single genetic locus. A diploid organism has two sets of chromosomes. Each chromosome has one copy of each gene (one allele). If both alleles are the same the organism is homozygous with respect to that gene, if the alleles are different, the organism is heterozygous with respect to that gene. The interaction between alleles at a locus is generally described as dominant or recessive. In certain embodiments, the mutation is a loss of function mutation. A loss of function mutation, which includes a partial loss of function mutation in an allele, means a mutation in the allele leading to no or a reduced level or activity of PPO enzyme in the grain. The mutation may mean, for example, that no or less RNA is transcribed from the gene comprising the mutation, that less protein is translated, or that the protein produced has no or reduced activity. Alleles that do not encode or are not capable of leading to the production of any active enzyme are null

TABLE 1

| PPO1/PPO2 gene | Genomic sequence | Coding sequence | Protein sequence |
|---|---|---|---|
| TaPPO2A-1 (TraesCS2A02G468200) | SEQ ID NO: 1 | SEQ ID NO: 8 | SEQ ID NO: 15 |
| TaPPO2A-2 (TraesCS2A02G468500) | SEQ ID NO: 2 | SEQ ID NO: 9 | SEQ ID NO: 16 |
| TaPPO2B-1 (TraesCS2B02G491000) | SEQ ID NO: 3 | SEQ ID NO: 10 | SEQ ID NO: 17 |
| TaPPO2B-2 (TraesCS2B02G491100) | SEQ ID NO: 4 | SEQ ID NO: 11 | SEQ ID NO: 18 |
| TaPPO2B-3 (TraesCS2B02G491400) | SEQ ID NO: 5 | SEQ ID NO: 12 | SEQ ID NO: 19 |
| TaPPO2D-1 (TraesCS2D02G468200) | SEQ ID NO: 6 | SEQ ID NO: 13 | SEQ ID NO: 20 |
| TaPPO2D-2 (TraesCS2D02G468600) | SEQ ID NO: 7 | SEQ ID NO: 14 | SEQ ID NO: 21 |
| HvPPO-1 (HORVU.MOREX.r3.2HG0194690) | SEQ ID NO: 22 | SEQ ID NO: 24 | SEQ ID NO: 26 |
| HvPPO-2 (HORVU.MOREX.r3.2HG0194630) | SEQ ID NO: 23 | SEQ ID NO: 25 | SEQ ID NO: 27 |
| ScPPO-1 (SECCE2Rv1G0121020) | SEQ ID NO: 28 | SEQ ID NO: 30 | SEQ ID NO: 32 |
| ScPPO-2 (SECCE2Rv1G0121070) | SEQ ID NO: 29 | SEQ ID NO: 31 | SEQ ID NO: 33 |

The PPO1 or PPO2 genes as defined above include any regulatory sequences that are 5' or 3' of the transcribed region, including the promoter region, that regulate the expression of the associated transcribed region, and introns within the transcribed regions.

In certain embodiments, the endogenous PPO2A-1 gene comprises or consists of SEQ ID NO: 1, or an allelic variant thereof. The corresponding amino acid sequence is SEQ ID NO: 15. In certain embodiments, the endogenous PPO2A-2 gene comprises or consists of SEQ ID NO: 2, or an allelic variant thereof. The corresponding amino acid sequence is SEQ ID NO: 16. In certain embodiments, the endogenous PPO2B-1 gene comprises or consists of SEQ ID NO: 3, or an allelic variant thereof. The corresponding amino acid sequence is SEQ ID NO: 17. In certain embodiments, the endogenous PPO2B-2 gene comprises or consists of SEQ ID NO: 4, or an allelic variant thereof. The corresponding amino acid sequence is SEQ ID NO: 18. In certain embodiments, the endogenous PPO2B-3 gene comprises or consists alleles. A "reduced" amount or level of protein means reduced relative to the amount or level produced by the corresponding wild-type allele. A "reduced" activity means reduced relative to the corresponding wild-type PPO enzyme. Different alleles may have the same or a different mutation and different alleles may be combined using methods known in the art. In some embodiments, the amount of PPO protein is reduced because there is less transcription or translation of the PPO1 or PPO2 gene, respectively. In some embodiments, the amount by weight of PPO protein is reduced even though there is a wild-type number of PPO protein molecules, because some of the proteins produced are shorter than wild-type PPO protein, e.g., the mutant PPO protein is truncated due to a premature translation termination signal.

A mutation in an endogenous PPO1 or PPO2 gene in a plant can be any type of mutation including a substitution, a deletion, or an insertion. In some embodiments, the mutation can be a deletion or an insertion of at least one or at least two or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more) consecutive nucleotides.

Mutations in the endogenous PPO1 or PPO2 gene can result in insertions of one or more amino acids, deletions of one or more amino acids, or conservative or non-conservative amino acid substitutions in the encoded PPO polypeptide. In certain embodiments, the endogenous PPO1 or PPO2 gene comprises more than one mutation or more than one type of mutation. Insertion or deletion of amino acids can, for example, disrupt the conformation of the PPO polypeptide, change the localization of the PPO polypeptide, or disrupt an active site or domain within the PPO polypeptide. In certain embodiments, the function of a copper binding domain (e.g., a CuB domain) of the PPO polypeptide is disrupted.

In certain embodiments, the mutation is within a region of the endogenous PPO1 or PPO2 gene encoding a CuB domain of a PPO polypeptide. A CuB domain encoded by an endogenous PPO1 or PPO2 gene is located in a region of the gene from about nucleotide 2035 to about nucleotide 2169 with reference to nucleotide numbering of SEQ ID NO:1 (TaPPO2A-1). A CuB domain is located in a region of the PPO polypeptide from about amino acid 320 to about amino acid 354 with reference to amino acid numbering of SEQ ID NO: 15.

Genome editing methods can produce site-specific mutants in a plant genome. Genome editing uses engineered nucleases such as RNA guided DNA endonucleases or nucleases composed of sequence specific DNA binding domains fused to a non-specific DNA cleavage module. These engineered nucleases enable efficient and precise genetic modifications by inducing targeted DNA double stranded breaks that stimulate the cell's endogenous cellular DNA repair mechanisms to repair the induced break. Such mechanisms include, for example, error prone non-homologous end joining (NHEJ) and homology directed repair (HDR).

In the presence of donor plasmid with extended homology arms, HDR can lead to the introduction of single or multiple transgenes to correct or replace existing genes. In the absence of donor plasmid, NHEJ-mediated repair yields small insertion or deletion mutations of the target that cause gene disruption. Engineered nucleases useful in the methods of the present disclosure include zinc finger nucleases (ZFNs), transcription activator-like (TAL) effector nucleases (TALEN), and the CRISPR/Cas system.

CRISPR systems rely on CRISPR RNA (crRNA) and transactivating chimeric RNA (tracrRNA) for sequence-specific cleavage of DNA. Three types of CRISPR/Cas systems exist: in type II systems, Cas9 serves as an RNA-guided DNA endonuclease that cleaves DNA upon crRNA-tracrRNA target recognition. CRISPR RNA base pairs with tracrRNA to form a two-RNA structure that guides the Cas9 endonuclease to complementary DNA sites for cleavage.

The CRISPR system can be portable to plant cells by co-delivery of plasmids expressing the Cas endonuclease and the necessary crRNA components. The Cas endonuclease may be converted into a nickase to provide additional control over the mechanism of DNA repair (Cong et al., 2013).

CRISPRs are typically short partially palindromic sequences of 24-40 bp containing inner and terminal inverted repeats of up to 11 bp. Although isolated elements have been detected, they are generally arranged in clusters (up to about 20 or more per genome) of repeated units spaced by unique intervening 20-58 bp sequences. CRISPRs are generally homogenous within a given genome with most of them being identical. However, there are examples of heterogeneity in, for example, the Archaca (Mojica et al., 2000).

In some embodiments, the present disclosure provides a guide nucleic acid (e.g., gRNA, gDNA, crRNA, crDNA) that binds to a target site in an endogenous PPO1 or PPO2 gene. In certain embodiments, the guide nucleic acid binds to a target site a region of the endogenous PPO1 or PPO2 gene that encodes a copper binding domain of a PPO polypeptide. Example spacer sequences useful with a guide nucleic acid of this disclosure can comprise complementarity to a fragment or portion (or region) (e.g., at least about 20 consecutive nucleotides) of a nucleic acid sequence comprising a sequence having at least 80%, at least 90%, at least 95%, at least 98%, at least 99%, or 100% sequence identity to SEQ ID NO: 1, 2, 3, 4, 5, 6, 7, 22, 23, 28, or 29. In certain embodiments, a spacer of a guide nucleic acid can include, but is not limited to, the nucleotide sequence of SEQ ID NO: 34.

A CRISPR Cas9 effector protein or CRISPR Cas9 effector domain useful with this disclosure can be any known or later identified Cas9 nuclease. In some embodiments, a CRISPR Cas9 polypeptide can be a Cas9 polypeptide from, for example, *Streptococcus* spp. (e.g., *S. pyogenes*, S. thermophiles), *Lactobacillus* spp., *Bifidobacterium* spp., *Kandleria* spp., *Leuconostoc* spp., *Oenococcus* spp., *Pediococcus* spp., *Weissella* spp., or *Olsenella* spp.

A zinc finger nuclease (ZFN) comprises a DNA-binding domain and a DNA-cleavage domain, wherein the DNA binding domain is comprised of at least one zinc finger and is operatively linked to a DNA-cleavage domain. The zinc finger DNA-binding domain is at the N-terminus of the protein and the DNA-cleavage domain is located at the C-terminus of said protein.

A ZFN must have at least one zinc finger. In embodiments, a ZFN would have at least three zinc fingers in order to have sufficient specificity to be useful for targeted genetic recombination in a host cell or organism. Typically, a ZFN having more than three zinc fingers would have progressively greater specificity with each additional zinc finger.

The zinc finger domain can be derived from any class or type of zinc finger. In a particular embodiment, the zinc finger domain comprises the Cis2His2 type of zinc finger that is very generally represented, for example, by the zinc finger transcription factors TFIIIA or Sp1. In embodiments, the zinc finger domain comprises three Cis2His2 type zinc fingers. The DNA recognition and/or the binding specificity of a ZFN can be altered in order to accomplish targeted genetic recombination at any chosen site in cellular DNA. Such modification can be accomplished using known molecular biology and/or chemical synthesis techniques (see, for example, Bibikova et al., 2002).

The ZEN DNA-cleavage domain is derived from a class of non-specific DNA cleavage domains, for example the DNA-cleavage domain of a Type II restriction enzyme such as Fold (Kim et al., 1996). Other useful endonucleases may include, for example, HhaI, HindIII, Nod, BbvCI, EcoRI, BglI, and AlwI.

A transcription activator-like (TAL) effector nuclease (TALEN) comprises a TAL effector DNA binding domain and an endonuclease domain. TAL effectors are proteins of plant pathogenic bacteria that are injected by the pathogen into the plant cell, where they travel to the nucleus and function as transcription factors to turn on specific plant genes. The primary amino acid sequence of a TAL effector dictates the nucleotide sequence to which it binds. Thus, target sites can be predicted for TAL effectors, and TAL effectors can be engineered and generated for the purpose of binding to particular nucleotide sequences.

Fused to the TAL effector-encoding nucleic acid sequences are sequences encoding a nuclease or a portion of a nuclease, typically a nonspecific cleavage domain from a type II restriction endonuclease such as FokI (Kim et al., 1996). Other useful endonucleases may include, for example, HhaI, HindIII, Nod, BbvCI, EcoRI, BglI, and AhvI. The fact that some endonucleases (e.g., FokI) only function as dimers can be capitalized upon to enhance the target specificity of the TAL effector. For example, in some cases each FokI monomer can be fused to a TAL effector sequence that recognizes a different DNA target sequence, and only when the two recognition sites are in close proximity do the inactive monomers come together to create a functional enzyme. By requiring DNA binding to activate the nuclease, a highly site-specific restriction enzyme can be created.

A sequence-specific TALEN can recognize a particular sequence within a preselected target nucleotide sequence present in a cell. Thus, in some embodiments, a target nucleotide sequence can be scanned for nuclease recognition sites, and a particular nuclease can be selected based on the target sequence. In other cases, a TALEN can be engineered to target a particular cellular sequence.

A genome edited population of plants may be screened directly for the PPO genotype or indirectly by screening for a phenotype that results from mutations in the PPO gene. Screening directly for the genotype can include assaying for the presence of mutations in the PPO gene, which may be observed in PCR assays by the absence of specific PPO markers. Screening for the phenotype can comprise screening for a loss or reduction in amount of one or more PPO proteins by ELISA or affinity chromatography, or reduced PPO activity in the grain.

Identified mutations may then be introduced into desirable genetic backgrounds by crossing the mutant with a plant of the desired genetic background and performing a suitable number of backcrosses to cross out the originally undesired parent background.

In the context of this disclosure, an "induced mutation" or "introduced mutation" is an artificially induced genetic variation which may be the result of chemical, radiation or biologically-based mutagenesis, for example genome editing. In certain embodiments, the mutations are null mutations such as nonsense mutations, frameshift mutations, deletions, insertional mutations or splice-site variants which completely inactivate the gene. In certain other embodiments, the mutations are partial mutations which retain some PPO activity, but less than wild-type levels of the enzyme. Nucleotide insertional derivatives include 5' and 3' terminal fusions as well as intra-sequence insertions of single or multiple nucleotides. Insertional nucleotide sequence variants are those in which one or more nucleotides are introduced into a site in the nucleotide sequence, either at a predetermined site as is possible with the CRISPR/Cas system or other genome editing methods, or by random insertion with suitable screening of the resulting product. Deletional variants are characterized by the removal of one or more nucleotides from the sequence. Preferably, a mutant gene has only a single insertion or deletion of a sequence of nucleotides relative to the wild-type gene. The deletion may be extensive enough to include one or more exons or introns, both exons and introns, an intron-exon boundary, a part of the promoter, the translational start site, or even the entire gene. Insertions or deletions within the exons of the protein coding region of a gene which insert or delete a number of nucleotides which is not an exact multiple of three, thereby causing a change in the reading frame during translation, almost always abolish activity of the mutant gene comprising such insertion or deletion.

Substitutional nucleotide variants are those in which at least one nucleotide in the sequence has been removed and a different nucleotide inserted in its place. The preferred number of nucleotides affected by substitutions in a mutant gene relative to the wild-type gene is a maximum of ten nucleotides, more preferably a maximum of 9, 8, 7, 6, 5, 4, 3, or 2, or most preferably only one nucleotide. Substitutions may be "silent" in that the substitution does not change the amino acid defined by the codon. Nucleotide substitutions may reduce the translation efficiency and thereby reduce the PPO expression level, for example by reducing the mRNA stability or, if near an exon-intron splice boundary, alter the splicing efficiency. Silent substitutions that do not alter the translation efficiency of a PPO gene are not expected to alter the activity of the genes and are therefore regarded herein as non-mutant, i.e. such genes are active variants and not encompassed in "mutant alleles". Alternatively, the nucleotide substitution(s) may change the encoded amino acid sequence and thereby alter the activity of the encoded enzyme, particularly if conserved amino acids are substituted for another amino acid which is quite different i.e. a non-conservative substitution.

A conservative amino acid substitution is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Such substitutions would not be made for conserved amino acid residues, or for amino acid residues residing within a conserved motif. Conservative substitution tables are well known in the art (see for example Creighton (1984) Proteins. W. H. Freeman and Company (Eds).

The term "mutation" as used herein does not include silent nucleotide substitutions which do not affect the activity of the gene, and therefore includes only alterations in the gene sequence which affect the gene activity. The term "polymorphism" refers to any change in the nucleotide sequence including such silent nucleotide substitutions. Screening methods may first involve screening for polymorphisms and secondly for mutations within a group of polymorphic variants.

As is understood in the art, hexaploid wheat such as bread wheat comprises three genomes which are commonly designated the A, B and D genomes, while tetraploid wheats such as durum wheat comprise two genomes commonly designated the A and B genomes. Each genome comprises 7 pairs of chromosomes which may be observed by cytological methods during meiosis and thus identified, as is well known in the art.

The terms "plant(s)" and "wheat plant(s)" as used herein as a noun generally refer to whole plants, but when "plant" or "wheat" is used as an adjective, the terms refer to any substance which is present in, obtained from, derived from, or related to a plant or a wheat plant, such as for example, plant organs (e.g. leaves, stems, roots, flowers), single cells (e.g. pollen), seeds, plant cells including for example tissue cultured cells, products produced from the plant such as "wheat flour", "wheat grain", and the like. Plantlets and germinated seeds from which roots and shoots have emerged are also included within the meaning of "plant".

The term "plant parts" as used herein refers to one or more plant tissues or organs which are obtained from a whole plant. Plant parts include vegetative structures (for example, leaves, stems), roots, floral organs/structures, seed (including embryo, endosperm, and seed coat), plant tissue (for example, vascular tissue, ground tissue, and the like), cells and progeny of the same. A progeny plant can be from any filial generation, e.g., F1, F2, F3, F4, F5, F6, F7, etc. The term "plant cell" as used herein refers to a cell obtained from a plant or in a plant, and includes protoplasts or other cells derived from plants, gamete-producing cells, and cells which regenerate into whole plants. Plant cells may be cells in culture. By "plant tissue" is meant differentiated tissue in a plant or obtained from a plant ("explant") or undifferentiated tissue derived from immature or mature embryos, seeds, roots, shoots, fruits, pollen, and various forms of aggregations of plant cells in culture, such as calli. Plant tissues in or from seeds such as wheat seeds are seed coat, endosperm, scutellum, aleurone layer and embryo.

In some embodiments, plant cells of the present disclosure are capable of regenerating a plant or plant part. In other embodiments, plant cells are not capable of regenerating a plant or plant part. Examples of cells not capable of regenerating a plant include, but are not limited to, endosperm, seed coat (testa and pericarp), and root cap.

Cereals as used herein means plants or grain of the monocotyledonous family Poaceae which are cultivated for the edible components of their seeds, and includes wheat, barley, maize, oats, rye, rice, sorghum, triticale, millet, and buckwheat. In certain embodiments, the plant or grain is a Triticeae plant or grain (e.g., wheat, barley, or rye). In certain embodiments, the plant or grain is a wheat plant or grain.

As used herein, the term "wheat" refers to any species of the Genus *Triticum*, including progenitors thereof, as well as progeny thereof produced by crosses with other species. Wheat includes "hexaploid wheat" which has genome organization of AABBDD, comprised of 42 chromosomes, and "tetraploid wheat" which has genome organization of AABB, comprised of 28 chromosomes. Hexaploid wheat includes *T. aestivum, T. spelta, T. macha, T. compactum, T. sphaerococcum, T. vavilovii*, and interspecies cross thereof. Tetraploid wheat includes *T. durum* (also referred to as durum wheat or *Triticum turgidum* ssp. durum), *T. dicoccoides, T. dicoccum, T. polonicum*, and interspecies cross thereof. In addition, the term "wheat" includes possible progenitors of hexaploid or tetraploid *Triticum* sp. such as *T. uartu, T. monococcum* or *T. boeoticum* for the A genome, *Aegilops speltoides* for the B genome, and *T. tauschii* (also known as *Aegilops squarrosa* or *Aegilops tauschii*) for the D genome. A wheat cultivar for use in the present disclosure may belong to, but is not limited to, any of the above-listed species. Also encompassed are plants that are produced by conventional techniques using *Triticum* sp. as a parent in a sexual cross with a non-*Triticum* species, such as rye *Secale cereale*, including but not limited to Triticale. In certain embodiments, the wheat plant is suitable for commercial production of grain, such as commercial varieties of hexaploid wheat or durum wheat, having suitable agronomic characteristics which are known to those skilled in the art. In certain embodiments, the wheat is *Triticum aestivum* ssp. *aestivum* or *Triticum turgidum* ssp. *durum.*

As used herein, the term "barley" refers to any species of the genus *Hordeum*, including progenitors thereof, as well as progeny thereof produced by crosses with other species. In certain embodiments, the plant is of a *Hordeum* species which is commercially cultivated such as, for example, a strain or cultivar or variety of *Hordeum vulgare* or suitable for commercial production of grain.

As used herein, the term "rye" refers to any species of the genus *Secale*, including progenitors thereof, as well as progeny thereof produced by crosses with other species. In certain embodiments, the plant is of a *Secale* species which is commercially cultivated such as, for example, a strain or cultivar or variety of *Secale cereale* or suitable for commercial production of grain.

The plants of the disclosure may be crossed with plants containing a more desirable genetic background, and therefore the disclosure includes the transfer of the reduced browning trait to other genetic backgrounds. After the initial crossing, a suitable number of backcrosses may be carried out to remove a less desirable background. PPO1 or PPO2 allele-specific PCR-based markers such as those described herein may be used to screen for or identify progeny plants or grain with the desired combination of alleles, thereby tracking the presence of the alleles in the breeding program. The desired genetic background may include a suitable combination of genes providing commercial yield and other characteristics such as agronomic performance or abiotic stress resistance. The genetic background may comprise one or more transgenes such as, for example, a gene that confers tolerance to an herbicide such as glyphosate. The desired genetic background of the plant will include considerations of agronomic yield and other characteristics. Such characteristics might include growth habit, agronomic performance, disease resistance and abiotic stress resistance.

Marker assisted selection is a well-recognized method of selecting for heterozygous plants obtained when backcrossing with a recurrent parent in a classical breeding program. The population of plants in each backcross generation will be heterozygous for the gene(s) of interest normally present in a 1:1 ratio in a backcross population, and the molecular marker can be used to distinguish the two alleles of the gene. By extracting DNA from, for example, young shoots and testing with a specific marker for the introgressed desirable trait, early selection of plants for further backcrossing is made whilst energy and resources are concentrated on fewer plants.

Procedures such as crossing plants, self-fertilizing plants or marker-assisted selection are standard procedures and well known in the art. Transferring alleles from tetraploid wheat such as durum wheat to a hexaploid wheat, or other forms of hybridization, is also known in the art.

The plants of the disclosure may be used in a plant breeding program. The goal of plant breeding is to combine, in a single variety or hybrid, various desirable traits. For field crops, these traits may include, for example, resistance to diseases and insects, tolerance to heat and drought, tolerance to chilling or freezing, reduced time to crop maturity, greater yield and better agronomic quality. With mechanical harvesting of many crops, uniformity of plant characteristics such as germination and stand establishment, growth rate, maturity, and plant height is desirable. Traditional plant breeding is an important tool in developing new and improved commercial crops. This disclosure encompasses methods for producing a plant by crossing a first parent plant with a second parent plant wherein one or both of the parent plants is a plant displaying a phenotype as described herein.

Plant breeding techniques known in the art and used in a plant breeding program include, but are not limited to, recurrent selection, bulk selection, mass selection, backcrossing, pedigree breeding, open pollination breeding, restriction fragment length polymorphism enhanced selection, genetic marker enhanced selection, doubled haploids and transformation. Often combinations of these techniques are used.

To identify the desired phenotypic characteristic, plants that contain a mutant PPO1 or PPO2 allele or other desired genes are typically compared to control plants. When evaluating a phenotypic characteristic associated with enzyme activity such as PPO activity in the grain, the plants to be tested and control plants are grown under growth chamber, greenhouse, open top chamber and/or field conditions. Identification of a particular phenotypic trait and comparison to controls is based on routine statistical analysis and scoring. Statistical differences between plants lines can be assessed by comparing, for example, enzyme activity between plant lines within each tissue type expressing the enzyme.

As used herein, "modified", in the context of plants, seeds, plant components, plant cells, and plant genomes, refers to a state containing changes or variations from their natural or native state. For instance, a "native transcript" of a gene refers to an RNA transcript that is generated from an unmodified gene. Typically, a native transcript is a sense transcript. Modified plants or seeds contain molecular changes in their genetic materials, including either genetic or epigenetic modifications. Typically, modified plants or seeds, or a parental or progenitor line thereof, have been subjected to mutagenesis, genome editing (e.g., without being limiting, via methods using site-specific nucleases), genetic transformation (e.g., without being limiting, via methods of *Agrobacterium* transformation or microprojectile bombardment), or a combination thereof. In one embodiment, a modified plant provided herein comprises no non-plant genetic material or sequences. In yet another embodiment, a modified plant provided herein comprises no interspecies genetic material or sequences.

In certain embodiments, the plants, plant parts and products therefrom of the disclosure are non-transgenic for genes that inhibit expression of PPO1 or PPO2 (e.g., they do not comprise a transgene encoding an RNA molecule that reduces expression of the endogenous PPO1 or PPO2 genes). In certain embodiments, they may comprise other transgenes, e.g., herbicide tolerance genes. In certain embodiments, the plant, plant parts and products therefrom are non-transgenic, i.e., they do not contain any transgene.

The terms "transgenic plant" as used herein refer to a plant that contains a genetic construct ("transgene") not found in a wild-type plant of the same species, variety or cultivar. That is, transgenic plants (transformed plants) contain genetic material that they did not contain prior to the transformation. A "transgene" as referred to herein has the normal meaning in the art of biotechnology and refers to a genetic sequence which has been produced or altered by recombinant DNA or RNA technology and which has been introduced into the plant cell. The transgene may include genetic sequences obtained from or derived from a plant cell, or another plant cell, or a non-plant source, or a synthetic sequence. Typically, the transgene has been introduced into the plant by human manipulation such as, for example, by transformation but any method can be used as one of skill in the art recognizes. A "non-transgenic plant" is one which has not been genetically modified by the introduction of genetic material by recombinant DNA techniques.

Any of several methods may be employed to determine the presence of a transgene in a transformed plant. For example, polymerase chain reaction (PCR) may be used to amplify sequences that are unique to the transformed plant, with detection of the amplified products by gel electrophoresis or other methods. DNA may be extracted from the plants using conventional methods and the PCR reaction carried out using primers that will distinguish the transformed and non-transformed plants. An alternative method to confirm a positive transformant is by Southern blot hybridization, well known in the art. Wheat plants which are transformed may also be identified i.e. distinguished from non-transformed or wild-type wheat plants by their phenotype, for example conferred by the presence of a selectable marker gene, or by immunoassays that detect or quantify the expression of an enzyme encoded by the transgene, or any other phenotype conferred by the transgene.

In certain embodiments, biological samples from the plants of the disclosure are provided. As used herein, the phrase "biological sample" refers to either intact or non-intact (e.g., milled seed or plant tissue, chopped plant tissue, lyophilized tissue) plant tissue. It may also be an extract comprising intact or non-intact seed or plant tissue. The biological sample can comprise flour, meal, flakes, syrup, oil, starch, and cereals manufactured in whole or in part to contain crop plant by-products. In certain embodiments, the biological sample is "non-regenerable" (i.e., incapable of being regenerated into a plant or plant part).

Several embodiments provide a commodity plant product prepared from the plants of the disclosure. The plants of the present disclosure may be grown or harvested for grain, primarily for use as food for human consumption or as animal feed, or for fermentation or industrial feedstock production such as ethanol production, among other uses. Alternatively, the plants may be used directly as feed. The plants of the present disclosure may be useful for food production and in particular for commercial food production.

The product may be produced at the site where the plant has been grown, the plants and/or parts thereof may be removed from the site where the plants have been grown to produce the product. Typically, the plant is grown, the desired harvestable parts are removed from the plant, if feasible in repeated cycles, and the product made from the harvestable parts of the plant. The step of growing the plant may be performed only once each time the method is performed, while allowing repeated times the steps of product production e.g. by repeated removal of harvestable parts of the plants of the disclosure and if necessary further processing of these parts to arrive at the product. It is also possible that the step of growing the plants is repeated and plants or harvestable parts are stored until the production of the product is then performed once for the accumulated plants or plant parts. Also, the steps of growing the plants and producing the product may be performed with an overlap in time, even simultaneously to a large extent or sequentially. Generally, the plants are grown for some time before the product is produced.

Wheat may be used to produce a variety of products, including, but not limited to, grain, flour, baked goods, cereals, crackers, pasta, beverages, livestock feed, biofuel, straw, construction materials, and starches. The hard wheat classes are milled into flour used for breads, while the soft wheat classes are milled into flour used for pastries and crackers. Wheat starch is used in the food and paper industries as laundry starches, among other products.

The disclosure thus provides flour, meal or other products produced from wheat grain of the present disclosure. These may be unprocessed or processed, for example by fractionation or bleaching, or heat treated to stabilize the product such as flour. The disclosure includes methods of producing flour, meal, starch granules, or starch from the grain or from an intermediate product such as flour. Such methods include, for example, milling, grinding, rolling, flaking or cracking the grain.

The present disclosure also extends to wheat flour, such as wholemeal wheat flour, or other processed products obtained from the grain such as semolina, isolated wheat starch granules, isolated wheat starch or wheat bran produced from the grain of the disclosure. In an embodiment, the flour is wheat endosperm flour (white flour). The white flour has a lower bran content than the wholemeal flour from which it is obtained. The flour or bran may have been stabilized by heat treatment.

The present disclosure also provides a food ingredient that comprises the grain or flour. In certain embodiments, the food or drink ingredient is packaged ready for sale. The food or drink ingredient may be incorporated into a mixture with another food or drink ingredient, such as, for example, a cake mix, a pancake mix or a dough. The food ingredient may be used in a food product at a level of at least 1%, preferably at least 10%, on a dry weight basis, and the drink ingredient may be used in a drink product at a level of at least 0.1% on a weight basis. If the food product is a breakfast cereal, bread, cake or other farinaceous product, higher incorporation rates are preferred, such as at a level of at least 20% or at least 30%. Up to 100% of the ingredient (grain, flour such as wholemeal flour etc.) in the food product may be an ingredient of the disclosure.

The grain of the present disclosure and the ingredients obtained therefrom may be blended with essentially wild-type grain or other ingredients. The disclosure therefore provides a composition comprising traditional wheat grain or an ingredient obtained therefrom in addition to the wheat grain of the disclosure, or an ingredient obtained therefrom. In such compositions, it is preferred that the grain of the present disclosure and/or the ingredient obtained therefrom comprises at least 10% by weight of the composition. The traditional wheat grain ingredient may be, for example, flour such as wholemeal flour, semolina, a starch-containing ingredient, purified starch or bran.

The grain of the present disclosure may also be milled to produce a milled wheat product. This will typically involve obtaining wheat grain, milling the grain to produce flour, and optionally, separating any bran from the flour. Milling the grain may be by dry milling or wet milling. The grain may be conditioned to having a desirable moisture content prior to milling, preferably about 10% or about 14% on a weight basis, or the milled product such as flour or bran may be processed by treatment with heat to stabilize the milled product. As will be understood, the PPO activity and browning of the milled product corresponds to the PPO activity of the wheat grain or the component of the wheat grain which is represented in the milled product.

Browning may be determined by known methods including, but not limited to, spectroscopy (e.g., light absorption, laser-induced fluorescence spectroscopy, time-delayed integration spectroscopy, large aperture spectrometer); colorimetry (e.g., tristimulus, spectrocolorimeter); and visual inspection/scoring.

The present disclosure also provides a method of producing a product, wherein the method comprises processing a wheat plant of the disclosure to obtain the product. In certain embodiments, the method comprises (i) obtaining or producing a wheat grain of the present disclosure, or flour therefrom, and (ii) processing the wheat grain or flour therefrom to produce the product.

In certain embodiments, the whole grain flour, the coarse fraction, or the refined flour may be a component (ingredient) of a food product and may be used to produce a food product. For example, the food product may be a bagel, a biscuit, a bread, a bun, a croissant, a dumpling, an English muffin, a muffin, a pita bread, a quickbread, a refrigerated/frozen dough product, dough, baked beans, a burrito, chili, a taco, a tamale, a tortilla, a pot pie, a ready to eat cereal, a ready to cat meal, stuffing, a microwaveable meal, a brownie, a cake, a cheesecake, a coffee cake, a cookie, a dessert, a pastry, a sweet roll, a candy bar, a pie crust, pie filling, baby food, a baking mix, a batter, a breading, a gravy mix, a meat extender, a meat substitute, a seasoning mix, a soup mix, a gravy, a roux, a salad dressing, a soup, sour cream, a noodle, a pasta, ramen noodles, chow mein noodles, lo mein noodles, an ice cream inclusion, an ice cream bar, an ice cream cone, an ice cream sandwich, a cracker, a crouton, a doughnut, an egg roll, an extruded snack, a fruit and grain bar, a microwaveable snack product, a nutritional bar, a pancake, a par-baked bakery product, a pretzel, a pudding, a granola-based product, a snack chip, a snack food, a snack mix, a waffle, a pizza crust, chapatti, roti, naan, animal food or pet food.

As used herein, the term "grain" generally refers to mature, harvested seed of a plant but can also refer to grain after imbibition or germination, according to the context. Mature cereal grain such as wheat commonly has a moisture content of less than about 18-20%. As used herein, the term "seed" includes harvested seed but also includes seed which is developing in the plant post anthesis and mature seed comprised in the plant prior to harvest.

In certain embodiments, the PPO activity in the grain is reduced by at least 10%, at least 20%, at least 30%, at least 40%, at least 50%, at least 60%, at least 70%, at least 80%, at least 90%, or at least 95% relative to that of corresponding wild-type (i.e., non-modified) grain. In certain embodiments, the PPO activity in the grain is reduced by about 10% to about 90%, about 20% to about 80%, or about 30% to about 70% relative to that of corresponding wild-type (i.e., non-modified) grain.

The terms "polypeptide" and "protein" are generally used interchangeably herein. The terms "proteins" and "polypeptides" as used herein also include variants, mutants, modifications and/or derivatives of the polypeptides of the disclosure as described herein. As used herein, "substantially purified polypeptide" refers to a polypeptide that has been separated from the lipids, nucleic acids, other peptides and other molecules with which it is associated in its native state. In certain embodiments, the substantially purified polypeptide is at least 60% free, at least 75% free, or at least 90% free from other components with which it is naturally associated. By "recombinant polypeptide" is meant a polypeptide made using recombinant techniques, i.e., through the expression of a recombinant polynucleotide in a cell.

With regard to a defined polypeptide, it will be appreciated that % identity figures higher than those provided above will encompass preferred embodiments. Thus, where applicable, in light of the minimum % identity figures, it is preferred that the polypeptide comprises an amino acid sequence which is at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Methods of alignment of sequences for comparison are well known in the art and can be accomplished using mathematical algorithms such as the algorithm of Myers and Miller (1988) CABIOS 4:11-17; the local alignment algorithm of Smith et al. (1981) Adv. Appl. Math. 2:482; the global alignment algorithm of Needleman and Wunsch (1970) J. Mol. Biol. 48:443-453; and the algorithm of Karlin and Altschul (1990) Proc. Natl. Acad. Sci. U.S. Pat. No. 872,264, modified as in Karlin and Altschul (1993) Proc. Natl. Acad. Sci. USA 90:5873-5877. Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA).

Amino acid sequence mutants of the polypeptides of the present disclosure can be prepared by introducing appropriate nucleotide changes into a nucleic acid of the present disclosure. Such mutants include, for example, deletions, insertions, or substitutions of residues within the amino acid sequence. Amino acid sequence deletions generally range from about 1 to 15 residues, about 1 to 10 residues, or about 1 to 5 contiguous residues. Substitution mutants have at least one amino acid residue in the polypeptide molecule removed and a different residue inserted in its place. The sites of greatest interest for substitutional mutagenesis include sites identified as the active site(s). Other sites of interest are those in which particular residues obtained from various strains or species are identical i.e., conserved amino acids. These positions may be important for biological activity. Non-conservative substitutions in a PPO polypeptide are expected to reduce the activity of the enzyme and many may correspond to a PPO polypeptide encoded by a partial loss of function mutant.

As used herein with respect to polypeptides, the term “fragment” or “portion” can refer to a polypeptide that is reduced in length relative to a reference polypeptide and that comprises or consists of an amino acid sequence of contiguous amino acids identical or almost identical (e.g., 90%, 91%, 92%, 93%, 94%, 95%, 96%, 97%, 98%, 99% identical) to a corresponding portion of the reference polypeptide. Such a polypeptide fragment can be, where appropriate, included in a larger polypeptide of which it is a constituent. In some embodiments, the polypeptide fragment comprises, consists essentially of, or consists of at least about 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 125, 150, 175, 200, 225, 250, 260, 270, 280, 290, 300, 350, 400 or more consecutive amino acids of a reference polypeptide. An example of a PPO polypeptide fragment is SEQ ID NO: 35, which is a CuB domain of a PPO polypeptide.

As used herein, the term “gene” includes any deoxyribonucleotide sequence which includes a protein coding region or which is transcribed in a cell but not translated, together with associated non-coding and regulatory regions. Such associated regions are typically located adjacent to the coding region on both the 5' and 3' ends for a distance of about 2 kb on either side. The sequences which are located 5' of the protein coding region and which are present on the mRNA are referred to as 5' non-translated sequences. The sequences which are located 3' or downstream of the protein coding region and which are present on the mRNA are referred to as 3' non-translated sequences. The term “gene” encompasses both cDNA and genomic forms of a gene. The term “gene” includes synthetic or fusion molecules encoding the proteins of the disclosure described herein. An “endogenous gene” refers to a native gene in its natural location in the genome of an organism.

A genomic form or clone of a gene containing the coding region may be interrupted with non-coding sequences termed “introns” or “intervening regions” or “intervening sequences.” An “intron” as used herein is a segment of a gene which is transcribed as part of a primary RNA transcript but is not present in the mature mRNA molecule. Introns are removed or “spliced out” from the nuclear or primary transcript; introns therefore are absent in the messenger RNA (mRNA). Introns may contain regulatory elements such as enhancers. “Exons” as used herein refer to the DNA regions corresponding to the RNA sequences which are present in the mature mRNA or the mature RNA molecule in cases where the RNA molecule is not translated. An mRNA functions during translation to specify the sequence or order of amino acids in a nascent polypeptide.

“Regulatory elements” refer to nucleotide sequences located upstream (5' non-coding sequences), within, or downstream (3' non-coding sequences) of a coding sequence, and which influence the transcription, RNA processing or stability, or translation of the associated coding sequence. Regulatory elements may include, but are not limited to, promoters, translation leader sequences, introns, and polyadenylation recognition sequences. Regulatory elements present on a recombinant DNA construct that is introduced into a cell can be endogenous to the cell, or they can be heterologous with respect to the cell. The terms “regulatory element” and “regulatory sequence” are used interchangeably herein.

By “operably linked” or “operably associated,” it is meant that the indicated elements are functionally related to each other, and are also generally physically related. Thus, the term “operably linked” or “operably associated” as used herein, refers to nucleotide sequences on a single nucleic acid molecule that are functionally associated. Therefore, a first nucleotide sequence that is operably linked to a second nucleotide sequence means a situation when the first nucleotide sequence is placed in a functional relationship with the second nucleotide sequence. For instance, a promoter is operably associated with a nucleotide sequence if the promoter affects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, sequences can be present between a promoter and a nucleotide sequence, and the promoter can still be considered "operably linked" to the nucleotide sequence.

The present disclosure refers to various polynucleotides. As used herein, a "polynucleotide" or "nucleic acid" or "nucleic acid molecule" means a polymer of nucleotides, which may be DNA or RNA or a combination thereof, for example a heteroduplex of DNA and RNA, and includes for example mRNA, CRNA, cDNA, RNA, siRNA, shRNA, hpRNA, and single or double-stranded DNA. It may be DNA or RNA of cellular, genomic or synthetic origin, for example made on an automated synthesizer, and may be combined with carbohydrate, lipids, protein or other materials, labelled with fluorescent or other groups, or attached to a solid support to perform a particular activity defined herein. In embodiments, the polynucleotide is solely DNA or solely RNA as occurs in a cell, and some bases may be methylated or otherwise modified as occurs in a wheat cell. The polymer may be single-stranded, essentially double-stranded or partly double-stranded. An example of a partly-double stranded RNA molecule is a hairpin RNA (hpRNA), short hairpin RNA (shRNA) or self-complementary RNA which include a double stranded stem formed by basepairing between a nucleotide sequence and its complement and a loop sequence which covalently joins the nucleotide sequence and its complement. Basepairing as used herein refers to standard basepairing between nucleotides, including G: U basepairs in an RNA molecule. "Complementary" means two polynucleotides are capable of basepairing along part of their lengths, or along the full length of one or both.

By "isolated" is meant material that is substantially or essentially free from components that normally accompany it in its native state. As used herein, an "isolated polynucleotide" or "isolated nucleic acid molecule" means a polynucleotide which is at least partially separated from, preferably substantially or essentially free of, the polynucleotide sequences of the same type with which it is associated or linked in its native state. For example, an "isolated polynucleotide" includes a polynucleotide which has been purified or separated from the sequences which flank it in a naturally occurring state, e.g., a DNA fragment which has been removed from the sequences which are normally adjacent to the fragment. In certain embodiments, the isolated polynucleotide is also at least 90% free from other components such as proteins, carbohydrates, lipids etc. The term "recombinant polynucleotide" as used herein refers to a polynucleotide formed in vitro by the manipulation of nucleic acid into a form not normally found in nature. For example, the recombinant polynucleotide may be in the form of an expression vector. Generally, such expression vectors include transcriptional and translational regulatory nucleic acid operably connected to the nucleotide sequence to be transcribed in the cell.

The present disclosure refers to use of oligonucleotides which may be used as "probes" or "primers". The term "primer" as used herein encompasses any nucleic acid that is capable of priming the synthesis of a nascent nucleic acid in a template-dependent process, such as PCR. Typically, primers are oligonucleotides from 10 to 30 nucleotides in length, but longer sequences may be used. Primers may be provided in single or double-stranded form. Probes may be used as primers, but are designed to bind to the target DNA or RNA and need not be used in an amplification process.

As used herein, "oligonucleotides" are polynucleotides up to 50 nucleotides in length. They can be RNA, DNA, or combinations or derivatives of either. Oligonucleotides are typically relatively short single stranded molecules of 10 to 30 nucleotides, commonly 15-25 nucleotides in length, typically comprised of 10-30 or 15-25 nucleotides which are identical to, or complementary to, part of a PPO1 or PPO2 gene or cDNA corresponding to a PPO1 or PPO2 gene. When used as a probe or as a primer in an amplification reaction, the minimum size of such an oligonucleotide is the size required for the formation of a stable hybrid between the oligonucleotide and a complementary sequence on a target nucleic acid molecule. In certain embodiments, the oligonucleotides are at least 15 nucleotides, at least 18 nucleotides, at least 19 nucleotides, at least 20 nucleotides, or at least 25 nucleotides in length. Polynucleotides used as a probe are typically conjugated with a detectable label such as a radioisotope, an enzyme, biotin, a fluorescent molecule, or a chemiluminescent molecule. Oligonucleotides and probes of the disclosure are useful in methods of detecting an allele of a PPO1 or PPO2 gene or other gene associated with a trait of interest, for example reduced browning. Such methods employ nucleic acid hybridization and, in many instances, include oligonucleotide primer extension by a suitable polymerase, for example as used in PCR for detection or identification of wild-type or mutant alleles. In certain embodiments, the oligonucleotides and probes hybridize to a PPO1 or PPO2 gene sequence from wheat, including any of the sequences disclosed herein. In certain embodiments, the oligonucleotide pairs span one or more introns, or a part of an intron and therefore may be used to amplify an intron sequence in a PCR reaction.

As used herein with respect to nucleic acids, the term "fragment" or "portion" refers to a nucleic acid that is reduced in length (e.g., reduced by 1, 2, 3, 4, 5, 6, 7, 8, 9, 10, 11, 12, 13, 14, 15, 16, 17, 18, 19, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 400, 450, 500, 550, 600, 650, 700, 750, 800, 850, 900, 950 or 1000 or more nucleotides or any range or value therein) relative to a reference nucleic acid and that comprises or consists of a nucleotide sequence of contiguous nucleotides identical or almost identical (e.g., 80%, 81%, 82%, 83%, 84%, 85%, 86%, 87%, 88%, 89%, 90%, 91%, 92%, 93%, 94%, 95%, 96%, 97%, 98%, 99% identical) to a corresponding portion of the reference nucleic acid. Such a nucleic acid fragment can be, where appropriate, included in a larger polynucleotide of which it is a constituent.

As an example, a "fragment" or "portion" of a nucleic acid encoding a PPO1 or PPO2 gene can be about 10, 15, 20, 25 30, 35, 40, 45, 50, 55, 60, 65, 70, 75, 80, 85, 90, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 420, 440, 460, 480, 500, 520, 540, 560, 580, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 3000, 3250, 3500, 3750, or 4000 or more consecutive nucleotides of a PPO1 or PPO2 gene, or any range or value therein (optionally, about 10, 20, 30, 40, 50, 100, 150, 300 to about 3000, 3250, 3500, 3600, 3700, 3800, 3900, or 4000 consecutive nucleotides; about 10, 20, 30, 40 to about 50, 60, 70, 80, 90, 100, 110, 120, 130, 140, 150, 200, 250 or 300 consecutive nucleotides, or about 50, 55, 60, 65, 70, 75, 80, 85 to about 90, 100, 105, 110, 115, 120, 125, 130, 135, 140 consecutive nucleotides; e.g., about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 132, 123, 124, 125, 126, 127, 128, 129, 130, 131, 132, 133, 134, 135, 136, 137, 138, 139, or 140 consecutive nucleotides). In some embodiments, the one or more consecutive nucleotides of a PPO1 or PPO2 gene can be from a region encoding a CuB domain of a PPO polypeptide.

The terms "polynucleotide variant" and "variant" and the like refer to polynucleotides displaying substantial sequence identity with a reference polynucleotide sequence and which are able to function in an analogous manner to, or with the same activity as, the reference sequence. These terms also encompass polynucleotides that are distinguished from a reference polynucleotide by the addition, deletion or substitution of at least one nucleotide, or that have, when compared to naturally occurring molecules, one or more mutations. Accordingly, the terms "polynucleotide variant" and "variant" include polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide. Accordingly, these terms encompass polynucleotides that encode polypeptides that exhibit enzymatic or other regulatory activity, or polynucleotides capable of serving as selective probes or other hybridizing agents. The terms "polynucleotide variant" and "variant" also include naturally occurring allelic variants. Mutants can be either naturally occurring (that is to say, isolated from a natural source) or synthetic (for example, by performing site-directed mutagenesis on the nucleic acid). In certain embodiments, a polynucleotide variant of the disclosure which encodes a polypeptide with enzyme activity is greater than 400, greater than 500, greater than 600, greater than 700, greater than 800, greater than 900, or greater than 1,000 nucleotides in length, up to the full length of the gene.

A variant of an oligonucleotide of the disclosure includes molecules of varying sizes which are capable of hybridizing, for example, to the wheat genome at a position close to that of the specific oligonucleotide molecules defined herein. For example, variants may comprise additional nucleotides (such as 1, 2, 3, 4, or more), or less nucleotides as long as they still hybridize to the target region. Furthermore, a few nucleotides may be substituted without influencing the ability of the oligonucleotide to hybridize to the target region. In addition, variants may readily be designed which hybridize close (for example, but not limited to, within 50 nucleotides) to the region of the plant genome where the specific oligonucleotides defined herein hybridize.

By "corresponds to" or "corresponding to" in the context of polynucleotides or polypeptides is meant a polynucleotide (a) having a nucleotide sequence that is substantially identical or complementary to all or a portion of a reference polynucleotide sequence or (b) encoding an amino acid sequence identical to an amino acid sequence in a peptide or protein. This phrase also includes within its scope a peptide or polypeptide having an amino acid sequence that is substantially identical to a sequence of amino acids in a reference peptide or protein. Terms used to describe sequence relationships between two or more polynucleotides or polypeptides include "reference sequence", "comparison window", "sequence identity", "percentage of sequence identity", "substantial identity" and "identical", and are defined with respect to a defined minimum number of nucleotides or amino acid residues or over the full length. The terms "sequence identity" and "identity" are used interchangeably herein to refer to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, U) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

Nucleotide or amino acid sequences are indicated as "essentially similar" when such sequences have a sequence identity of at least about 95%, particularly at least about 98%, more particularly at least about 98.5%, quite particularly about 99%, especially about 99.5%, more especially about 100%, quite especially are identical. It is clear that when RNA sequences are described as essentially similar to, or have a certain degree of sequence identity with, DNA sequences, thymine (T) in the DNA sequence is considered equal to uracil (U) in the RNA sequence.

With regard to the defined polynucleotides, it will be appreciated that % identity figures higher than those provided above will encompass preferred embodiments. Thus, where applicable, in light of the minimum % identity figures, it is preferred that the polynucleotide comprises a polynucleotide sequence which is at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

In certain embodiments, the present disclosure refers to the stringency of hybridization conditions to define the extent of complementarity of two polynucleotides. "Stringency" as used herein, refers to the temperature and ionic strength conditions, and presence or absence of certain organic solvents, during hybridization. The higher the stringency, the higher will be the degree of complementarity between a target nucleotide sequence and the labelled polynucleotide sequence. "Stringent conditions" refers to temperature and ionic conditions under which only nucleotide sequences having a high frequency of complementary bases will hybridize. As used herein, the term "hybridizes under low stringency, medium stringency, high stringency, or very high stringency conditions" describes conditions for hybridization and washing. Guidance for performing hybridization reactions can be found in Current Protocols in Molecular Biology, John Wiley & Sons, N.Y. (1989), 6.3.1-6.3.6, herein incorporated by reference. Specific hybridization conditions referred to herein are as follows: 1) low stringency hybridization conditions in 6× sodium chloride/sodium citrate (SSC) at about 45° C., followed by two washes in 0.2×SSC, 0.1% SDS at 50-55° C.; 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and 4) very high stringency hybridization conditions are 0.5 M sodium phosphate, 7% SDS at 65° C., followed by one or more washes at 0.2×SSC, 1% SDS at 65° C.

Different nucleic acids or proteins having homology are referred to herein as "homologs" (also spelled "homologues"). The term homolog includes homologous sequences from the same and from other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the disclosure further comprise homologues to the nucleotide sequences and polypeptide sequences of this disclosure. "Orthologous," as used herein, refers to homologous nucleotide sequences and/or amino acid sequences in different species that arose from a common ancestral gene during speciation. A homolog of a nucleotide sequence of this disclosure has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to the nucleotide sequence of the disclosure.

As used herein, the phrase "substantially identical," or "substantial identity" in the context of two nucleic acid molecules, nucleotide sequences or polypeptide sequences, refers to two or more sequences or subsequences that have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% nucleotide or amino acid residue identity, when compared and aligned for maximum correspondence, as measured using one of the following sequence comparison algorithms or by visual inspection. In some embodiments, the substantial identity exists over a region of consecutive nucleotides of a nucleotide sequence of the disclosure that is about 10 nucleotides to about 20 nucleotides, about 10 nucleotides to about 25 nucleotides, about 10 nucleotides to about 30 nucleotides, about 15 nucleotides to about 25 nucleotides, about 30 nucleotides to about 40 nucleotides, about 50 nucleotides to about 60 nucleotides, about 70 nucleotides to about 80 nucleotides, about 90 nucleotides to about 100 nucleotides, about 100 nucleotides to about 200 nucleotides, about 100 nucleotides to about 300 nucleotides, about 100 nucleotides to about 400 nucleotides, about 100 nucleotides to about 500 nucleotides, about 100 nucleotides to about 600 nucleotides, about 100 nucleotides to about 800 nucleotides, about 100 nucleotides to about 900 nucleotides, about 500 nucleotides to about 1000 nucleotides, about 500 nucleotides to about 1500 nucleotides, about 500 nucleotides to about 2000 nucleotides, about 1000 nucleotides to about 2000 nucleotides, about 1000 nucleotides to about 3000 nucleotides, or about 1500 nucleotides to about 4000 nucleotides, or more nucleotides in length, and any range therein, up to the full length of the sequence. In some embodiments, nucleotide sequences can be substantially identical over at least about 20 consecutive nucleotides (e.g., about 20, 21, 22, 23, 24, 25, 26, 27, 28, 29, 30, 31, 32, 33, 34, 35, 36, 37, 38, 39, 40, 50, 60, 70, 80, 90, 100, 200, 300, 400, 500, 600, 700, 800, 900, 1000, 1100, 1200, 1300, 1400, 1500, 1600, 1700, 1800, 1900, 2000, 2100, 2200, 2300, 2500, 3000, 3500, 4000, 4500, or 5000 or more nucleotides). In some embodiments, two or more PPO1 or PPO2 genes can be substantially identical to one another over at least about 10, 20, 30, 40, 50, 100, 200, 300, 400, 500, 600, 700, 800, 900, 1000, 1100, 1200, 1300, 1400, or 1500 to about 2000, 2050, 2100, 2150, 2200, 2250, 2300, 2350, 2400, 2450, 2500, 2510, 2520, 2530, 2540, 2550, 2600, 2650, 2700, 2750, 2800, 2850, 2900, 2950, 3000, 3050, 3100, 3150, 3200, 3250, 3300, 3350, 3400, 3450, 3490, 3500, 3600, 3700, 3800, 3900, 4000, 4100, 4200, 4300, 4400, 4500, 4600, 4700, 4800, 4900, 5000, 5250, 5500, 5750, 6000, 6500 or 7000 or more consecutive nucleotides of a PPO1 or PPO2 gene, optionally over about 10, 20, 30, 40, 50, 60, 70, 80, 90, 100, 110, 120, 130, 140, 150, 200, 210, 220, 230, 240, 250, 260, 270, 280, 290, 300, 310, 320, 330, 340, 350, 360, 370, 380, 390, 400, 420, 440, 460, 480 or 500 consecutive nucleotides to about 900, 1000, 1100, 1200, 1300, 1400, 1500, 1600, 1700, 1800, 1900, 2000, 2100, 2200, 2300, 2400, 2500, 3000, 3500, 4000, 4500, or 5000 or more consecutive nucleotides of a PPO1 or PPO2 gene.

In some embodiments, the substantial identity exists over a region of consecutive amino acid residues of a polypeptide of the disclosure that is about 3 amino acid residues to about 10, 11, 12, 13, 14, 15, 16, 17, 18, 19, or 20 amino acid residues, about 5 amino acid residues to about 25, 30, 35, 40, 45, 50 or 60 amino acid residues, about 15 amino acid residues to about 30 amino acid residues, about 20 amino acid residues to about 40 amino acid residues, about 25 amino acid residues to about 40 amino acid residues, about 25 amino acid residues to about 50 amino acid residues, about 30 amino acid residues to about 50 amino acid residues, about 40 amino acid residues to about 50 amino acid residues, about 40 amino acid residues to about 70 amino acid residues, about 50 amino acid residues to about 70 amino acid residues, about 60 amino acid residues to about 80 amino acid residues, about 70 amino acid residues to about 80 amino acid residues, about 90 amino acid residues to about 100 amino acid residues, or more amino acid residues in length, and any range therein, up to the full length of the sequence. In some embodiments, polypeptide sequences can be substantially identical to one another over at least about 8, 9, 10, 11, 12, 13, 14, or more consecutive amino acid residues (e.g., about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 130, 140, 150, 175, 200, 225, 250, 275, 300, 325, 350, 400, 450, 500, or more amino acids in length or more consecutive amino acid residues). In some embodiments, two or more PPO polypeptides can be substantially identical to one another over at least about 10 to about 700 or more consecutive amino acid residues of the amino acid sequence of, for example, SEQ ID NO: 15, 16, 17, 18, 19, 20, 21, 26, 27, 32, or 33; e.g., over at least about 10, 11, 12, 13, 14, 15, 16, 17, 18, 19, 20, 25, 30, 35, 40, 45, 50, 60, 70, 71, 72, 73, 74, 75, 76, 77, 78, 79, 80, 85, 90, 95, 100, 105, 110, 120, 125, 130, 135, 140, 145, 150, 155, 160, 165, 170, 175, 200, 205, 210, 215, 220, 225, 230, 235, 240, 245, 250, 255, 260, 265, 270, 275, 280, 290, 300, 350, 400, 450, 500, 550, 600, 650, or 700 or more consecutive amino acid residues of the amino acid sequence of, for example, SEQ ID NO: 15, 16, 17, 18, 19, 20, 21, 26, 27, 32, or 33. In some embodiments, a substantially identical nucleotide or protein sequence can perform substantially the same function as the nucleotide (or encoded protein sequence) to which it is substantially identical.

In some embodiments, a polynucleotide and/or a nucleic acid construct of the disclosure can be an "expression cassette" or can be comprised within an expression cassette. As used herein, "expression cassette" means a recombinant nucleic acid molecule comprising, for example, one or more polynucleotides of the disclosure (e.g., a guide nucleic acid), wherein polynucleotide is operably associated with one or more control sequences (e.g., a promoter, terminator and the like). Thus, in some embodiments, one or more expression cassettes can be provided, which are designed to express, for example, a nucleic acid construct of the disclosure (e.g., comprising a guide nucleic acid). When an expression cassette of the present disclosure comprises more than one polynucleotide, the polynucleotides can be operably linked to a single promoter that drives expression of all of the polynucleotides or the polynucleotides can be operably linked to one or more separate promoters (e.g., three polynucleotides can be driven by one, two or three promoters in any combination). When two or more separate promoters are used, the promoters can be the same promoter, or they can be different promoters.

An expression cassette comprising a nucleic acid construct of the disclosure can be chimeric, meaning that at least one of its components is heterologous with respect to at least one of its other components (e.g., a promoter from the host organism operably linked to a polynucleotide of interest to be expressed in the host organism, wherein the polynucleotide of interest is from a different organism than the host or is not normally found in association with that promoter). An expression cassette can also be one that is naturally occurring but has been obtained in a recombinant form useful for heterologous expression.

An expression cassette can optionally include a transcriptional and/or translational termination region (i.e., termination region) and/or an enhancer region that is functional in the selected host cell. A variety of transcriptional terminators and enhancers are known in the art and are available for use in expression cassettes. Transcriptional terminators are responsible for the termination of transcription and correct mRNA polyadenylation. A termination region and/or the enhancer region can be native to the transcriptional initiation region, can be native to, for example, a gene encoding a sequence-specific nucleic acid binding protein, a gene encoding a nuclease, a gene encoding a reverse transcriptase, a gene encoding a deaminase, and the like, or can be native to a host cell, or can be native to another source.

An expression cassette of the disclosure also can include a polynucleotide encoding a selectable marker or screenable marker, which can be used to select a transformed host cell. As used herein, "selectable marker" means a polynucleotide sequence that when expressed imparts a distinct phenotype to the host cell expressing the marker and thus allows such transformed cells to be distinguished from those that do not have the marker. Such a polynucleotide sequence can encode either a selectable or screenable marker, depending on whether the marker confers a trait that can be selected for by chemical means, such as by using a selective agent (e.g., an antibiotic and the like), or on whether the marker is simply a trait that one can identify through observation or testing, such as by screening (e.g., fluorescence). Many examples of suitable selectable/screenable markers are known in the art and can be used in the expression cassettes described herein.

In addition to expression cassettes, the nucleic acid constructs and polynucleotide sequences described herein can be used in connection with vectors. By "vector" is meant a nucleic acid molecule, preferably a DNA molecule derived, for example, from a plasmid, bacteriophage or plant virus, into which a nucleic acid sequence may be inserted. A vector preferably contains one or more unique restriction sites and may be capable of autonomous replication in a defined host cell including a target cell or tissue or a progenitor cell or tissue thereof, or be integrable into the genome of the defined host such that the cloned sequence is reproducible. Accordingly, the vector may be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector may contain any means for assuring self-replication. Alternatively, the vector may be one which, when introduced into a cell, is integrated into the genome of the recipient cell and replicated together with the chromosome(s) into which it has been integrated. A vector system may comprise a single vector or plasmid, two or more vectors or plasmids, which together contain the total DNA to be introduced into the genome of the host cell, or a transposon. The choice of the vector will typically depend on the compatibility of the vector with the cell into which the vector is to be introduced. The vector may also include a selection marker such as an antibiotic resistance gene that can be used for selection of suitable transformants, or sequences that enhance transformation of prokaryotic or eukaryotic cells such as T-DNA or P-DNA sequences. Examples of such resistance genes and sequences are well known to those of skill in the art.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

A number of techniques are available for the introduction of nucleic acid molecules into a plant cell. The methods do not depend on a particular method for introducing one or more nucleotide sequences into a plant, only that they gain access to the interior of at least one cell of the plant. Where more than one nucleotide sequence is to be introduced, they can be assembled as part of a single nucleic acid construct, or as separate nucleic acid constructs, and can be located on the same or different nucleic acid constructs. Accordingly, the nucleotide sequences can be introduced into the cell of interest in a single transformation event, in separate transformation events, or, for example, in plants, as part of a breeding protocol.

Suitable methods for transformation of host plant cells include virtually any method by which DNA or RNA can be introduced into a cell (for example, where a recombinant DNA construct is stably integrated into a plant chromosome or where a recombinant DNA construct or an RNA is transiently provided to a plant cell) and are well known in the art. Two effective methods for cell transformation are *Agrobacterium*-mediated transformation and microprojectile bombardment-mediated transformation. Microprojectile bombardment methods are illustrated, for example, in U.S. Pat. Nos. 5,550,318; 5,538,880; 6,160,208; and 6,399,861. *Agrobacterium*-mediated transformation methods are described, for example in U.S. Pat. No. 5,591,616, which is incorporated herein by reference in its entirety. Transformation of plant material is practiced in tissue culture on nutrient media, for example a mixture of nutrients that allow cells to grow in vitro. Recipient cell targets include, but are not limited to, meristem cells, shoot tips, hypocotyls, calli, immature or mature embryos, and gametic cells such as microspores and pollen. Callus can be initiated from tissue sources including, but not limited to, immature or mature embryos, hypocotyls, seedling apical meristems, microspores and the like. Cells containing a transgenic nucleus are grown into transgenic plants.

In transformation, DNA is typically introduced into only a small percentage of target plant cells in any one transformation experiment. Marker genes are used to provide an efficient system for identification of those cells that are stably transformed by receiving and integrating a recombinant DNA molecule into their genomes. Preferred marker genes provide selective markers which confer resistance to a selective agent, such as an antibiotic or an herbicide. Potentially transformed cells are exposed to the selective agent. In the population of surviving cells are those cells where, generally, the resistance-conferring gene is integrated and expressed at sufficient levels to permit cell survival. Cells can be tested further to confirm stable integration of the exogenous DNA. Commonly used selective marker genes include those conferring resistance to antibiotics such as kanamycin and paromomycin (nptII), hygromycin B (aph IV), spectinomycin (aadA) and gentamycin (aac3 and aacC4) or resistance to herbicides such as glufosinate (bar or pat), dicamba (DMO) and glyphosate (aroA or EPSPS). Examples of such selectable markers are illustrated in U.S. Pat. Nos. 5,550,318; 5,633,435; 5,780,708 and 6,118,047. Markers which provide an ability to visually screen transformants can also be employed, for example, a gene expressing a colored or fluorescent protein such as a luciferase or green fluorescent protein (GFP) or a gene expressing a beta-glucuronidase or uidA gene (GUS) for which various chromogenic substrates are known.

Transformation of a cell may be stable or transient. Thus, in some embodiments, a plant cell is stably transformed with a nucleic acid molecule. In other embodiments, a plant is transiently transformed with a nucleic acid molecule. "Transient transformation" in the context of a polynucleotide means that a polynucleotide is introduced into the cell and does not integrate into the genome of the cell. By "stably introducing" or "stably introduced" in the context of a polynucleotide introduced into a cell is intended the introduced polynucleotide is stably incorporated into the genome of the cell, and thus the cell is stably transformed with the polynucleotide.

"Stable transformation" or "stably transformed" as used herein means that a nucleic acid is introduced into a cell and integrates into the genome of the cell. As such, the integrated nucleic acid is capable of being inherited by the progeny thereof, more particularly, by the progeny of multiple successive generations. "Genome" as used herein also includes the nuclear and the plastid genome, and therefore includes integration of the nucleic acid into, for example, the chloroplast genome. Stable transformation as used herein can also refer to a transgene that is maintained extrachromasomally, for example, as a minichromosome.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a plant or other organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods. Transformation can also be detected by direct sequencing and/or hybridization protocols well known in the art.

Procedures for transforming plants are well known and routine in the art and are described throughout the literature. Non-limiting examples of methods for transformation of plants include transformation via bacterial-mediated nucleic acid delivery (e.g., via Agrobacteria), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Miki et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska (Cell. Mol. Biol. Lett. 7:849-858 (2002)).

*Agrobacterium*-mediated transformation is a commonly used method for transforming plants, in particular, dicot plants, because of its high efficiency of transformation and because of its broad utility with many different species. *Agrobacterium*-mediated transformation typically involves transfer of the binary vector carrying the foreign DNA of interest to an appropriate *Agrobacterium* strain that may depend on the complement of vir genes carried by the host *Agrobacterium* strain either on a co-resident Ti plasmid or chromosomally (Uknes et al. (1993) *Plant Cell* 5:159-169). The transfer of the recombinant binary vector to *Agrobacterium* can be accomplished by a triparental mating procedure using *Escherichia coli* carrying the recombinant binary vector, a helper *E. coli* strain that carries a plasmid that is able to mobilize the recombinant binary vector to the target *Agrobacterium* strain. Alternatively, the recombinant binary vector can be transferred to *Agrobacterium* by nucleic acid transformation (Höfgen & Willmitzer (1988) *Nucleic Acids Res.* 16:9877).

Transformation of a plant by recombinant *Agrobacterium* usually involves co-cultivation of the *Agrobacterium* with explants from the plant and follows methods well known in the art. Transformed tissue is regenerated on selection medium carrying an antibiotic or herbicide resistance marker between the binary plasmid T-DNA borders.

Another method for transforming plants, plant parts and/or plant cells involves propelling inert or biologically active particles at plant tissues and cells. Sec, e.g., U.S. Pat. Nos. 4,945,050; 5,036,006 and 5,100,792. Generally, this method involves propelling inert or biologically active particles at the plant cells under conditions effective to penetrate the outer surface of the cell and afford incorporation within the interior thereof. When inert particles are utilized, the vector can be introduced into the cell by coating the particles with the vector containing the nucleic acid of interest. Alternatively, a cell or cells can be surrounded by the vector so that the vector is carried into the cell by the wake of the particle. Biologically active particles (e.g., dried yeast cells, dried bacterium or a bacteriophage, each containing one or more nucleic acids sought to be introduced) also can be propelled into plant tissue.

Thus, in certain embodiments, a plant cell can be transformed by any method known in the art and as described herein and intact plants can be regenerated from these transformed cells using any of a variety of known techniques. Plant regeneration from plant cells, plant tissue culture and/or cultured protoplasts is described, for example, in Evans et al. (*Handbook of Plant Cell Cultures*, Vol. 1, MacMilan Publishing Co. New York (1983)); and Vasil I. R. (ed.) (*Cell Culture and Somatic Cell Genetics of Plants*, Acad. Press, Orlando, Vol. I (1984), and Vol. II (1986)). Methods of selecting for transformed plants, plant cells and/or plant tissue culture are routine in the art and can be employed in the methods provided herein.

The most commonly used methods to transform wheat plants comprise two steps: the delivery of DNA into regenerable wheat cells and plant regeneration through in vitro tissue culture. Two methods are commonly used to deliver the DNA: T-DNA transfer using *Agrobacterium tumefaciens* or related bacteria and direct introduction of DNA via particle bombardment, although other methods have been used to integrate DNA sequences into wheat or other cereals. It will be apparent to the skilled person that the particular choice of a transformation system to introduce a nucleic acid construct into plant cells is not essential to or a limitation of the disclosure, provided it achieves an acceptable level of nucleic acid transfer. Such techniques for wheat are well known in the art.

Wheat plants can be produced by introducing a nucleic acid construct into a recipient cell and growing a new plant that comprises and expresses a polynucleotide according to the disclosure. The process of growing a new plant from a transformed cell which is in cell culture is referred to as "regeneration". Regenerable wheat cells include cells of mature embryos, meristematic tissue such as the mesophyll cells of the leaf base, or from the scutella of immature embryos, obtained 12-20 days post-anthesis, or callus derived from any of these. The most commonly used route to recover regenerated wheat plants is somatic embryogenesis using media such as MS-agar supplemented with an auxin such as 2,4-D and a low level of cytokinin. Any wheat type that is regenerable may be used. Transformation events in one of these more readily regenerable varieties may be transferred to any other wheat cultivars including elite varieties by standard backcrossing.

Examples of selectable markers include, but are not limited to, a nucleotide sequence encoding neo or nptII, which confers resistance to kanamycin, G418, and the like (Potrykus et al. (1985) *Mol. Gen. Genet.* 199:183-188); a nucleotide sequence encoding bar, which confers resistance to phosphinothricin; a nucleotide sequence encoding an altered 5-enolpyruvylshikimate-3-phosphate (EPSP) synthase, which confers resistance to glyphosate (Hinchee et al. (1988) Biotech. 6:915-922); a nucleotide sequence encoding a nitrilase such as bxn from *Klebsiella* ozaenae that confers resistance to bromoxynil (Stalker et al. (1988) *Science* 242:419-423); a nucleotide sequence encoding an altered acetolactate synthase (ALS) that confers resistance to imidazolinone, sulfonylurea or other ALS-inhibiting chemicals (EP Patent Application No. 154204); a nucleotide sequence encoding a methotrexate-resistant dihydrofolate reductase (DHFR) (Thillet et al. (1988) *J. Biol. Chem.* 263:12500-12508); a nucleotide sequence encoding a dalapon dehalogenase that confers resistance to dalapon; a nucleotide sequence encoding a mannose-6-phosphate isomerase (also referred to as phosphomannose isomerase (PMI)) that confers an ability to metabolize mannose (U.S. Pat. Nos. 5,767,378 and 5,994,629); a nucleotide sequence encoding an altered anthranilate synthase that confers resistance to 5-methyl tryptophan; and/or a nucleotide sequence encoding hph that confers resistance to hygromycin. One of skill in the art is capable of choosing a suitable selectable marker for use in a nucleic acid construct.

Additional selectable markers include, but are not limited to, a nucleotide sequence encoding β-glucuronidase or uidA (GUS) that encodes an enzyme for which various chromogenic substrates are known; an R-locus nucleotide sequence that encodes a product that regulates the production of anthocyanin pigments (red color) in plant tissues (Dellaporta et al., "Molecular cloning of the maize R-nj allele by transposon-tagging with Ac," pp. 263-282 In: *Chromosome Structure and Function: Impact of New Concepts,* 18th Stadler Genetics Symposium (Gustafson & Appels eds., Plenum Press 1988)); a nucleotide sequence encoding β-lactamase, an enzyme for which various chromogenic substrates are known (e.g., PADAC, a chromogenic cephalosporin) (Sutcliffe (1978) *Proc. Natl. Acad. Sci. USA* 75:3737-3741); a nucleotide sequence encoding xylE that encodes a catechol dioxygenase (Zukowsky et al. (1983) *Proc. Natl. Acad. Sci. USA* 80:1101-1105); a nucleotide sequence encoding tyrosinase, an enzyme capable of oxidizing tyrosine to DOPA and dopaquinone, which in turn condenses to form melanin (Katz et al. (1983) *J. Gen. Microbiol.* 129:2703-2714); a nucleotide sequence encoding β-galactosidase, an enzyme for which there are chromogenic substrates; a nucleotide sequence encoding luciferase (lux) that allows for bioluminescence detection (Ow et al. (1986) *Science* 234:856-859); a nucleotide sequence encoding acquorin, which may be employed in calcium-sensitive bioluminescence detection (Prasher et al. (1985) *Biochem. Biophys. Res. Comm.* 126:1259-1268); or a nucleotide sequence encoding green fluorescent protein (Niedz et al. (1995) *Plant Cell Reports* 14:403-406). One of skill in the art is capable of choosing a suitable selectable marker for use in a nucleic acid construct.

EMBODIMENTS

The following numbered embodiments also form part of the present disclosure:

1. A modified plant, or a progeny thereof, having reduced polyphenol oxidase (PPO) activity, the plant comprising a mutation in at least one endogenous PPO1 or PPO2 gene, optionally wherein the mutation is in a region of the endogenous PPO1 or PPO2 gene that encodes a copper binding domain of a PPO polypeptide.
2. The modified plant of embodiment 1, wherein the endogenous PPO1 or PPO2 gene comprises a nucleotide sequence having at least 80%, at least 90%, at least 95%, at least 98%, at least 99%, or 100% sequence identity to SEQ ID NO: 1, 2, 3, 4, 5, 6, 7, 22, 23, 28, or 29.

3. The modified plant of embodiment 1 or embodiment 2, wherein the mutation is an insertion, a deletion, or a substitution of one or more nucleotides.
4. The modified plant of any one of embodiments 1-3, wherein the mutation introduces a frameshift mutation, a pre-mature stop codon, or an in-frame deletion in the PPO1 or PPO2 gene.
5. The modified plant of any one of embodiments 1-4, wherein the PPO activity in the grain of the plant is reduced relative to the PPO activity in grain without the mutation.
6. The modified plant of embodiment 5, wherein the PPO activity is reduced by at least 70%, at least 80%, or at least 90% relative to the PPO activity in grain without the mutation.
7. The modified plant of any one of embodiments 1-6, wherein enzymatic browning of processed grain of the modified plant is reduced compared to processed grain of a control plant not comprising the mutation.
8. The modified plant of any one of embodiments 1-7, wherein the plant is in the Triticeae tribe.
9. The modified plant of any one of embodiments 1-8, wherein the plant is a wheat, barley, or rye plant.
10. The modified plant of any one of embodiments 1-9, wherein the plant is a wheat plant.
11. The modified wheat plant of embodiment 10, wherein the plant comprises a mutation in at least two, three, four, five, or six endogenous PPO1 or PPO2 genes selected from PPO2A-1, PPO2A-2, PPO2B-1, PPO2B-2, PPO2B-3, PPO2D-1, and PPO2D-2.
12. The modified wheat plant of embodiment 10 or embodiment 11, wherein the plant comprises a mutation in PPO2A-1, PPO2A-2, PPO2B-1, PPO2B-2, PPO2B-3, PPO2D-1, and PPO2D-2.
13. The modified wheat plant of any one of embodiments 10-12, wherein the wheat plant is of the variety Fielder, Guardian, or Steamboat.
14. A modified wheat plant, or a progeny thereof, having reduced PPO activity, the plant comprising a mutation in the endogenous PPO1 or PPO2 genes of PPO2A-1, PPO2A-2, PPO2B-1, PPO2B-2, PPO2B-3, PPO2D-1, and PPO2D-2.
15. The modified wheat plant of embodiment 14, wherein the mutation is in a region of the endogenous PPO1 or PPO2 genes that encodes a copper binding domain of a PPO polypeptide.
16. A plant part, plant cell, or seed of the modified plant of any one of embodiments 1-15.
17. A method of reducing PPO activity in a plant, the method comprising: introducing a mutation in at least one endogenous PPO1 or PPO2 gene, optionally wherein the mutation is in a region of the endogenous PPO1 or PPO2 gene that encodes a copper binding domain of a PPO polypeptide.
18. The method of embodiment 17, wherein the endogenous PPO1 or PPO2 gene comprises a nucleotide sequence having at least 80%, at least 90%, at least 95%, at least 98%, at least 99%, or 100% sequence identity to SEQ ID NO: 1, 2, 3, 4, 5, 6, 7, 22, 23, 28, or 29.
19. The method of embodiment 17 or embodiment 18, wherein the PPO activity in the grain of the plant is reduced relative to the PPO activity in grain without the mutation.
20. The method of any one of embodiments 17-19, wherein the mutation is introduced by genome editing.
21. The method of any one of embodiments 17-20, wherein the method comprises introducing a Cas nuclease and a guide RNA targeting the PPO1 or PPO2 gene.
22. The method of any one of embodiments 17-21, wherein the guide RNA comprises the nucleotide sequence of SEQ ID NO: 34.
23. The method of any one of embodiments 17-22, wherein the plant is in the Triticeae tribe.
24. The method of any one of embodiments 17-23, wherein the plant is a wheat, barley, or rye plant.
25. The method of any one of embodiments 17-24, wherein the plant is a wheat plant.
26. The method of embodiment 25, wherein the mutation is introduced in at least two, three, four, five, or six endogenous PPO1 or PPO2 genes selected from PPO2A-1, PPO2A-2, PPO2B-1, PPO2B-2, PPO2B-3, PPO2D-1, and PPO2D-2.
27. The method of embodiment 25 or embodiment 26, wherein the mutation is introduced in PPO2A-1, PPO2A-2, PPO2B-1, PPO2B-2, PPO2B-3, PPO2D-1, and PPO2D-2.
28. The method of any one of embodiments 25-27, wherein the wheat plant is of the variety Fielder, Steamboat, or Guardian.
29. A method of producing a plant having reduced PPO activity, the method comprising: (a) crossing the plant of any one of embodiments 1-15 with itself or another plant to produce seed; (b) growing one or more progeny plants from the seed; and (c) selecting a progeny plant comprising the mutation to produce a plant having reduced PPO activity.
30. The method of embodiment 29 further comprising: (c) crossing the progeny plant with itself or another plant; and (d) repeating steps (b) and (c) for an additional 0-7 generations to produce a plant having grain with reduced PPO activity.
31. A crop comprising a plurality of the plants of any one of embodiments 1-15 planted together in an agricultural field.
32. A commodity plant product prepared from the plant of any one of embodiments 1-15, or a part thereof.
33. The commodity plant product of embodiment 32, wherein the product is grain, flour, a baked good, cereal, pasta, a beverage, livestock feed, biofuel, straw, a construction material, or starch.
34. The commodity plant product of embodiment 32 or embodiment 33, wherein the product has reduced browning.
35. A method for producing a commodity plant product, the method comprising processing the plant of any one of embodiments 1-15, or a part thereof, to obtain the product.
36. The method of embodiment 35, wherein the commodity plant product is grain, flour, a baked good, cereal, pasta, a beverage, livestock feed, biofuel, straw, a construction material, or starch.
37. A guide RNA for editing a PPO1 or PPO2 gene comprising the nucleotide sequence of SEQ ID NO: 34.
38. An expression cassette or vector encoding the guide RNA of embodiment 37.
39. A plant cell comprising a Cas9 nuclease and the guide RNA of embodiment 37 or the expression cassette or vector of embodiment 38.
40. The plant cell of embodiment 39, wherein the plant cell is wheat plant cell, a rye plant cell, or a barley plant cell.

All publications and patent applications mentioned in the specification are indicative of the level of skill of those skilled in the art to which this disclosure pertains. All publications and patent applications are herein incorporated by reference to the same extent as if each individual publication or patent application was specifically and individually indicated to be incorporated by reference.

Although the foregoing disclosure has been described in some detail by way of illustration and example for purposes of clarity of understanding, it will be obvious that certain changes and modifications may be practiced within the scope of the appended embodiments.

The following examples are offered by way of illustration and not by way of limitation.

EXAMPLES

Example 1: PPO1 and PPO2 Genes are Highly Expressed in the Developing Wheat Grain An analysis of a whole-plant hexaploid wheat RNA-seq dataset from the landrace 'Chinese Spring' showed that among the 20 PPO genes, the seven paralogous PPO1 and PPO2 genes are predominantly expressed in developing grain tissues and account for a high proportion of all PPO transcripts in these tissues. Some PPO1 and PPO2 genes were also expressed in other plant tissues; PPO-2D-1 was highly expressed in stem and spike tissues during anthesis while PPO-2B-1 transcripts were detected in leaf tissues post-anthesis (FIG. 1). By contrast, transcript levels of other members of the PPO family were low in the developing grain and were more highly expressed in vegetative tissues (FIG. 1).

Figure 2:
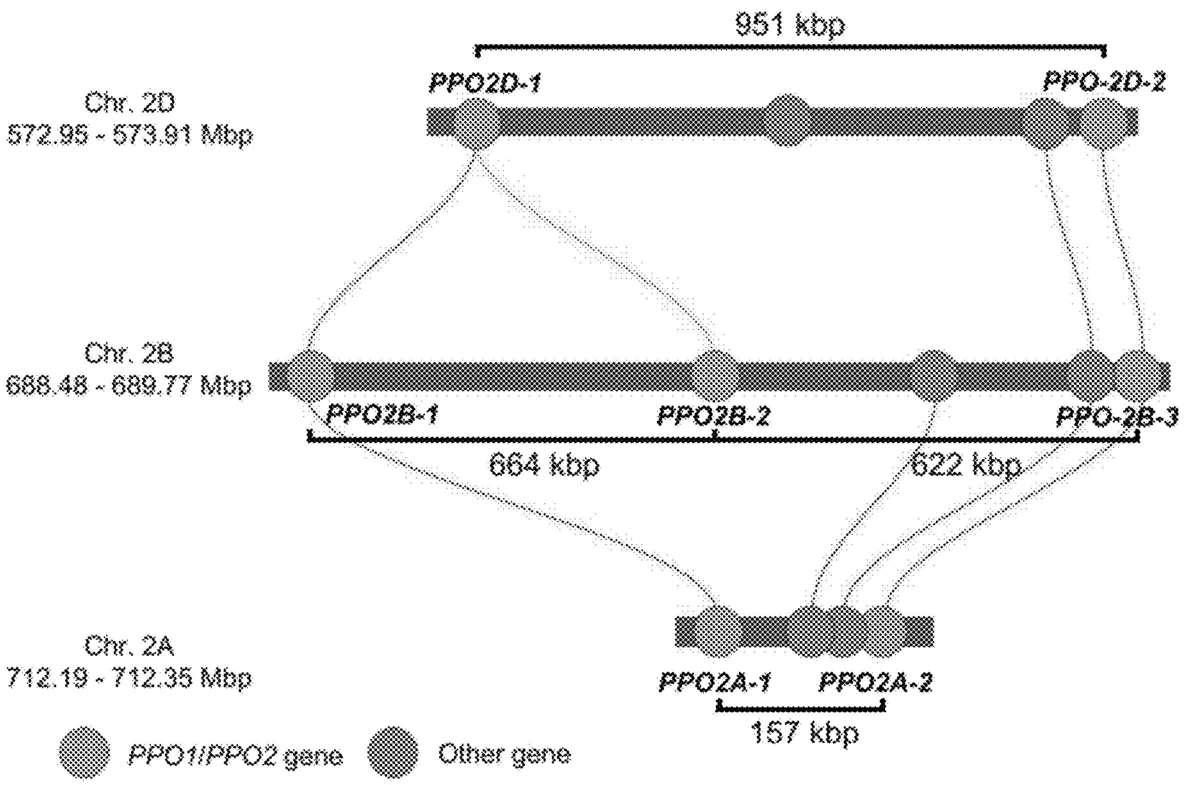
FIG. 2 shows the position of PPO1 and PPO2 genes on homocologous group 2 chromosomes of the wheat landrace 'Chinese Spring' IWGSC RefSeq v1.1 genome assembly. Gene positions are drawn to scale and homologous genes linked by lines determined using the Triticeae Gene Tribe microhomology tool. Physical distances between the start of each gene are labeled.

The genome of 'Chinese Spring' has two PPO1/PPO2 genes on chromosome 2A, three on chromosome 2B and two on chromosome 2D. On each chromosome, these genes are separated by short physical distances (FIG. 2). Based on their expression profile and known association with PPO activity in the grain, all seven PPO1 and PPO2 genes were targeted for knockout by genome editing in the spring wheat variety 'Fielder'. The 'Fielder' genome contains 25 PPO genes that encode proteins with tyrosinase, DWL and KWDV domains characteristic of these proteins, including all 20 PPO genes described in 'Chinese Spring' and seven PPO1 and PPO2 genes (Table 2).

Three PPO1/PPO2 genes in 'Fielder' are predicted to encode non-functional proteins: a PPO2A-1 allele with a 54-nucleotide deletion in the third exon predicted to encode a stop codon at amino acid 423, a PPO2B-2 allele with a 1 nucleotide deletion in the third exon (1977delC) predicted to encode a stop codon at amino acid 525, and a PPO2D-2 allele with a 1 nucleotide substitution in the first exon (20C>A) predicted to encode a stop codon at amino acid 7.

Table 2 summarizes the PPO genes in 'Chinese Spring' and 'Fielder'. The nucleotide sequences of PPO genes present in both 'Chinese Spring' and 'Fielder' are identical in both genotypes across the sgRNA sequence. The number and position of mismatches between the sgRNA sequence used in this study and each PPO gene is presented. The PAM (CCC) is indicated in italics and mismatches between the sgRNA and gene are in bold. Genes that are absent from the 'Chinese Spring' genome assembly are marked with a dash (-). The encoded proteins of each of these genes contain conserved Tyrosinase, KWL and KFDV domains.

TABLE 2

| | Gene ID | | | Number of |
|---|---|---|---|---|
| Gene name | Chinese Spring | Fielder | sgRNA sequence | mismatches |
| TaPPO2A-1 | TraesCS2A02G468200 | TraesFLD2A01G514000 | *CCC*CATCTTCTTCGCGCACCACG (SEQ ID NO: 36) | 0 |
| TaPPO2A-2 | TraesCS2A02G468500 | TraesFLD2A01G514300 | *CCC*CATCTTCTTCGCGCACCACG (SEQ ID NO: 36) | 0 |
| TaPPO2B-1 | TraesCS2B02G491000 | TraesFLD2B01G529900 | *CCC*CATCTTCTTCGCGCACCACG (SEQ ID NO: 36) | 0 |
| TaPPO2B-2 | TraesCS2B02G491100 | TraesFLD2B01G530000 | *CCC*CATCTTCTTCGCGCACCACG (SEQ ID NO: 36) | 0 |
| TaPPO2B-3 | TraesCS2B02G491400 | TraesFLD2B01G530300 | *CCC*CATCTTCTTCGCGCACCACG (SEQ ID NO: 36) | 0 |
| TaPPO2D-1 | TraesCS2D02G468200 | TraesFLD2D01G517900 | *CCC*CATCTTCTTCGCGCACCACG (SEQ ID NO: 36) | 0 |
| TaPPO2D-2 | TraesCS2D02G468600 | TraesFLD2D01G518200 | *CCC*CATCTTCTTCGCGCACCACG (SEQ ID NO: 36) | 0 |
| TaPPO3A-1 | TraesCS3A02G326600 | TraesFLD3A01G347700 | *CCC***GC**TCTTCT**A**C**C**CGCACCAC**A** (SEQ ID NO: 37) | 5 |
| TaPPO3A-2 | — | TraesFLD3A01G347800 | *CCC***GC**TCTTCT**A**C**C**CGCACCAC**A** (SEQ ID NO: 37) | 5 |
| TaPPO3B-1 | TraesCS3B02G355900 | TraesFLD3B01G404300 | *CCC***GC**TCTTCT**A**C**C**CGCA**G**CAC**A** (SEQ ID NO: 38) | 6 |
| TaPPO3B-2 | TraesCS3B02G568600 | TraesFLD3B01G637100 | *CCC***AC**TCTTCT**A**C**C**C**A**CACCAC**A** (SEQ ID NO: 39) | 6 |
| TaPPO4B-1 | TraesCS4B02G385600 | TraesFLD4B01G423700 | *CCC***AC**TCTTCT**A**C**C**C**A**CAC**A**AC**A** (SEQ ID NO: 40) | 7 |

TABLE 2-continued

| | Gene ID | | | Number of |
|---|---|---|---|---|
| Gene name | Chinese Spring | Fielder | sgRNA sequence | mismatches |
| TaPPO4D-1 | TraesCS4D02G358500 | TraesFLD4D01G404500 | *CCC***GC**TCTTCT**A**C**CT**GCACCAC**A** (SEQ ID NO: 41) | 6 |
| TaPPO4D-2 | TraesCS4D02G359200 | TraesFLD4D01G405400 | *CCC***AC**TCTTCT**A**C**CC**ACACCAC**A** (SEQ ID NO: 39) | 6 |
| TaPPO5A-1 | TraesCS5A02G549200 | TraesFLD5A01G586800 | *CCC***AC**TCTTCT**A**C**CC**ACACCAC**A** (SEQ ID NO: 39) | 6 |
| TaPPO6A-1 | TraesCS6A02G041900 | TraesFLD6A01G054300 | *CCCC***G**TCTTCT**A**C**T**CGCACCACG (SEQ ID NO: 42) | 3 |
| TaPPO6B-1 | TraesCS6B02G016400 | TraesFLD6B01G018100 | *CCC***GG**TCTTCTTCGCGCACCACG (SEQ ID NO: 43) | 2 |
| TaPPO6B-3 | — | TraesFLD6B01G017900 | *CCC***GG**TCTTCTTCGCGCACCACG (SEQ ID NO: 43) | 2 |
| TaPPO6B-4 | — | TraesFLD6B01G018000 | *CCC***GG**TCTTCTTCGCGCACCACG (SEQ ID NO: 43) | 2 |
| TaPPO6B-5 | — | TraesFLD6B01G018200 | *CCC***GG**TCTTCTTCGCGCACCACG (SEQ ID NO: 43) | 2 |
| TaPPO6B-6 | — | TraesFLD6B01G017300 | *CCC***GG**TCTTCTT**T**GC**A**CACCACG (SEQ ID NO: 44) | 4 |
| TaPPO6B-2 | TraesCS6B02G056900 | TraesFLD6B01G067500 | *CCCC***G**TCTTCT**A**C**T**CGCACCACG (SEQ ID NO: 42) | 3 |
| TaPPO6D-1 | TraesCS6D02G048400 | TraesFLD6D01G053200 | *CCCC***G**TCTTCT**A**C**T**CGCACCACG (SEQ ID NO: 42) | 3 |
| TaPPO7A-1 | TraesCS7A02G054500 | TraesFLD7A01G056900 | *CCCC***G**TCTTCT**A**C**T**C**CA**ACCAC**T** (SEQ ID NO: 45) | 6 |
| TaPPO7D-1 | TraesCS7D02G049700 | TraesFLD7D01G064600 | *CCCC***G**TCTTCT**A**C**T**C**CA**ACCAC**T** (SEQ ID NO: 45) | 6 |

Figure 3:
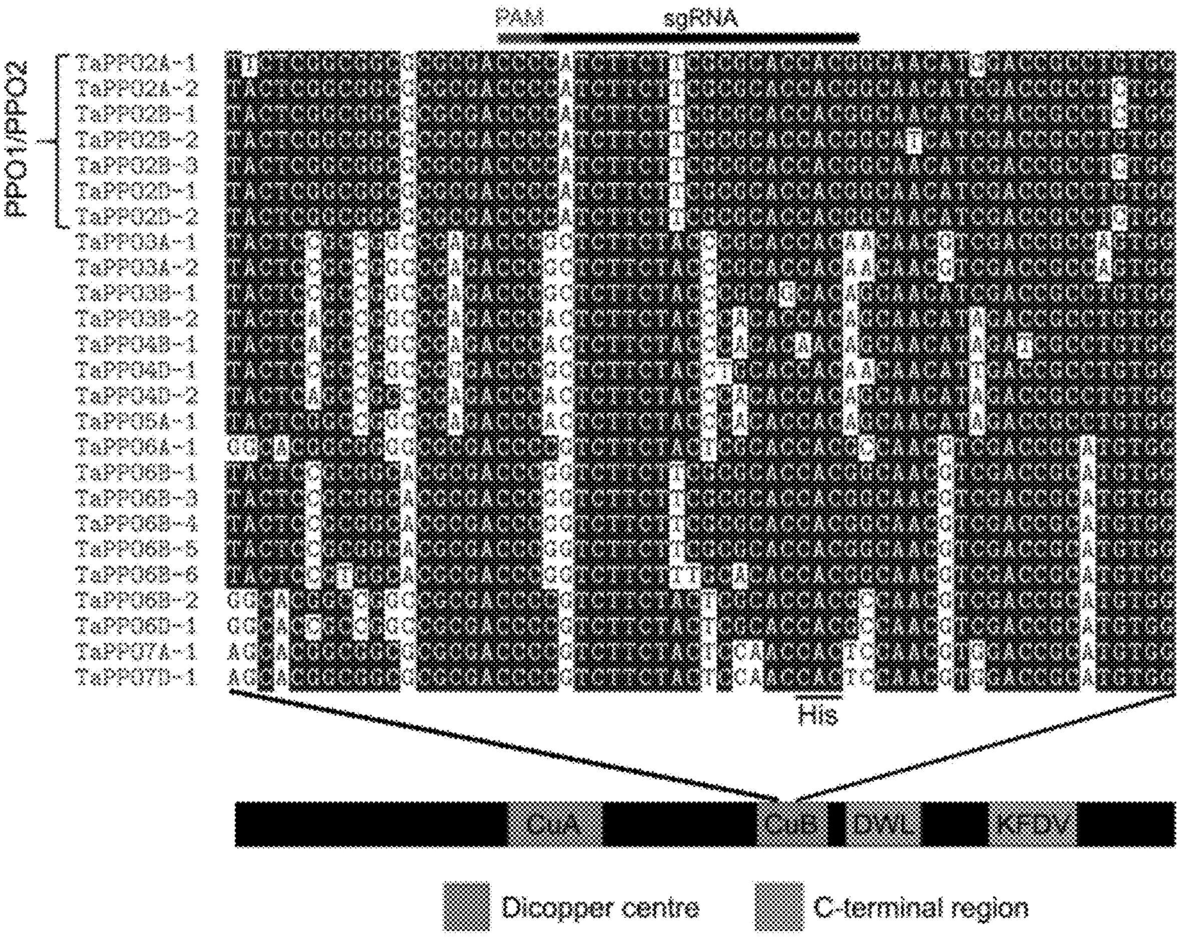
FIG. 3 shows a guide RNA designed to target seven PPO1 and PPO2 genes. The 20-nucleotide target sequence and three nucleotide protospacer adjacent motif (PAM) are indicated. The targeted region encodes the conserved copper binding site II (CuB) domain required for PPO protein function. The third conserved Histidine codon in this domain (CAC or CAT) is highlighted within the CuB binding domain. Sequence alignments are displayed in 5'-3' orientation to show the position of the guide RNA, which is designed to the antisense strand (SEQ ID NOs: 58-74). The displayed region is from nucleotides 1,442 to 1,501 based on the distance from the ATG start of the genomic DNA of PPO2A-1 in 'Fielder'. The sgRNA position is 1,462-1,481 on the reverse strand and is preceded by a 'GGG' PAM site.

Alignment of all 25 PPO genes revealed a 38-nucleotide region within the CuB binding domain that shared 100% identity between all seven PPO1 and PPO2 target genes (FIG. 3). A sgRNA was designed between nucleotides 1,462 and 1,481 on the antisense strand, including a "GGG" Protospacer Adjacent Motif (PAM). Although this PAM was also present in the 18 non-target PPO genes, each contained at least two polymorphisms within the sgRNA target sequence, including in the critical 'seed' region at the 3' end of the sgRNA that is important in determining target activity (Table 2). No off-target effects are predicted in the protein-coding region of any other gene in the wheat genome, and while the 5' UTR region of eleven genes have potential off-target effects, each had at least three mismatches with the sgRNA sequence. Taken together, this analysis suggests the designed sgRNA should target all seven PPO1 and PPO2 genes, with minimal off-target activity.

The CRISPR design tools CRISPR-P and wheatCRISPR were used to support sgRNA design, incorporating quality "Rule Set 2" (RS2) scores and incidence of off-targets. The sgRNA was selected based on its high RS2 score, 100% identity to all seven target PPO1 and PPO2 genes and low predicted off-target activity in other genes in the wheat genome. A single G nucleotide was added to the start of the 20 nucleotide sgRNA sequence, and the 21-nucleotide sequence was synthesized as overlapping, complementary oligos with overhanging 5' and 3' ends complementary to the insertion site of the target vector. Oligos were hybridized and cloned into the JD633 vector by Golden Gate cloning following vector AarI digestion. This sgRNA was integrated immediately downstream of the U6 promoter and the vector also contains ZmUbil::SpCas9 and TaGRF4:TaGIF1 coding sequences which confer improved regeneration rates in transformed callus tissue. Ligated vectors were confirmed by Sanger sequencing and transformed into DH5-α *E. coli* cells from which purified plasmid DNA was extracted. After confirming sequence insertion and integrity by Sanger sequencing, plasmid DNA was transformed into *Agrobacterium tumefaciens* strain AGL1 by electroporation and transformed into each wheat genotype (Guardian, Steamboat and Fielder) using embryo transformation. Transgenic wheat plants were selected on media containing 15 mg/L of hygromycin media and following regeneration, were validated by PCR assays to amplify two fragments of the transformed plasmid.

Figure 4A:
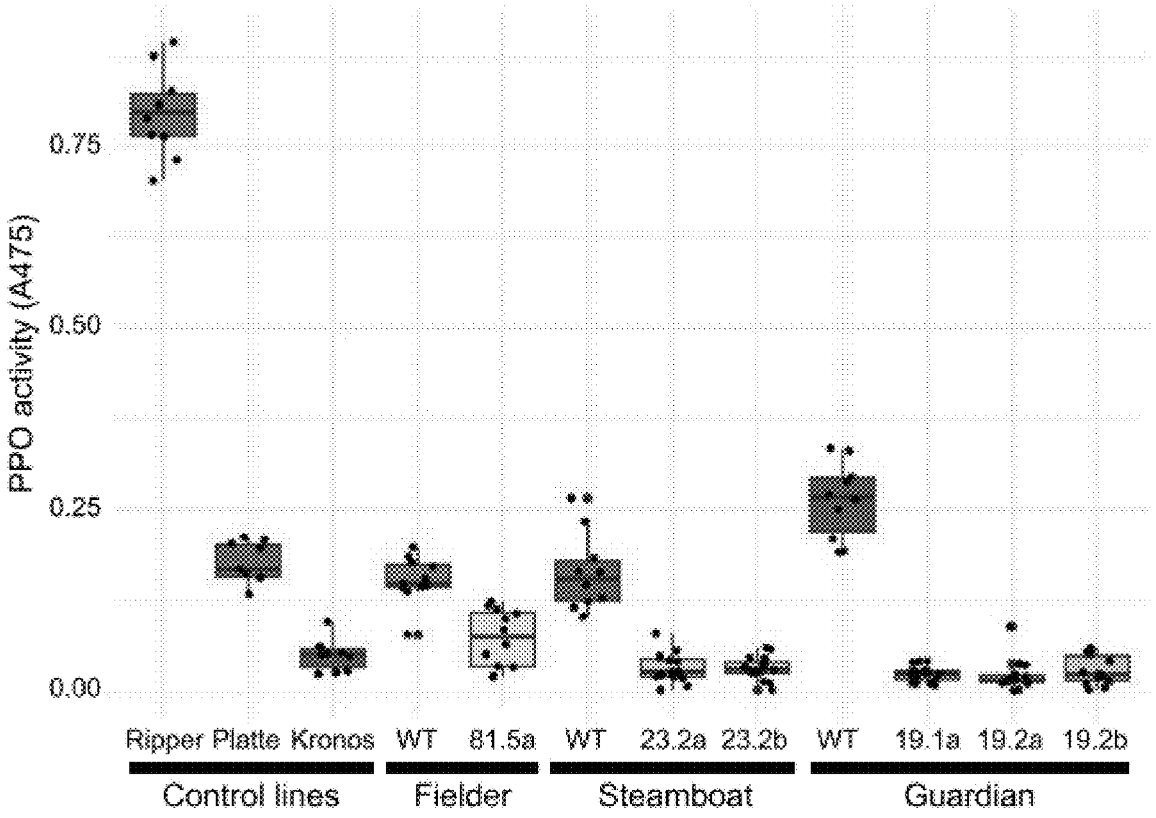
FIG. 4A-B shows PPO activity in wild-type and edited wheat lines from 'Fielder', 'Steamboat' and 'Guardian'.

Example 2: Multiplexed Genome Editing Reduces Polyphenol Oxidase Activity in Wheat Grain All seven $T_0$ lines carrying the CRISPR/Cas9 construct exhibited induced variation 3-4 nucleotides upstream of the PAM in at least one PPO gene. Many polymorphisms were biallelic or heterozygous, so $T_0$ line 81.5a with edits in all seven PPO1 and PPO2 genes was selfed to generate $T_1$ plants. Mean PPO activity in the $T_1$ generation was 52.6% lower than wild-type 'Fielder' plants ($P<0.0001$, $n=12$) and comparable to activity in the durum wheat 'Kronos', which is commonly included as an extremely low-PPO control line which carries just two functional PPO1 and PPO2 genes (FIG. 4A).

PPO activity in individual $T_1$ lines ranged from 0.033 to 0.124, suggesting they carry different allelic combinations at each target gene. Many induced mutations included one- and two-nucleotide indels that confer frameshift mutations likely to disrupt protein function (Table 3). Other deletions were in-frame, such as the 15 bp deletion in PPO2D-1 but encompassed critical residues in the CuB domain of the encoded PPO protein that are also likely to significantly disrupt function (Table 3).

PPO content was assessed using the L-DOPA method (AACC International Method 22-85.01) using mature harvested wheat grains from greenhouse-grown plants. For each genotype, 5 kernels were placed into a 2 ml microcentrifuge tube before adding 1.5 ml of a solution of 5 mM L-DOPA solution in 50 mM MOPS (pH 6.5). The tubes were sealed, then rotated at 10 rpm for two hours to allow oxygen into the reaction. Absorbance of the resulting solution was measured using 1 mL of sample in a spectrophotometer set to measure at 475 nm using L-DOPA solution as a zero sample.

Table 3 summarizes the editing events in seven PPO1 and PPO2 genes in $T_1$ 'Fielder' individuals. Where mutations are heterozygous, both allele types are described.

TABLE 3

| | 81.5a.1 | 81.5a.3 | 81.5a.6 | 81.5a.8 |
|---|---|---|---|---|
| PPO activity | 0.034 | 0.124 | 0.033 | 0.118 |
| TaPPO2A-1* | 2bp del/ 1 bp del | 2 bp del/ 1 bp del | 2 bp del | 1 bp del |
| TaPPO2A-2 | 1 bp ins/ 2 bp del | 1 bp ins/ 2 bp del | 1 bp ins | 2 bp del |
| TaPPO2B-1 | 6 bp del | 6 bp del | 6 bp del | 6 bp del |
| TaPPO2B-2* | 1 bp ins | 1 bp ins | 1 bp ins | 1 bp ins |
| TaPPO2B-3 | 15 bp del | 15 bp del | 15 bp del | 15 bp del |
| TaPPO2D-1 | 2 bp del | A to C sub | A to C sub/ 1 bp del | 2 bp del/ A to C sub |
| TaPPO2D-2* | WT | 12 bp del | 12 bp del | 1 bp ins/ 12 bp del |

WT = wild-type allele.
*= natural allele is expected to encode a non-functional protein.

Figure 4B:
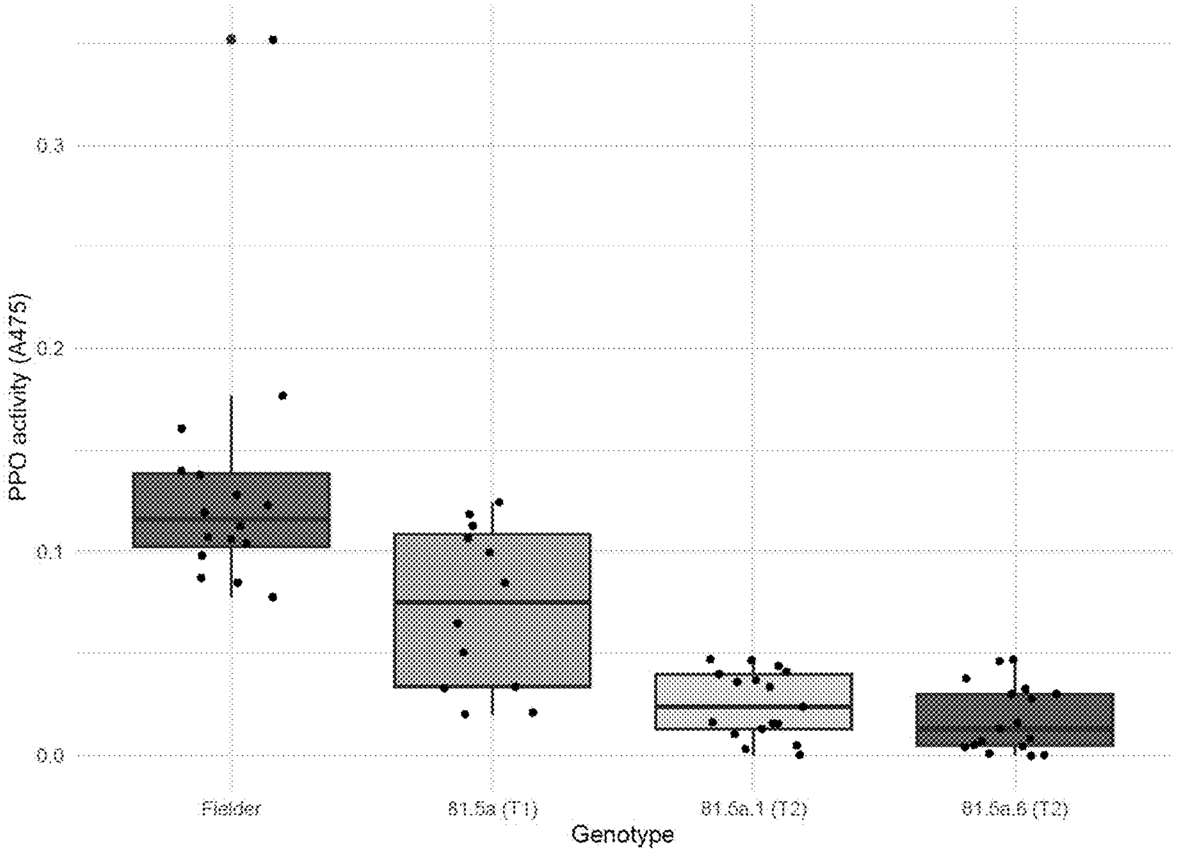

Two $T_1$ lines with the lowest PPO levels (81.5a.1 and 81.5a.6) were selfed to generate $T_2$ populations that exhibited much lower variation in PPO activity and significant reductions (FIG. 4B).

The selected sgRNA-PAM sequences are 100% identical in all PPO1 and PPO2 genes in fifteen wheat varieties with assembled genomes, indicating that this construct can be used to edit PPO1 and PPO2 genes in different wheat germplasm. To test this, the editing construct was transformed into two elite winter wheat cultivars 'Guardian' and 'Steamboat'. No genome assembly is available for these cultivars, so PCR amplification was used to confirm the presence of each PPO1 and PPO2 gene. Homocologue-specific PCR assays for PPOB2-1 and PPOB2-2 consistently failed to generate an amplicon in either 'Guardian' and 'Steamboat', suggesting the absence of these genes in these varieties. PPOB2-1 and PPOB2-2 were also absent from 'Cadenza', 'Landmark', 'Mace', 'Paragon', 'Stanley', and 'SY Mattis' likely because the duplication event that originated these genes in 'Fielder' did not occur in these varieties.

Two independent $T_0$ 'Steamboat' lines and one $T_0$ 'Guardian' line exhibited edits in all five target PPO1 and PPO2 genes. Derived $T_1$ lines from each of these plants all exhibited highly significant reductions in PPO activity ($P<0.0001$) ranging from 80.2% reduction in 'Steamboat' line 23.2b to 91.8% reduction in 'Guardian' line 19.2a (FIG. 4A). All mean values were lower than the 'Kronos' control line (FIG. 4A). These results demonstrate a high rate of editing directly in elite winter wheat genotypes.

One advantage of CRISPR/Cas9 is the ability to simultaneously induce novel genetic variation at multiple loci, including those in the same linkage block. This is especially powerful when targeting multi-gene families such as PPO that are subject to a high rate of gene expansion. A growing set of wheat genome assemblies facilitates the characterization of this variation and ensures the appropriate design of CRISPR/Cas9 constructs. In this example, the 'Fielder' genome was used to design a sgRNA targeting a region of the highly conserved CuB binding domain 100% identical between all seven target genes. In addition to facilitating multiplexed editing, targeting a conserved domain increases the likelihood that in-frame deletions or insertions disrupt gene function and generate null alleles. For example, the 15 bp deletion in PPO-2B-3 in 'Fielder' eliminates the conserved His and Phe amino acid residues that are highly conserved and likely essential to form the active site.

This contrasts with an earlier CRISPR/Cas9 study to edit PPO genes that used a sgRNA targeting a genomic region between the conserved CuA and CuB binding domains (Zhang et al., 2021). There are polymorphisms between the sgRNA sequence and four of the seven PPO genes from 'Fielder', including four mismatches with PPO2A-2, PPO2B-2, and PPO2D-2. These genes are expressed during grain development and likely contribute to PPO activity in this tissue suggesting that null alleles in all PPO1 and PPO2 genes might be required to maximize potential reduction in PPO activity by editing.

It is important to note that while a high rate of editing was achieved using the sgRNA described in detail here, two other sgRNAs targeting a conserved region approximately 150 nucleotides upstream exhibited zero editing efficiency in 15 transgenic $T_0$ plants screened for edits. It is possible that these CRISPR/Cas9 constructs may have induced transgenerational editing in the $T_1$ generation, but this was not evaluated due to the high rate of editing observed with the selected sgRNA. These results strongly suggest major differences in editing efficiencies for sgRNAs targeting DNA sequences less than 150 nucleotides apart and that the sequence composition of the sgRNA is critically important for editing. In addition to evaluating potential off-target effects, CRISPR design tools such as CRISPR-P and wheatCRISPR predict editing efficiency, including a RS2 score based on empirical editing data from hundreds of constructs from animal studies. However, editing efficiency was poorly correlated with RS2 score in the current study, with the editing construct with the highest RS2 score 0.64 editing with zero efficiency. One potential reason for this discrepancy is that editing efficiency models are based on animal systems that might differ in plant species, or that other factors influencing editing efficiency are not captured by these models.

Example 3: Applications in Breeding

The sgRNA used is 100% conserved in all PPO1 and PPO2 genes from 17 wheat genome assemblies screened and drove significant reductions in PPO activity in all three varieties tested. The number of target loci makes genotyping complex. In the $T_1$ generation, lines with a greater number of gene knockouts exhibited the lowest PPO activity, so for traits where an inexpensive phenotyping method is available, it may be more cost-effective to phenotypically screen early generations of edited lines to identify those with the greatest number of null alleles, especially in early generations before these mutations are fixed.

Directly editing these alleles into elite wheat cultivars using genotype-independent transformation technologies has the potential to rapidly induce beneficial changes in wheat breeding programs. Editing these genes to generate low-PPO lines would accelerate variety development, saving breeders time on marker assisted selection, expand access to high-PPO germplasm, and maximize profits for growers by ensuring high flour yield and quality. Crosses have been initiated between edited and wild-type plants to generate individuals segregating for the transgene insertion to select edited, non-transgenic lines to assess genotype performance in replicated field trials.

With the high level of conservation in the CuB binding site, the sgRNA used to edit wheat PPO genes is also 100% conserved in orthologous PPO1 and PPO2 genes from barley (*Hordeum vulgare*) and rye (*Secale cereale*) so may be a suitable approach to reduce PPO levels in these species by adapting the transformation construct. However, the orthologous PPO1 and PPO2 genes from rice, maize, and sorghum all contained multiple polymorphisms in the sgRNA sequence (Table 4), meaning the construct would need to be redesigned to match the genes in these species. The high conservation and functionality of the CuB binding domains make this an excellent target for multiplexed gene editing and would be a powerful approach in other species, including those for which transgenic technologies such as RNAi and amiRNA have previously been applied to reduce PPO transcript levels, including mushrooms, potato, and apple. Although still subject to regulatory oversight and untested in consumer markets, CRISPR/Cas9 would be an efficient approach to generate null-PPO lines for different plant species and would be subject to less oversight than genetically modified crops following the segregation of the construct inducing edits in the host genome.

Table 4 shows mismatches between the sgRNA and orthologous PPO1 and PPO2 genes from closely related species. Mismatches are highlighted in bold. PAM sequence is in italics.

TABLE 4

| Species | Gene name | Gene ID | sgRNA sequence | Number of mismatches |
|---|---|---|---|---|
| *Hordeum vulgare* | HvPPO-1 | HORVU.MOREX.r3.2HG0194690 | *CCC*CATCTTCTTCGCGCACCACG (SEQ ID NO: 46) | 0 |
| *Hordeum vulgare* | HvPPO-2 | HORVU.MOREX.r3.2HG0194630 | *CCC*CATCTTCTTCGCGCACCACG (SEQ ID NO: 46) | 0 |
| *Secale cereale* | ScPPO-1 | SECCE2Rv1G0121020 | *CC**T***CATCTTCTTCGCGCACCACG (SEQ ID NO: 47) | 1* |
| *Secale cereale* | ScPPO-2 | SECCE2Rv1G0121070 | *CCC*CATCTTCTTCGCGCACCACG (SEQ ID NO: 48) | 0 |
| *Zea mays* | ZmPPO-1 | Zm00001eb431220 | *CCC***GGTG**TTCTTCGCGCACCACG (SEQ ID NO: 49) | 3 |
| Zea mays | ZmPPO-2 | Zm00001eb428900 | *CCC***GC**TCTTCTTCGCGCACCACG (SEQ ID NO: 50) | 2 |
| *Zea mays* | ZmPPO-3 | Zm00001eb171410 | *CCC***GC**TCTTCT**A**C**T**CGCACCACG (SEQ ID NO: 51) | 4 |
| *Zea mays* | ZmPPO-4 | Zm00001eb388240 | *CCC*CATCTTCTTC**C**CGCACCAC**A** (SEQ ID NO: 52) | 2 |
| *Oryza sativa* | OsPPO-1 | Os04g0624500 | *CCC***GGTG**TTCTTCGCGCACCACG (SEQ ID NO: 53) | 3 |
| *Oryza sativa* | OsPPO-2 | Os04g0624450 | *CCC***GGTG**TTCTTCGCGCACCACG (SEQ ID NO: 53) | 3 |
| *Sorgum bicolor* | SbPPO-1 | SORBI_3007G068500 | *CCC***GC**TCTTCT**A**C**T**CGCACCACG (SEQ ID NO: 54) | 4 |
| *Sorgum bicolor* | SbPPO-2 | SORBI_3006G181300 | ***T**CC***AC**TCTTCTTCGCGCACCACG (SEQ ID NO: 55) | 3 |
| *Sorgum bicolor* | SbPPO-3 | SORBI_3006G181400 | ***T**CC***GC**TCTTCTTCGCGCACCACG (SEQ ID NO: 56) | 3 |
| *Sorgum bicolor* | SbPPO-4 | SORBI_3010G192700 | *CCC*CATCTTCT**A**C**C**CGCACCACG (SEQ ID NO: 57) | 2 |

*The mismatch in ScPPO-1 alters the PAM sequence from CCC to CCT, which is still permissible for editing

What is claimed is:

1. A modified wheat plant, or a progeny thereof, having reduced polyphenol oxidase (PPO) activity, the wheat plant comprising loss-of-function mutations in each of the endogenous PPO1 and PPO2 genes of the wheat plant, wherein each of the endogenous PPO1 and PPO2 genes comprises SEQ ID NO: 36, and wherein the loss-of-function mutations are an insertion, a deletion, or a substitution of one or more nucleotides relative to SEQ ID NO: 36.

2. The modified wheat plant of claim 1, wherein the loss-of-function mutations introduce a frameshift mutation, a pre-mature stop codon, or an in-frame deletion.

3. The modified wheat plant of claim 1, wherein the PPO activity in the grain of the wheat plant is reduced relative to the PPO activity in grain of a wheat plant without the loss-of-function mutations.

4. The modified wheat plant of claim 3, wherein the PPO activity is reduced by at least 70%, at least 80%, or at least 90% relative to the PPO activity in grain of a wheat plant without the loss-of-function mutations.

5. The modified wheat plant of claim 1, wherein browning of processed grain of the modified plant is reduced compared to processed grain of a control plant not comprising the loss-of-function mutations.

6. The modified wheat plant of claim 1, wherein the loss-of-function mutations are in endogenous PPO1 and PPO2 genes having at least 95% sequence identity to SEQ ID NO: 1, SEQ ID NO: 2, SEQ ID NO: 5, SEQ ID NO: 6, and SEQ ID NO: 7.

7. The modified wheat plant of claim 1, wherein the loss-of-function mutations are in endogenous PPO1 and PPO2 genes having at least 95% sequence identity to SEQ ID NO: 1, SEQ ID NO: 2, SEQ ID NO: 3, SEQ ID NO: 4, SEQ ID NO: 5, SEQ ID NO: 6, and SEQ ID NO: 7.

8. The modified wheat plant of claim 1, wherein the wheat plant is of the variety Fielder, Guardian, or Steamboat.

9. A wheat plant part, plant cell, or seed of the modified plant of claim 1.

10. A method of reducing PPO activity in a wheat plant, the method comprising:

introducing loss-of-function mutations in each of the endogenous PPO1 and PPO2 genes of the wheat plant, wherein each of the endogenous PPO1 and PPO2 genes comprises SEQ ID NO: 36, and wherein the loss of-function mutations are an insertion, a deletion, or a substitution of one or more nucleotides relative to SEQ ID NO: 36.

11. The method of claim 10, wherein the PPO activity in the grain of the wheat plant is reduced relative to the PPO activity in grain of a wheat plant without the loss-of-function mutations.

12. The method of claim 10, wherein the loss-of-function mutations are introduced by genome editing.

13. The method of claim 10, wherein the method comprises introducing a Cas nuclease and a guide RNA targeting each of the endogenous PPO1 and PPO2 genes.

14. The method of claim 13, wherein the guide RNA comprises the nucleotide sequence of SEQ ID NO: 34.

15. The method of claim 10, wherein the loss-of-function mutations are introduced in endogenous PPO1 and PPO2 genes having at least 95% sequence identity to SEQ ID NO: 1, SEQ ID NO: 2, SEQ ID NO: 5, SEQ ID NO: 6, and SEQ ID NO: 7.

16. The method of claim 10, wherein the loss-of-function mutations are introduced in endogenous PPO1 and PPO2 genes having at least 95% sequence identity to SEQ ID NO: 1, SEQ ID NO: 2, SEQ ID NO: 3, SEQ ID NO: 4, SEQ ID NO: 5, SEQ ID NO: 6, and SEQ ID NO: 7.

17. The method of claim 10, wherein the wheat plant is of the variety Fielder, Steamboat, or Guardian.

18. A method of producing a wheat plant having reduced PPO activity, the method comprising:

(a) crossing the wheat plant of claim 1 with itself or another wheat plant to produce seed;

(b) growing one or more progeny wheat plants from the seed; and (c) selecting a progeny wheat plant comprising the loss-of function mutations to produce a wheat plant having reduced PPO activity.

19. A crop comprising a plurality of the wheat plants of claim 1 planted together in an agricultural field.

20. A commodity plant product prepared from the wheat plant of claim 1, or a part thereof, wherein the product has reduced browning.

21. The commodity plant product of claim 20, wherein the product is grain, flour, a baked good, cereal, pasta, a beverage, livestock feed, biofuel, straw, a construction material, or starch.

22. A method for producing a commodity plant product, the method comprising processing the wheat plant of claim 1, or a part thereof, to obtain the product.

23. The method of claim 22, wherein the commodity plant product is grain, flour, a baked good, cereal, pasta, a beverage, livestock feed, biofuel, straw, a construction material, or starch.

24. A guide RNA for editing PPO1 and PPO2 genes comprising the nucleotide sequence of SEQ ID NO: 34.

25. An expression cassette or vector encoding the guide RNA of claim 24.

26. A wheat plant cell comprising a Cas9 nuclease and the guide RNA of claim 24.

* * * * *